(12) United States Patent
Kranz

(10) Patent No.: US 7,790,184 B2
(45) Date of Patent: Sep. 7, 2010

(54) CYTOCHROME C SYNTHESIS INHIBITORS

(75) Inventor: Robert Kranz, St. Louis, MO (US)

(73) Assignee: Washington University in St. Louis, St. Louis, MO (US)

( * ) Notice: Subject to any disclaimer, the term of this patent is extended or adjusted under 35 U.S.C. 154(b) by 243 days.

(21) Appl. No.: 11/831,273

(22) Filed: Jul. 31, 2007

(65) Prior Publication Data

US 2008/0032313 A1 Feb. 7, 2008

Related U.S. Application Data

(60) Provisional application No. 60/821,053, filed on Aug. 1, 2006.

(51) Int. Cl.
*A61K 39/02* (2006.01)
(52) U.S. Cl. .................................................. 424/234.1
(58) Field of Classification Search ........................ None
See application file for complete search history.

(56) References Cited

U.S. PATENT DOCUMENTS

| | | | |
|---|---|---|---|
| 5,656,725 | A | 8/1997 | Chittenden et al. |
| 6,043,045 | A | 3/2000 | Hoch et al. |
| 6,066,628 | A | 5/2000 | Stojiljkovic et al. |
| 6,656,703 | B1 | 12/2003 | Murphy et al. |
| 6,913,889 | B2 | 7/2005 | Gerbi et al. |
| 7,132,567 | B2 | 11/2006 | Alberte et al. |
| 7,202,023 | B2 | 4/2007 | Murphy |
| 2006/0051767 | A1 | 3/2006 | Huber et al. |
| 2006/0206946 | A1 | 9/2006 | Hamza |

FOREIGN PATENT DOCUMENTS

WO 98/58541 A1 12/1998

OTHER PUBLICATIONS

Feissner et al 2006 Molecular Microbiology vol. 60 No. 3 pp. 563-577.*
Ren et al 2001 Journal of biological chemistry vol. 276 No. 35 pp. 32591-32596.*
Verkamp et al 1993 Journal of bacteriology vol. 175 No. 5 pp. 1452-1456.*
Allen, et al, "A Cytochrome b 562 Variant with a c-Type Cytochrome CXXCH Heme-binding Motif as a Probe of the *Escherichia coli* Cytochrome c Maturation System", The Journal of Biological Chemistry, 2003, pp. 52075-52083, vol. 278, No. 52.
Beckett, et al, "Four genes are required for the system II cytochrome c biogenesis pathway in *Bordetella pertussis*, a unique bacterial model", Molecular Microbiology, 2000, pp. 465-481, vol. 38(3).
Beckman, et al, "Bacterial cytochromes c biogenesis", Genes and Development, 1992, pp. 268-283, vol. 6.
Beckman, et al, "Cytochromes c biogenesis in a photosynthetic bacterium requires a periplasmic thioredoxin-like protein", Proc. Natl. Acad. Sci. USA, 1993, pp. 2179-2183, vol. 90.

Braun, et al, "Biosynthesis of artificial microperoxidases by exploiting the secretion and cytochrome c maturation apparatuese of *Escherichia coli*", PNAS, 2004, pp. 12830-12835, vol. 101, No. 35.
Datsenko, et al, "One-Step inactivation of chromosomal genes in *Escherichia coli* K-12 using PCR products", PNAS, 2000, pp. 6640-6645, vol. 97, No. 12.
Feissner, et al, "Mutations in Cytochrome Assembly and Periplasmic Redox Pathways in *Bordetella pertussis*", Journal of Bacteriology, 2005, pp. 3941-3949, vol. 187, No. 12.
Feissner, et al, "Recombinant cytochromes c biogenesis systems I and II and analysis of haem delivery pathways in *Escherichia coli*", Molecular Microbiology, 2006, pp. 563-577, vol. 60(3).
Feissner, et al, "Chemiluminescent-based methods to detect subpicomole levels of c-type cytochromes", Analytical Biochemistry, 2003, pp. 90-94, vol. 315.
Fellay, et al, "Interposon mutagenesis of soil and water bacteria: a family of DNA fragments designed for in vitro insertional mutagenesis of Gram-negative bacteria", Gene, 1987, pp. 147-154, vol. 52.
Ferreira, "Mammalian Ferrochelatase", The Journal of Biological Chemistry, 1994, pp. 4396-4400, vol. 269, No. 6.
Goldman, et al, "Use of Heme Reporters for Studies of Cytochrome Biosynthiesis and Heme Transport", Journal of Bacteriology, 1996, pp. 6338-6347, vol. 178, No. 21.
Guzman, et al, "Tight Regulation, Modulation, and High-Level Expression by Vectors Containing the Arabinose PBAD Promoter", Journal of Bacteriology, 1995, pp. 4121-4130, vol. 177, No. 14.
Herbaud, et al, "*Escherichia coli* is able to produce heterologous tetraheme cytochrome c3 when the ccm genes are co-expressed", Biochimica et Biophysica Acta, 2000, pp. 18-24, vol. 1481.
Khlebnikov, et al, "Regulatable Arabinose-Inducible Gene Expression System with Consistent Control in All Cells of a Culture", Journal of Bacteriology, 2000, pp. 7029-7034, vol. 182. No. 24.
Kranz, "Isolation of Mutants and Genes Involved in Cytochromes c Biosynthesis in Rhodobacter capsulatus", Journal of Bacteriology, 1989, pp. 456-464, vol. 171, No. 1.
Kranz, et al, "Molecular mechanisms of cytochrome c biogenesis: three distinct systems", Molecular Microbiology, 1998, pp. 383-396, vol. 29(2).
Kwon, et al, "A High-Throughput Screen for Porphyrin Metal Chelatases: Application to the Directed Evolution of Ferrochelatases for Metalloporphyrin Biosynthesis", ChemBioChem, 2004, pp. 1069-1074, vol. 5.
Loida, et al, "Novel Inhibitors of Glutamyl-tRNAGLU Reductase Identified through Cell-Based Screening of the Heme/Chlorophyll Biosynthetic Pathway", Archives of Biochemistry and Biophysics, 1999, pp. 230-237, vol. 372, No. 2.
Moody, et al, "Ferric Iron Reductase of *Rhodopseudomonas sphaeroides*", Journal of Bacteriology, 1985, pp. 1120-1125, vol. 163, No. 3.

(Continued)

*Primary Examiner*—Robert B Mondesi
*Assistant Examiner*—Nina A Archie
(74) *Attorney, Agent, or Firm*—Polsinelli Shughart PC

(57) ABSTRACT

The invention provides methods for identifying a compound that inhibits cytochrome c synthesis. This invention further provides a method for the high throughput screening of compounds that inhibit cytochrome c synthesis.

11 Claims, 32 Drawing Sheets

OTHER PUBLICATIONS

Richard-Fogal, et al, "Heme Concentration Dependence and Metalloporphyrin Inhibition of the System I and II Cytochrome c Assembly Pathways", Journal of Bacteriology, 2007, pp. 455-463, vol. 189, No. 2.

Tomb, et al, "The complete genome sequence of the gastric pathogen *Helicobacter pylori*", Nature, 1997, pp. 539-547, vol. 388.

Varnado, et al, "System for the expression of recombinant hemoproteins in *Escherichia coli*", Protein Expression and Purification, 2004, pp. 76-83, vol. 35.

Braun, et al, "A heme tag for in vivo synthesis of artificial cytochromes", Appl. Microbiol Biotechnol, 2005, pp. 234-239, vol. 67.

\* cited by examiner

A

B

A

B

C

D

A  PhoA Western

| | Δccm + pSysI + pc$_4$:PhoA + pHPEX2 | | | | | Δccm + pc$_4$:PhoA + pHPEX2 | |
|---|---|---|---|---|---|---|---|
| Hemin (μM) | 0 | 2 | 8 | 12.5 | 25 | 0 | 0 |
| ZnPPIX (μM) | 12.5 | 12.5 | 12.5 | 12.5 | 12.5 | 12.5 | 25 |
| Lane | 1 | 2 | 3 | 4 | 5 | 6 | 7 |

← cyt c$_4$:PhoA
← PhoA'

B  Heme stain

| | Δccm + pSysI + pc$_4$:PhoA + pHPEX2 | | | | |
|---|---|---|---|---|---|
| Hemin (μM) | 0 | 2 | 8 | 12.5 | 25 |
| ZnPPIX (μM) | 12.5 | 12.5 | 12.5 | 12.5 | 12.5 |
| Lane | 1 | 2 | 3 | 4 | 5 |

← cyt c$_4$:PhoA

FIG. 22

| E. coli strain: | Δccm | | | Δccm + pBADc4:6xHis | | | Δccm + pSysI + pBADc4:6xHis | | | c4:6XHis | ECL only |
|---|---|---|---|---|---|---|---|---|---|---|---|
| Culture volume: | 5 μl | 7.5 μl | 10 μl | 5 μl | 7.5 μl | 10 μl | 5 μl | 7.5 μl | 10 μl | 5 μl | 5 μl |
| A | 261 | 122 | 45 | 300 | 50 | 15 | 3120 | 3035 | 1694 | 36163 | 83 |
| B | 191 | 97 | 34 | 256 | 40 | 15 | 2916 | 2975 | 1438 | 13740 | 63 |
| C | 194 | 92 | 32 | 236 | 32 | 9 | 2913 | 2946 | 1512 | 5741 | 52 |
| D | 170 | 85 | 32 | 253 | 40 | 6 | 2828 | 2879 | 1450 | 2076 | 47 |
| E | 156 | 87 | 25 | 264 | 29 | 5 | 2862 | 2910 | 1728 | 136 | 40 |
| F | 152 | 83 | 21 | 268 | 29 | 6 | 2884 | 3019 | 1600 | 160 | 43 |
| G | 158 | 84 | 23 | 272 | 33 | 7 | 2910 | 2984 | 1514 | 173 | 47 |
| H | 169 | 97 | 26 | 280 | 29 | 10 | 2983 | 2998 | 1422 | 182 | 61 |
| | 1 | 2 | 3 | 4 | 5 | 6 | 7 | 8 | 9 | 11 | 12 |

SEQUENCE LISTING

```
<160> NUMBER OF SEQ ID NOS: 21

<210> SEQ ID NO 1
<211> LENGTH: 60
<212> TYPE: DNA
<213> ORGANISM: Escherichia coli

<400> SEQUENCE: 1
cgcctgcgcg atactacgtt caatcaccgc acggcgagta gtgtaggctg gagctgcttc    60

<210> SEQ ID NO 2
<211> LENGTH: 60
<212> TYPE: DNA
<213> ORGANISM: Escherichia coli

<400> SEQUENCE: 2
acgctgaacg caggagagtg ggtacaaatc accggtagca catatgaata tcctccttag    60

<210> SEQ ID NO 3
<211> LENGTH: 32
<212> TYPE: DNA
<213> ORGANISM: Escherichia coli

<400> SEQUENCE: 3
ttgcagatct atgcttgaag ccagagagtt ac                                  32

<210> SEQ ID NO 4
<211> LENGTH: 33
<212> TYPE: DNA
<213> ORGANISM: Escherichia coli

<400> SEQUENCE: 4
cggaattctt tttatttact ctcctgcggc gac                                 33

<210> SEQ ID NO 5
<211> LENGTH: 30
<212> TYPE: DNA
<213> ORGANISM: Escherichia coli

<400> SEQUENCE: 5
ggcgaattct catatggcct cctgctgttg                                     30

<210> SEQ ID NO 6
<211> LENGTH: 33
<212> TYPE: DNA
<213> ORGANISM: Escherichia coli

<400> SEQUENCE: 6
gacccagcca tatgatgcca gaaattggta acg                                 33

<210> SEQ ID NO 7
<211> LENGTH: 32
<212> TYPE: DNA
<213> ORGANISM: Escherichia coli

<400> SEQUENCE: 7
```
ccaatgaatt ccttattgtg cggcctcctt ac 32

<210> SEQ ID NO 8
<211> LENGTH: 32
<212> TYPE: DNA
<213> ORGANISM: Escherichia coli

<400> SEQUENCE: 8
tataagcttt tttgccgatt tcggcctatt gg 32

<210> SEQ ID NO 9
<211> LENGTH: 27
<212> TYPE: DNA
<213> ORGANISM: Escherichia coli

<400> SEQUENCE: 9
atcaggctga aaatcttctc tcatccg 27

<210> SEQ ID NO 10
<211> LENGTH: 27
<212> TYPE: DNA
<213> ORGANISM: Escherichia coli

<400> SEQUENCE: 10
agtcgctagc aggaggattt catgaag 27

<210> SEQ ID NO 11
<211> LENGTH: 23
<212> TYPE: DNA
<213> ORGANISM: Escherichia coli

<400> SEQUENCE: 11
gtgctgcaag gcgattaagt tgg 23

<210> SEQ ID NO 12
<211> LENGTH: 48
<212> TYPE: DNA
<213> ORGANISM: Bordetella pertussis

<400> SEQUENCE: 12
acgggtacct cagtggtggt ggtggtggtg ccgcaagccc gcggcgta 48

<210> SEQ ID NO 13
<211> LENGTH: 32
<212> TYPE: DNA
<213> ORGANISM: Helicobacter pylori

<400> SEQUENCE: 13
ggaaagatct atgaagaatc tcaaaagcct gc 32

<210> SEQ ID NO 14
<211> LENGTH: 28
<212> TYPE: DNA
<213> ORGANISM: Helicobacter pylori

<400> SEQUENCE: 14
ttcgaattcc gcgtctaata ggggttgg 28

<210> SEQ ID NO 15
<211> LENGTH: 33
<212> TYPE: DNA
<213> ORGANISM: Escherichia coli

<400> SEQUENCE: 15

-continued ggtcccatgg tatatgcgct gcgctcgaat atc 33

<210> SEQ ID NO 16
<211> LENGTH: 35
<212> TYPE: DNA
<213> ORGANISM: Escherichia coli

<400> SEQUENCE: 16
ctgctcgagt gatgctgggt ccttataaac actcg 35

<210> SEQ ID NO 17
<211> LENGTH: 33
<212> TYPE: DNA
<213> ORGANISM: Escherichia coli

<400> SEQUENCE: 17
caggtaccgg aggctgcatg aatattcgcc gta 33

<210> SEQ ID NO 18
<211> LENGTH: 48
<212> TYPE: DNA
<213> ORGANISM: Escherichia coli

<400> SEQUENCE: 18
acgctgcagt cagtggtggt ggtggtggtg tgatgctggg tccttata 48

<210> SEQ ID NO 19
<211> LENGTH: 60
<212> TYPE: DNA
<213> ORGANISM: Escherichia coli

<400> SEQUENCE: 19
ctatcaacgt tggtattatt tcccgcagac atgacccttt gtgtaggctg gagctgcttc 60

<210> SEQ ID NO 20
<211> LENGTH: 60
<212> TYPE: DNA
<213> ORGANISM: Escherichia coli

<400> SEQUENCE: 20
tgatgtactg ctactccagc ccgaggctgt cgcgcagaat catatgaata tcctccttag 60

<210> SEQ ID NO 21
<211> LENGTH: 239
<212> TYPE: PRT
<213> ORGANISM: Bordetella pertussis

<400> SEQUENCE: 21

```
Met Lys Arg Val Leu Ser Arg Met Leu Val Ala Ser Gly Leu Val Leu
1               5                   10                  15

Gly Ala Ser Val His Ser Met Ser Phe Ala Ala Asp Gly Ala Ala Gly
            20                  25                  30

Pro Ala Lys Pro Asp Ala Ala Lys Gly Ala Gln Leu Tyr Asp Gln Gly
        35                  40                  45

Asp Ala Ser Arg Gly Val Ile Ala Cys Ala Ser Cys His Gly Ala Ala
    50                  55                  60

Gly Ser Ser Thr Ile Pro Ala Asn Pro Asn Leu Ala Ala Gln Pro His
65                  70                  75                  80

Glu Tyr Leu Val Lys Gln Leu Thr Glu Phe Lys Val Lys Glu Gly Glu
                85                  90                  95
```

```
Lys Leu Pro Leu Arg Met Gly Pro Gly Gly Asn Pro Thr Pro Met Thr
            100                 105                 110

Ala Met Ala Gln Pro Leu Thr Ala Gln Asp Met Gln Asn Val Ala Leu
        115                 120                 125

Tyr Leu Ser Gln Gln Pro Leu Lys Glu Pro Ala Thr Ala Gly His Glu
    130                 135                 140

Asn Leu Val Glu Leu Gly Gln Lys Ile Trp Arg Gly Gly Leu Ala Asp
145                 150                 155                 160

Arg Asn Val Pro Ala Cys Ala Ala Cys His Gly Ala Thr Gly Ala Gly
                165                 170                 175

Ile Pro Gly Gln Tyr Pro Arg Leu Ser Gly Gln Phe Ser Ser Tyr Ile
            180                 185                 190

Glu Glu Gln Leu Lys Leu Phe Arg Ser Gly Glu Arg Gly Asn Ser Val
        195                 200                 205

Pro Met His Asp Ile Ala Asp Arg Met Ser Asp Ala Asp Ile Lys Ala
        210                 215                 220

Val Ala Asp Tyr Ala Ala Gly Leu Arg His His His His His His
225                 230                 235
```

CYTOCHROME C SYNTHESIS INHIBITORS

CROSS-REFERENCE TO RELATED APPLICATION

This application claims priority from Provisional Application Ser. No. 60/821,053 filed on Aug. 1, 2006, which is hereby incorporated by reference in its entirety.

GOVERNMENTAL RIGHTS

This work was supported by the U.S. Department of Health and Human Services/National Institutes of Health grant number 5R01 GM047909-11. The U.S. government has certain rights in this invention.

FIELD OF THE INVENTION

The present invention generally relates to screening methods for the identification of compounds and compositions that inhibit cytochrome c.

BACKGROUND

The treatment of bacterial infections is a perpetual challenge in the medical community. Many powerful antibiotics exist that target different aspects of bacterial physiology. Some classes of antibiotics are toxic to bacteria, while other classes of antibiotics arrest the propagation of the bacteria in the body, giving the immune system adequate time to eliminate the bacterial infection. Penicillins, bacitracin, cephalosporins, and vancomycin disrupt the process of cell wall development in bacteria. Other antibiotics such as the aminoglycosides, chloramphenicol, erythromycin, clindamycin, tetracyclines, trimethoprim, and sulfanimides inhibit or disrupt some aspect of protein synthesis in the targeted bacteria. Still other antibiotics such as quinolones and rifampin disrupt the process of DNA or RNA synthesis in bacteria. Although the antibiotics listed above represent a powerful arsenal of treatments for bacterial infections, the increasingly widespread use of these antibiotics has resulted in the development of bacterial strains that are resistant to many of the currently available antibiotics.

Some treatment-resistant bacterial strains have plagued hospitals for decades, such as *Staphylococcus aureus* (responsible for Staph infections), *Streptococcus pneumoniae* (responsible for pneumonia and meningitis), and *Proteus vulgaris* (causing urinary tract infections). The incidence of infections caused by these bacteria and others show signs of increasing incidence in recent years. In 2003, epidemiologists reported that 5 to 10 percent of patients admitted to hospitals acquire an infection during their stay and that the risk for a hospital-acquired infection has risen steadily in recent decades. In November 2004, the Centers for Disease Control and Prevention (CDC) reported an increasing number of *Acinetobacter baumannii* bloodstream infections in patients at military medical facilities treating service members from Afghanistan and the Iraq/Kuwait region.

There exists a need to identify new and effective antibiotic compounds. Antibiotic therapies generally disrupt processes that are unique to bacteria, such as the enzymes and components of the cell wall and the prokaryote ribosomes. The efficacy and safety of antibiotics depend upon the inhibition of biochemical systems that are unique to bacteria, and that can be safely inhibited without producing detrimental or undesired side effects in the individual receiving the antibiotic therapy. As bacteria become increasingly resistant to existing therapies, it has become difficult to identify unique biochemical pathways that may be inhibited in bacteria that are not also present in the cells of the patients to be treated.

The biogenesis of cytochrome c in bacteria is a pathway that is a promising target for antibiotic therapy. Cytochrome c is an electron transport protein that is essential for most aerobic and anaerobic respiratory chains, as well as other cellular processes such as photosynthesis and apoptosis. Although three different cytochrome c biogenesis pathways have been identified in various organisms, two of these pathways are unique to bacteria and plants, and only the last remaining biogenesis pathway is unique to vertebrates, invertebrates, fungus, and some protozoa. Further, cytochrome c is synthesized on the outside of the cytoplasmic membrane of the bacteria cell, making the biogenesis of cytochrome c particularly amenable to inhibition by small molecules or proteins.

Antibiotic drug discovery is generally a random and laborious process of biological screening of compounds against a panel of known bacteria proteins. The process of antibiotic drug discovery would be greatly facilitated by a method of screening that directly measures the effects of a compound on its target protein in vivo. Further, optimizing this screening method to achieve a high-throughput screening method would greatly facilitate the process of developing new and effective antibiotics to expand the dwindling arsenal of existing antibiotics.

SUMMARY

Among the several aspects of the invention is provided a method for identifying a compound that inhibits cytochrome c synthesis in a bacterial cell. The method generally comprises contacting the compound with a transfected bacterial cell and measuring the amount of cytochrome c synthesized using a transfected reporter protein for cytochrome c.

Other aspects and features of the invention are described in more detail below.

Figure 6:
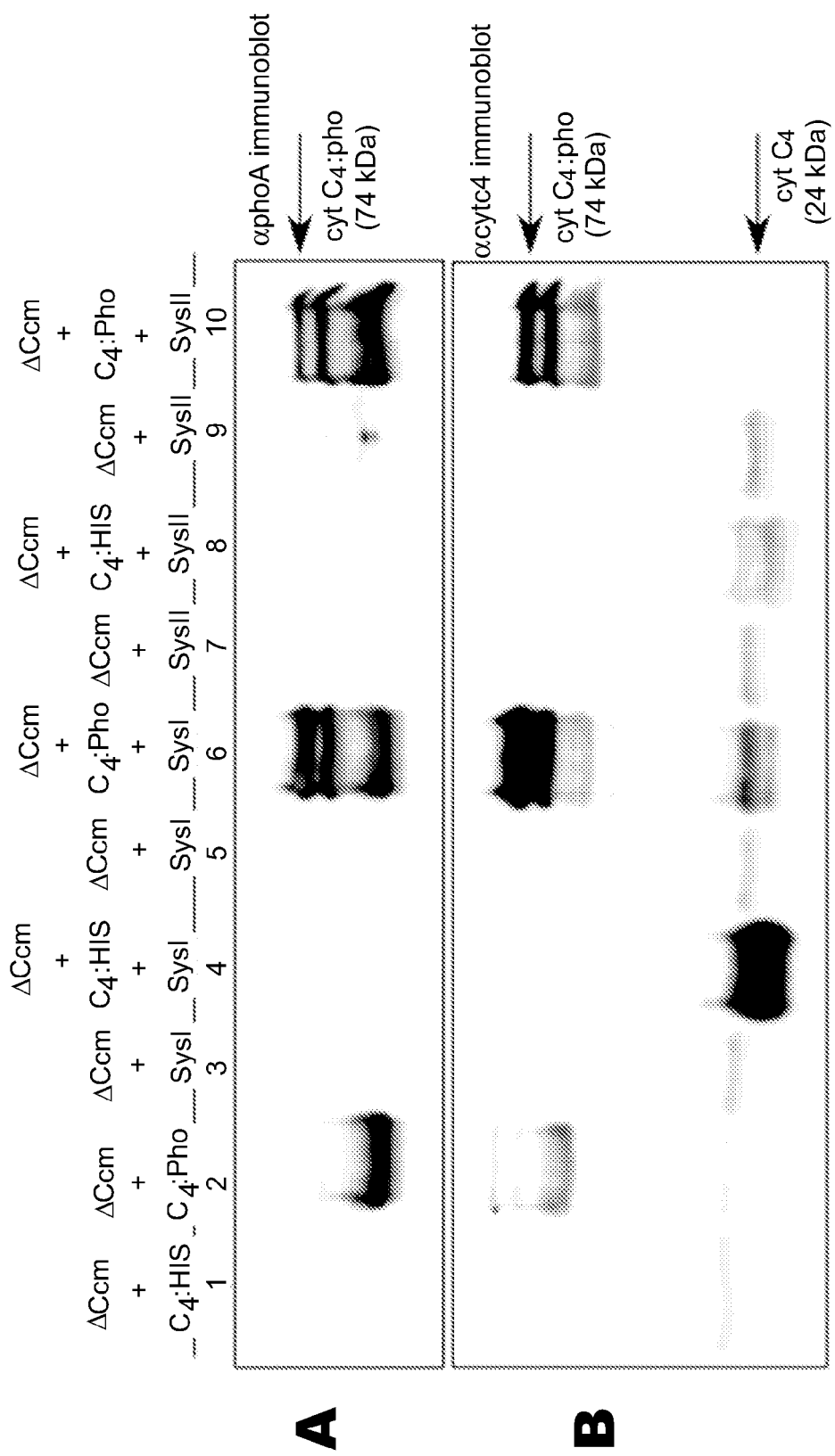

FIG. 6. Western blots and heme stains indicating the stabilization of holocytochrome $c_4$ when heme is attached by the system I and II pathways. (A, B) Western blots of periplasmic shock proteins from the indicated *E. coli* strains. Designations (above lane numbers) are as described in FIG. 4. A) Antisera to alkaline phosphatase. B) Cytochrome $c_4$ antisera immunoblotted against the same extracts as in (A). C) The cytochrome $c_4$ hexahistidine tagged proteins from the indicated strains were purified over an affinity column and stained for heme or in (D) immunoblotted with cytochrome $c_4$ antisera. For panels C and D, the di-heme holocytochrome $c_4$ and endogenously proteolyzed 12 kDa holocytochrome $C_4$ proteins are cartooned on the right, as described in the text.

Figure 7A:
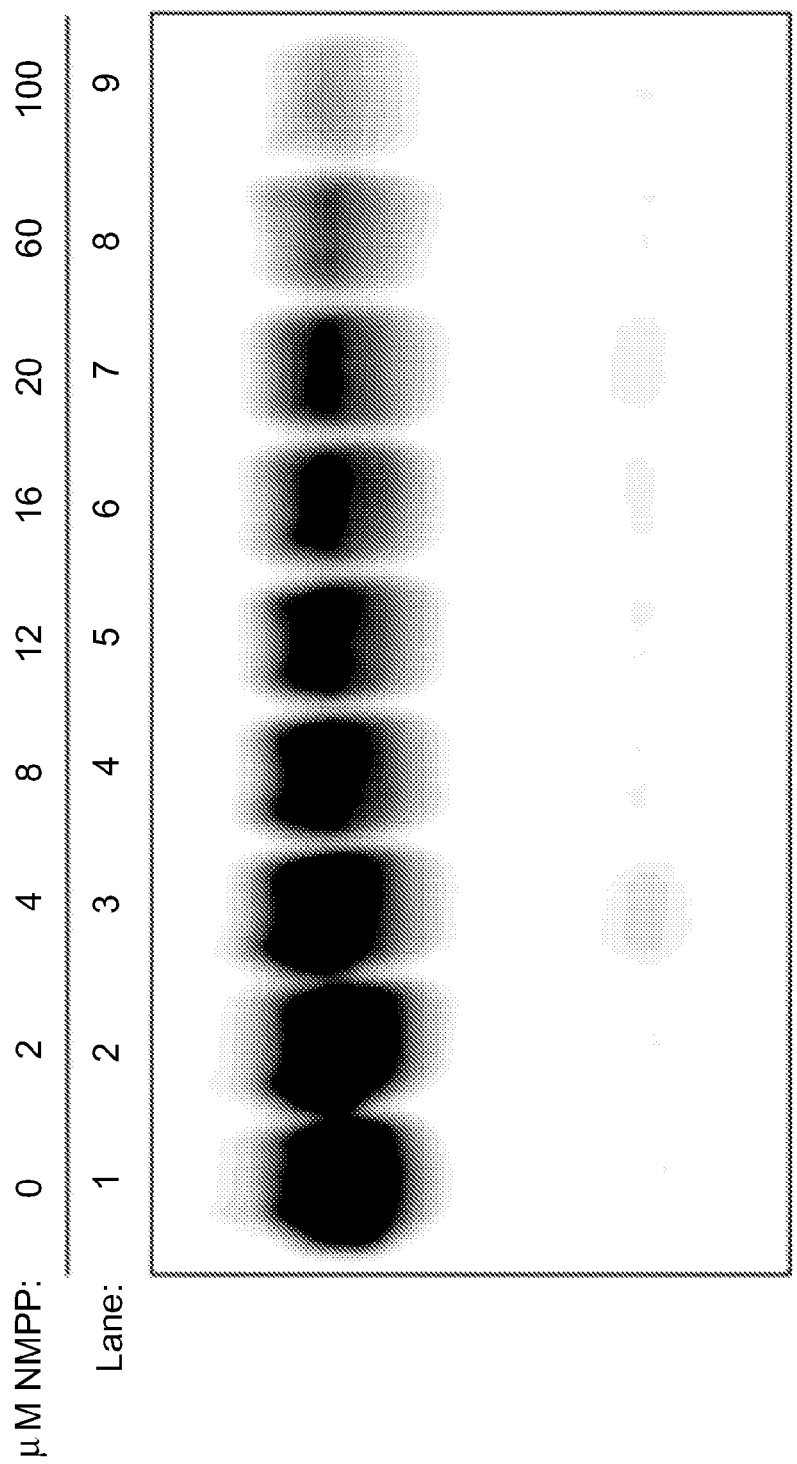
Figure 7B:
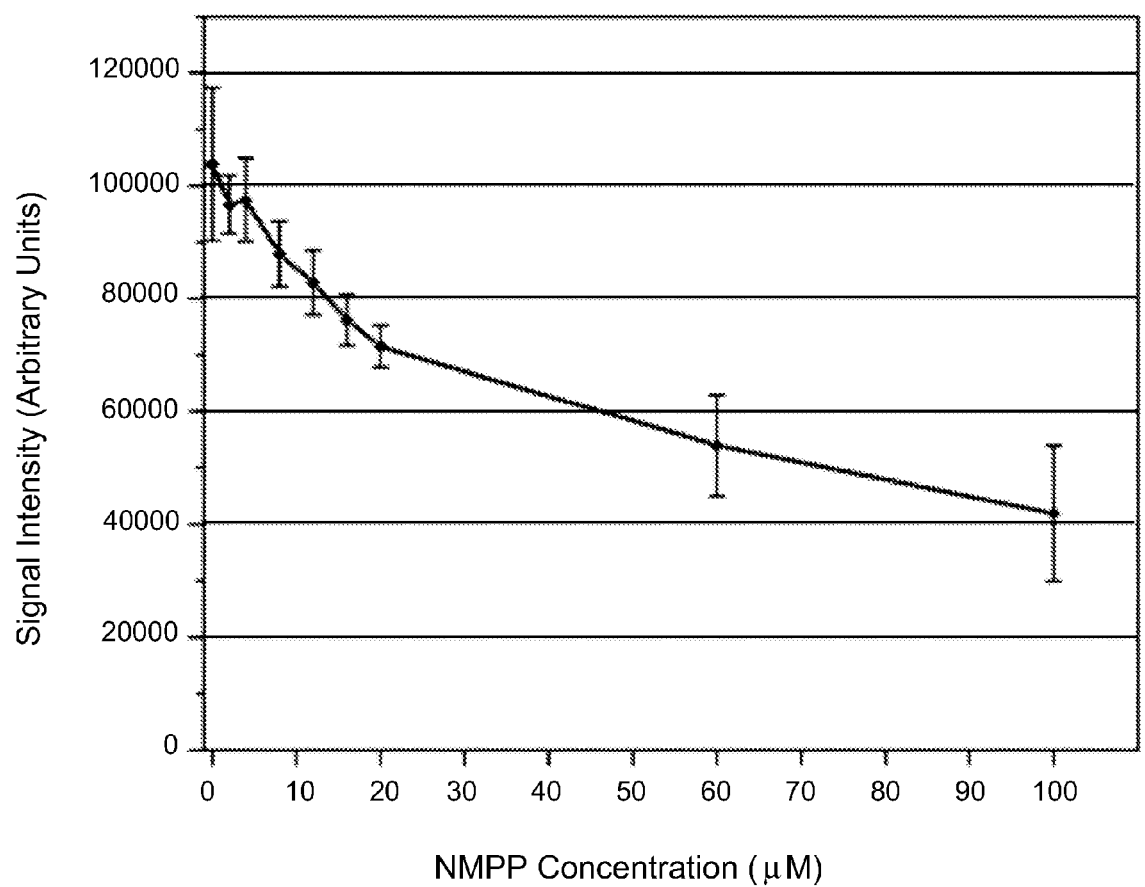

FIG. 7. Cytochrome $c_4$ synthesis by system I and inhibition with N-methylprotoporphyrin. RKI 03 cultures containing pRGK333 and pRGK332 were grown and then IPTG and NMPP were added to induce the synthesis of system I proteins and inhibit heme biosynthesis, respectively. One hour later, the cytochrome $c_4$:His reporter was induced with arabinose for three hours. A) Representative heme stain of soluble B-Per protein extracts from above cultures. B) Quantification of heme stain intensity (in arbitrary units) with respect to NMPP concentration (average of 3 trials, error bars represent standard error).

Figure 8A:
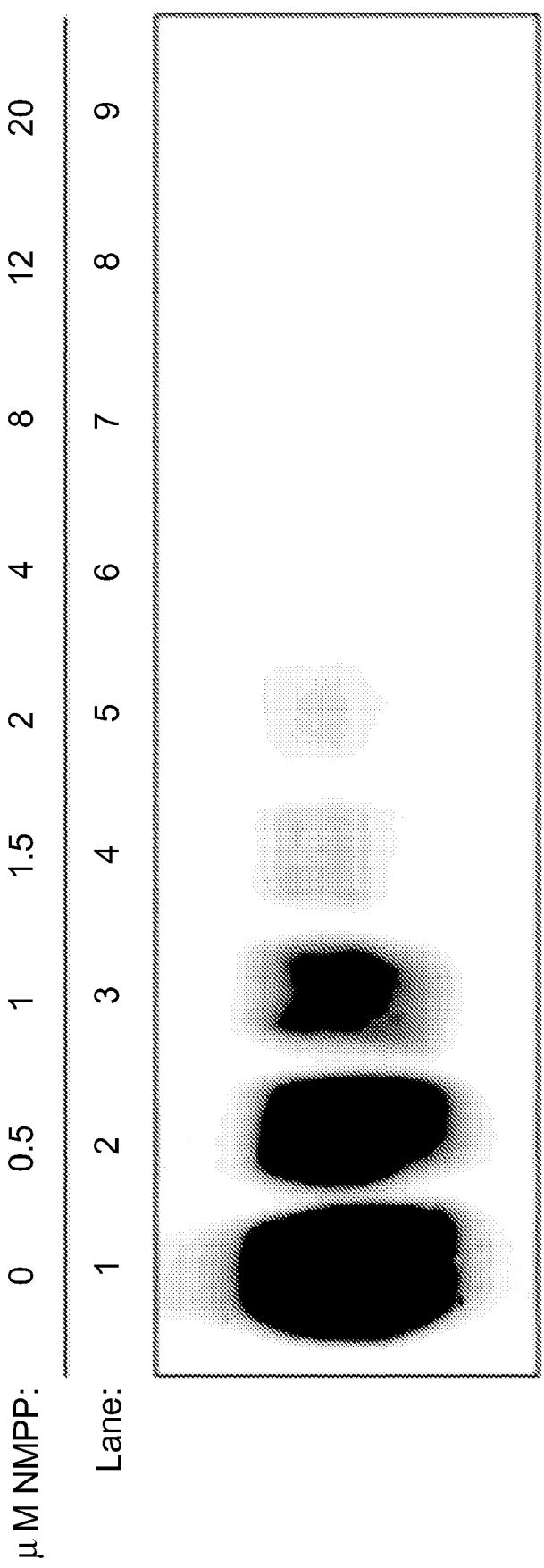
Figure 8B:
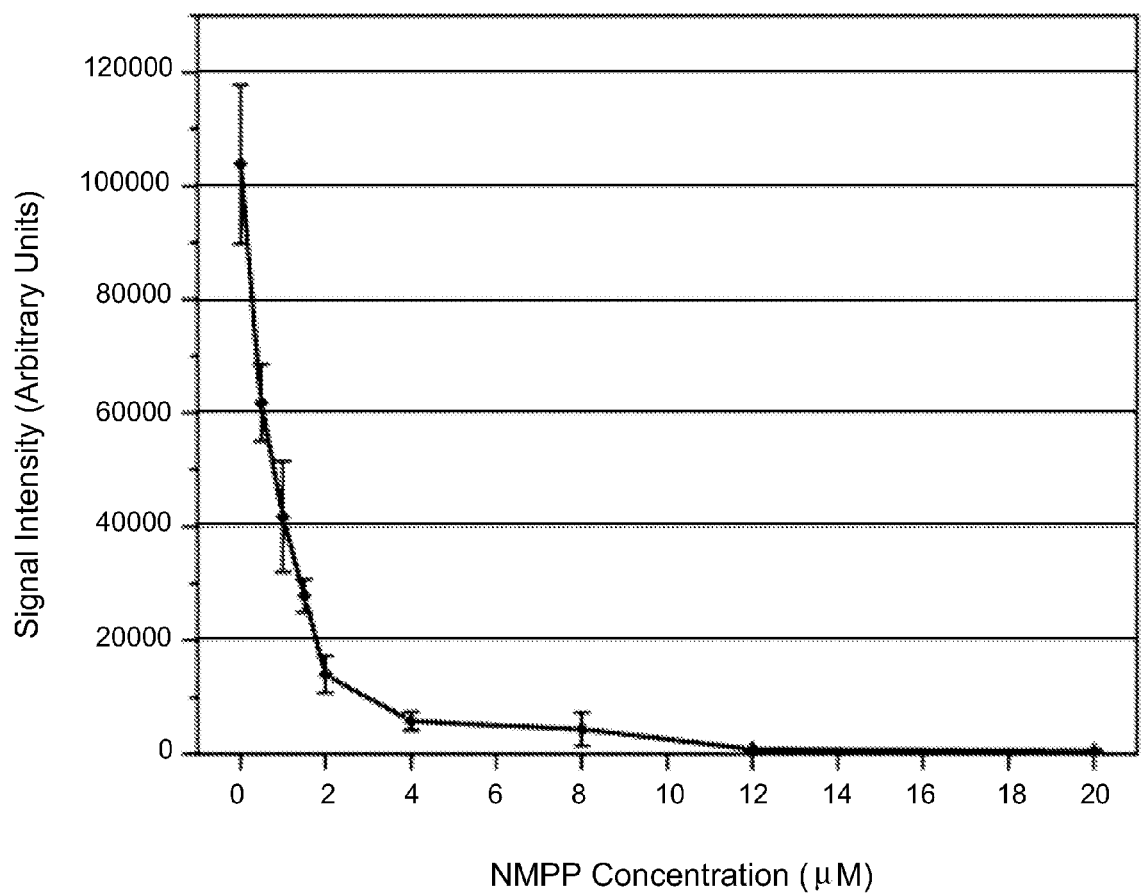

FIG. 8. Cytochrome $c_4$ synthesis by system and inhibition with N-methylprotoporphyrin. A) RKIO3 cultures containing pRGK334 and pRGK332 were grown and then IPTG and NMPP were added to induce the synthesis of system II proteins and inhibit heme biosynthesis, respectively. One hour later, the cytochrome $c_4$:His reporter was induced with arabinose for three hours. A) Representative heme stain of soluble B-Per protein extracts from above cultures. B) Quantification of heme stain intensity (in arbitrary units) with respect to NMPP concentration (average of 4 trials, error bars represent standard error).

Figure 9:
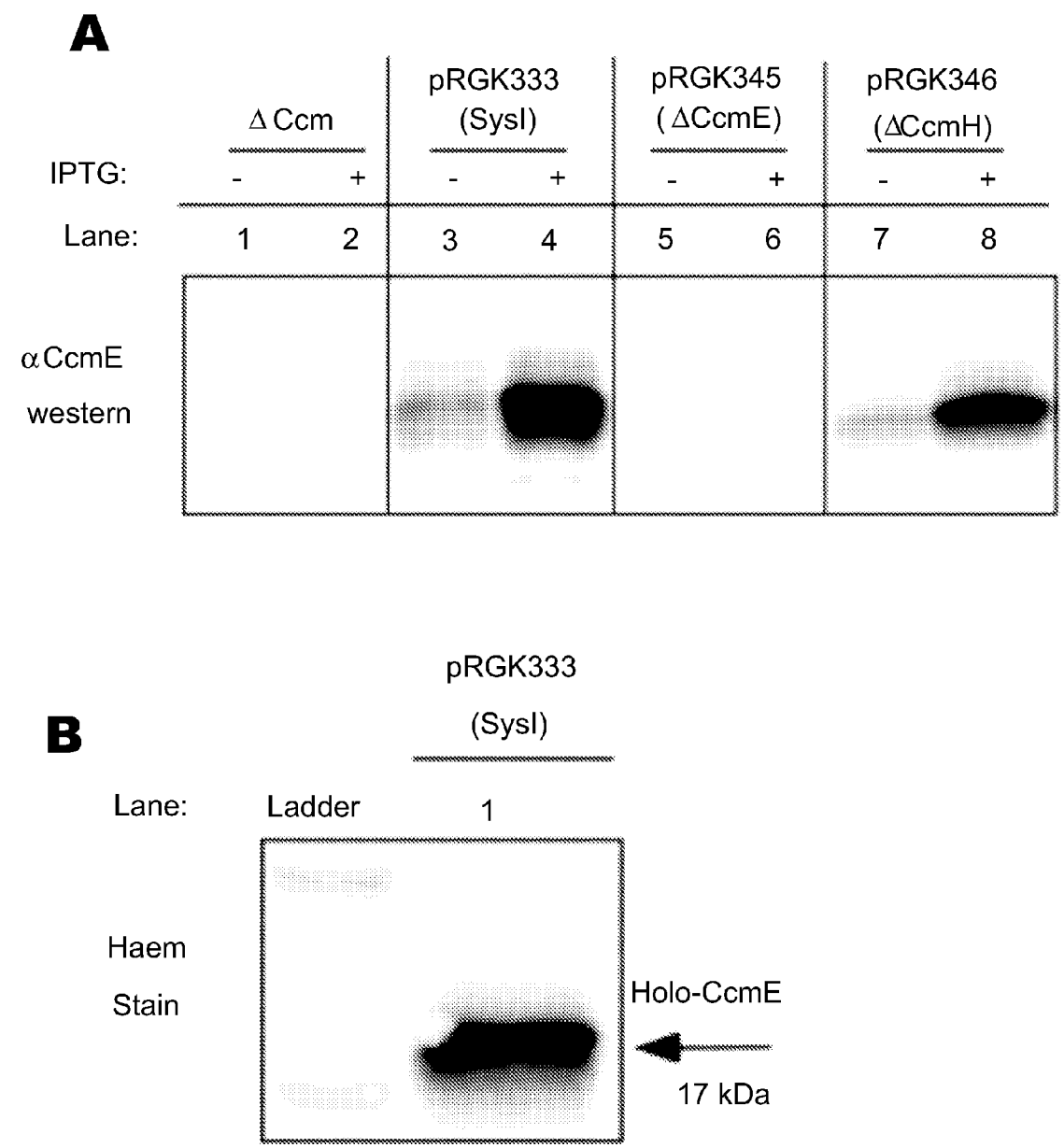

FIG. 9. Holo-CcmE in the recombinant system I as a heme reservoir. A) Western blot using CcmE antisera of membrane proteins from IPTG induced and uninduced RK 103 cultures with the indicated plasmids. B) Heme stain of membrane proteins separated by SDS PAGE from uninduced RKIO3 expressing pRGK333. (20 mg membrane protein loaded per lane.)

Figure 10:
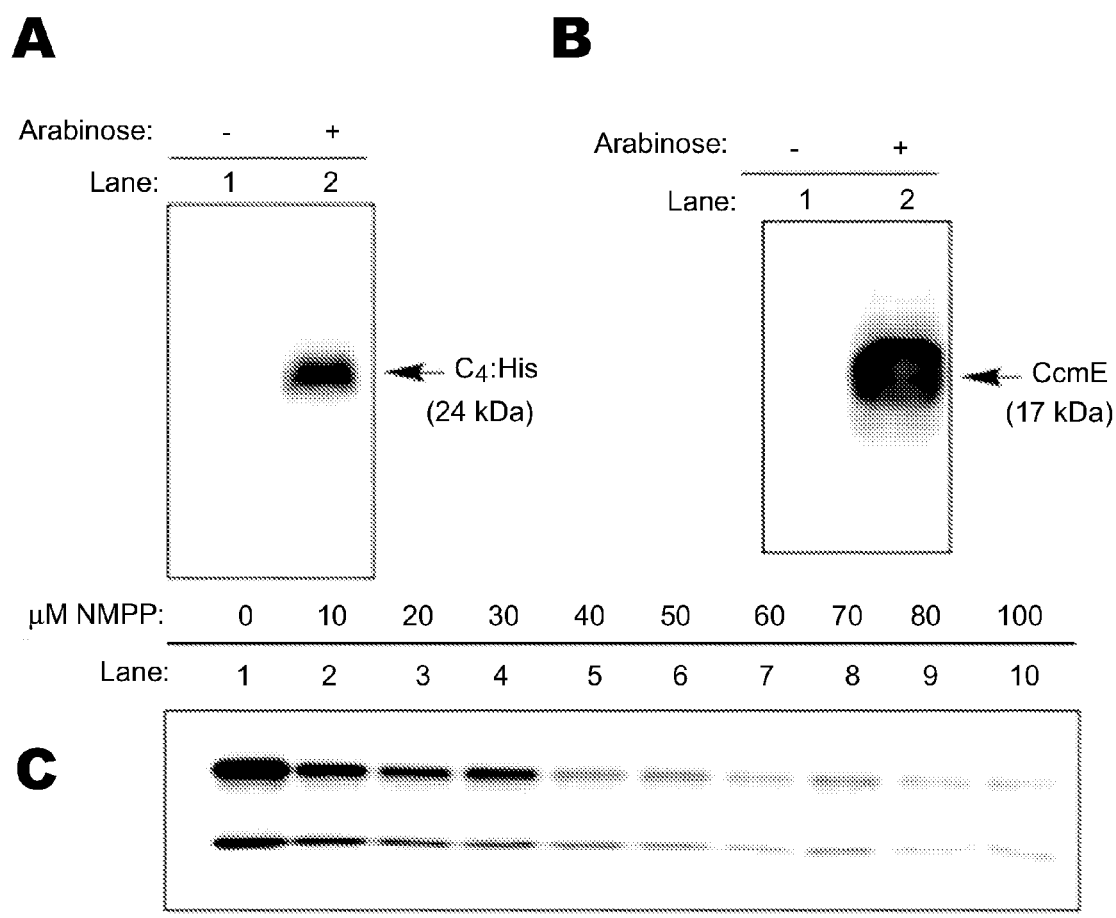
Figure 10D:
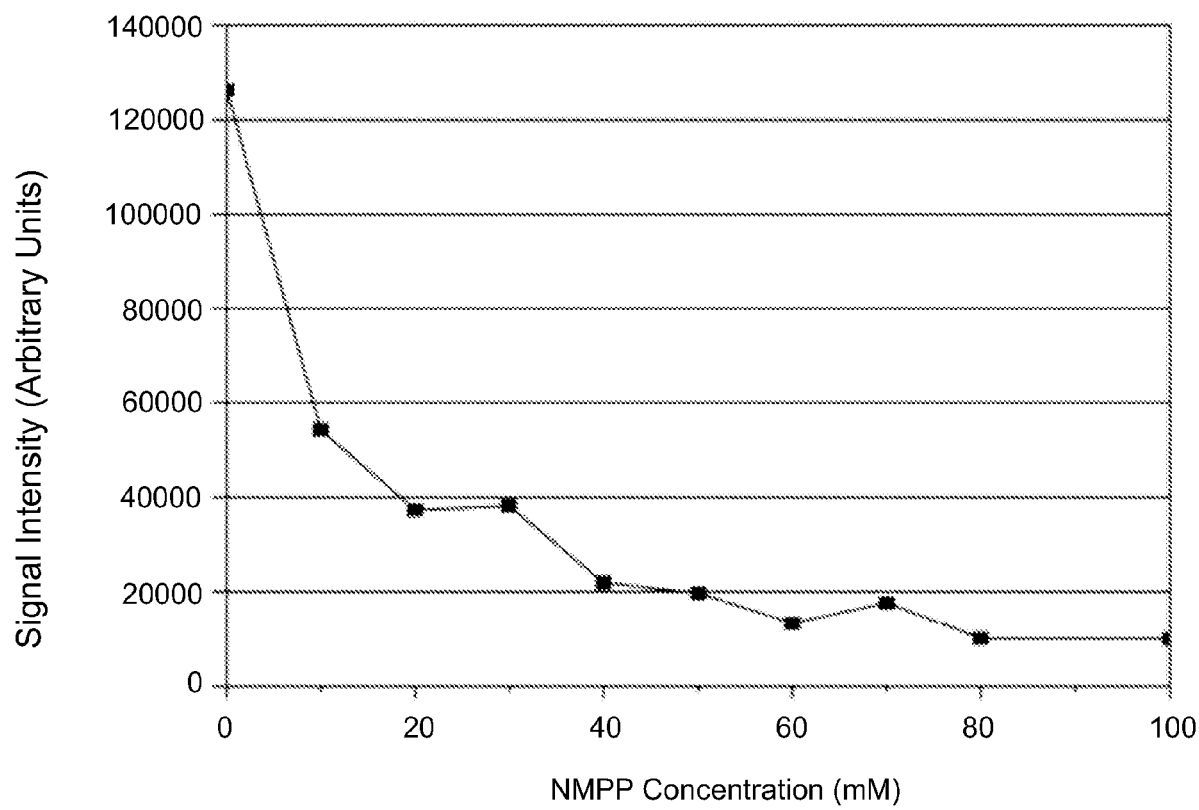

FIG. 10. Arabinose-induciblity of cytochrome $c_4$:His/CemE and inhibition with N-methylprotoporphyrin. (A-D) Cultures of RKIO3 containing pRGK345 and pRGK349 were grown and then IPTG was added to induce the synthesis of all system I proteins, except CcmE, and arabinose was added to induce the synthesis of cytochrome $c_4$:His and CcmE. A) Heme stain of holocytochrome $c_4$:His without and with arabinose. 20 mg of B-per extract loaded per lane. B) Western blot using CcmE antisera of same membrane as in (A). C) Representative heme stain of Ni2+ affinity purified holocytochrome $c_4$:His from RKIO3 cultures containing pRGK34S and pRGK349 performed as described in FIG. 7 legend. D) Quantification of heme stainable intensity (in arbitrary units) with respect to NMPP concentration (average of 2 trials).

Figure 11:
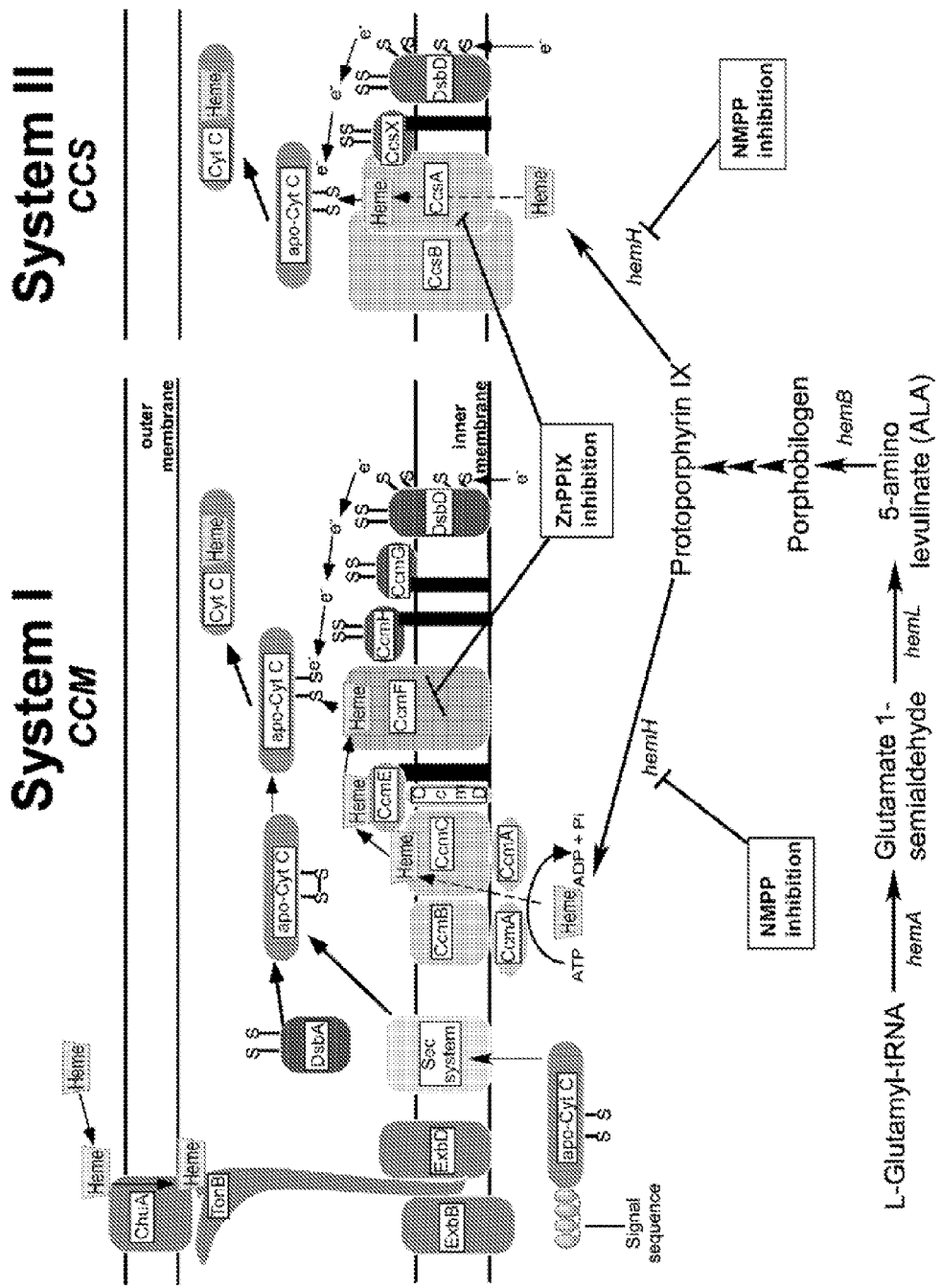

FIG. 11. Diagram of the current working model for c-type cytochromes biogenesis from systems I and II. Also shown are models for the HPEX system (ChuA) heme porin pathway used in this study and for the first dedicated step in heme biosynthesis. (^) denotes potential targets for inhibitors used in the current study.

Figure 12:
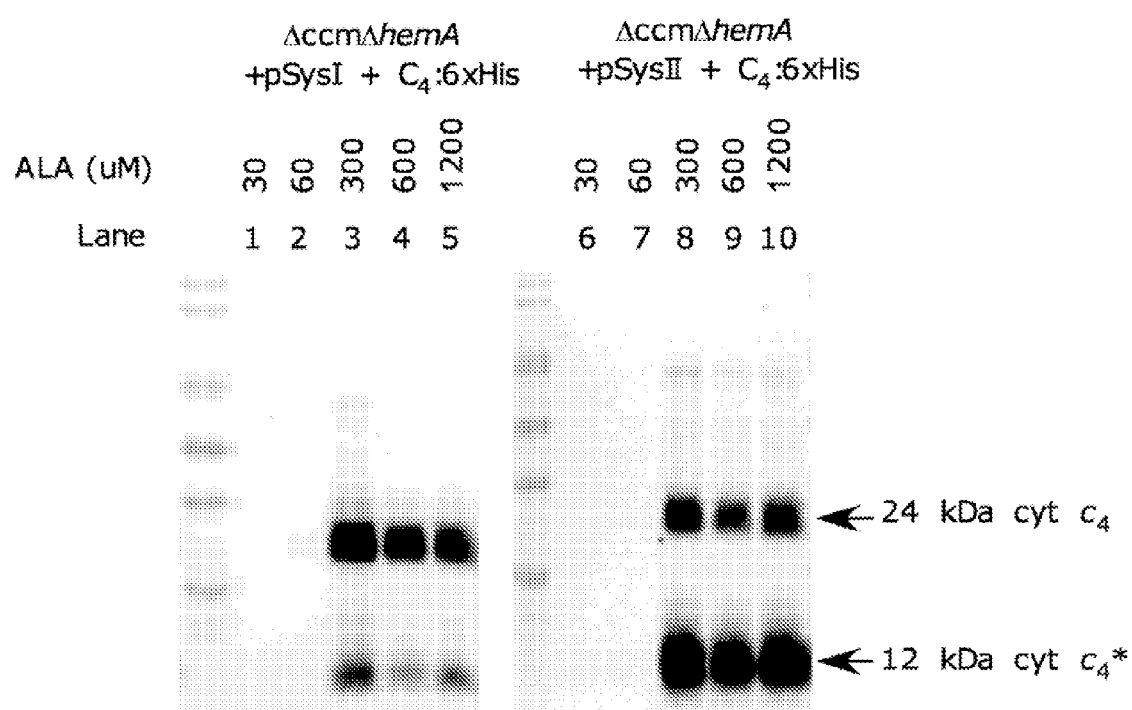

FIG. 12. Heme stains of cytochrome $c_4$ with increasing concentrations of ALA. *E. coli* DccmDhemA containing pRGK333 (Lanes 1-5) or pRGK334 (Lanes 6-10) were diluted into fresh LB broth without ALA, depleting intracellular ALA. ALA was added (concentrations in mM above corresponding lane number) along with 1 mM IPTG for one hour. The cytochrome $c_4$:6xHis was induced with 0.2% arabinose for three hours and soluble B-PER protein extracts were prepared. Above each panel pSysI indicates pRGK333, pSysII indicates pRGK334, and c4:6xHis indicates pRGK332.

Figure 13:
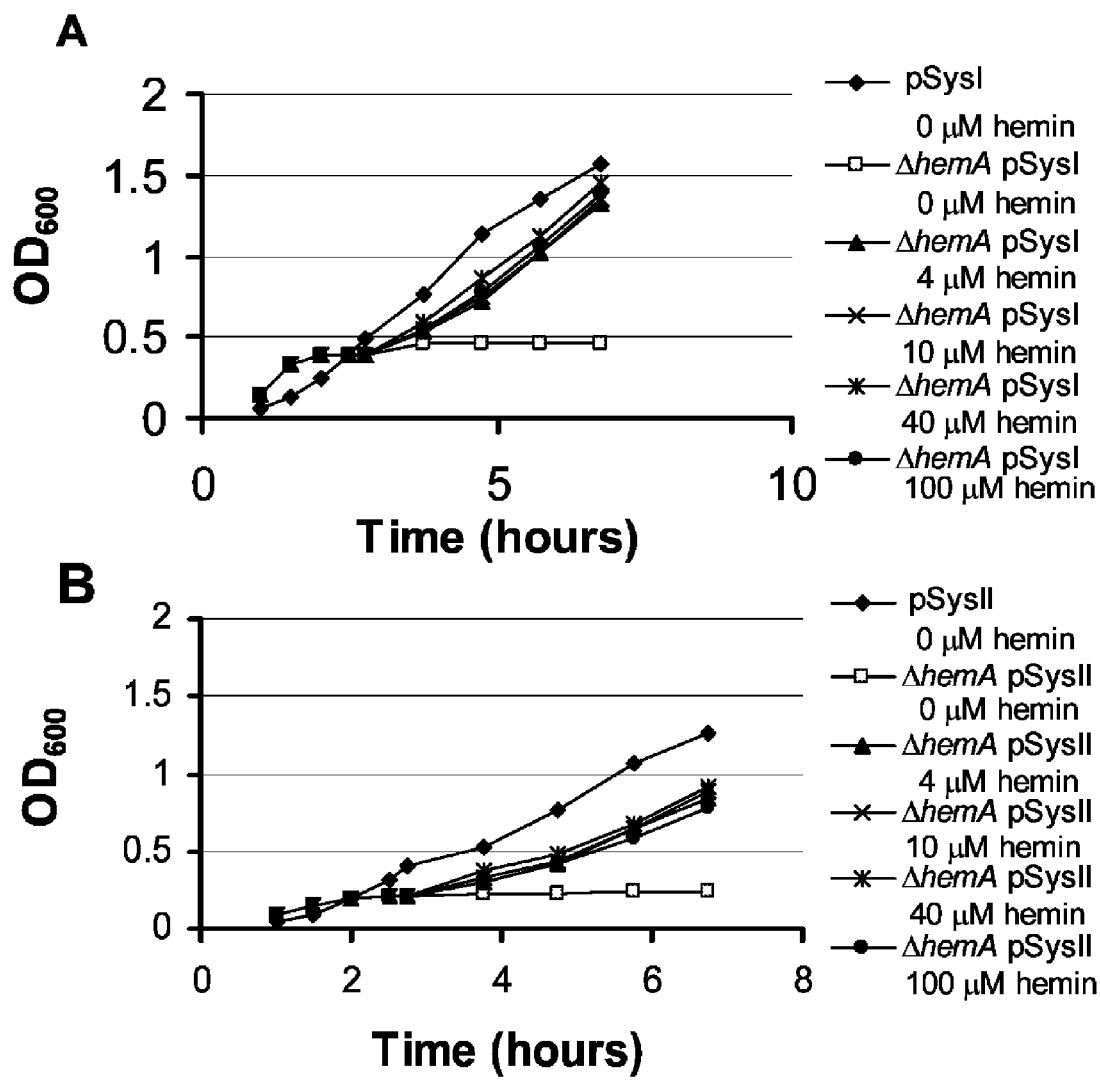

FIG. 13. Growth of *E. coli* DccmDhemA with exogenous heme. Overnight cultures of *E. coli* DccmDhemA or containing pHPEX2 and (A) pRGK333 or (B) pRGK334 were diluted into LB broth without ALA or heme. The cultures were incubated aerobically at 37° C. for two and one-half hours to exhaust the cultures for ALA. Heme was added at the indicated concentrations when noted and growth (A600) was measured. For reference, the growth of *E. coli* Dccm (wild-type) containing either pRGK333 or pRGK334 is shown (t).

Figure 14:
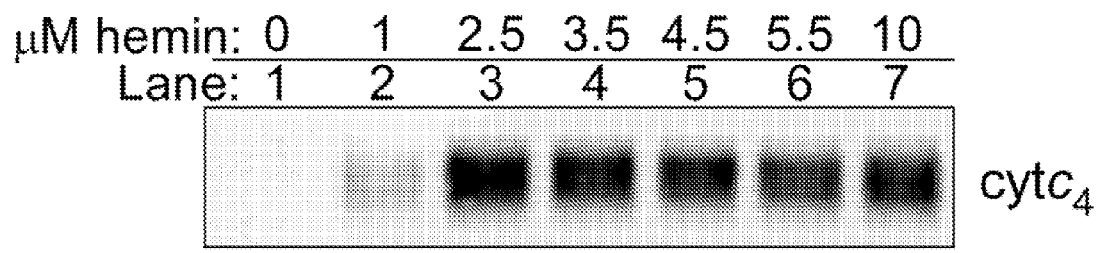
Figure 14:
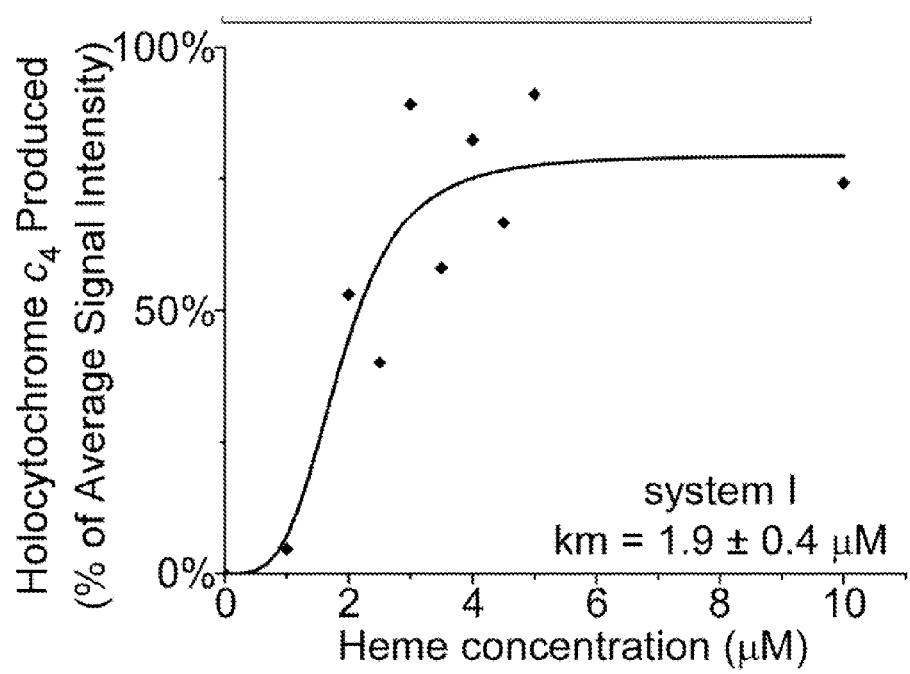
Figure 14:
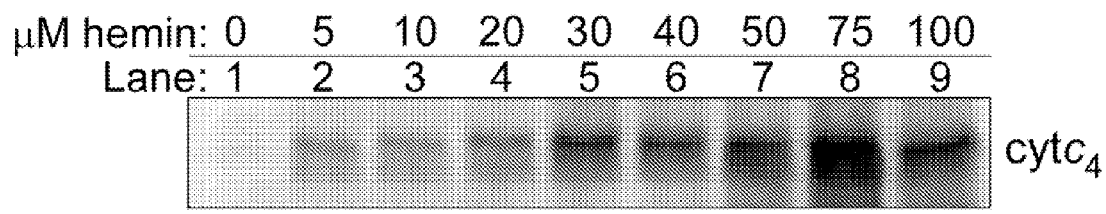
Figure 14:
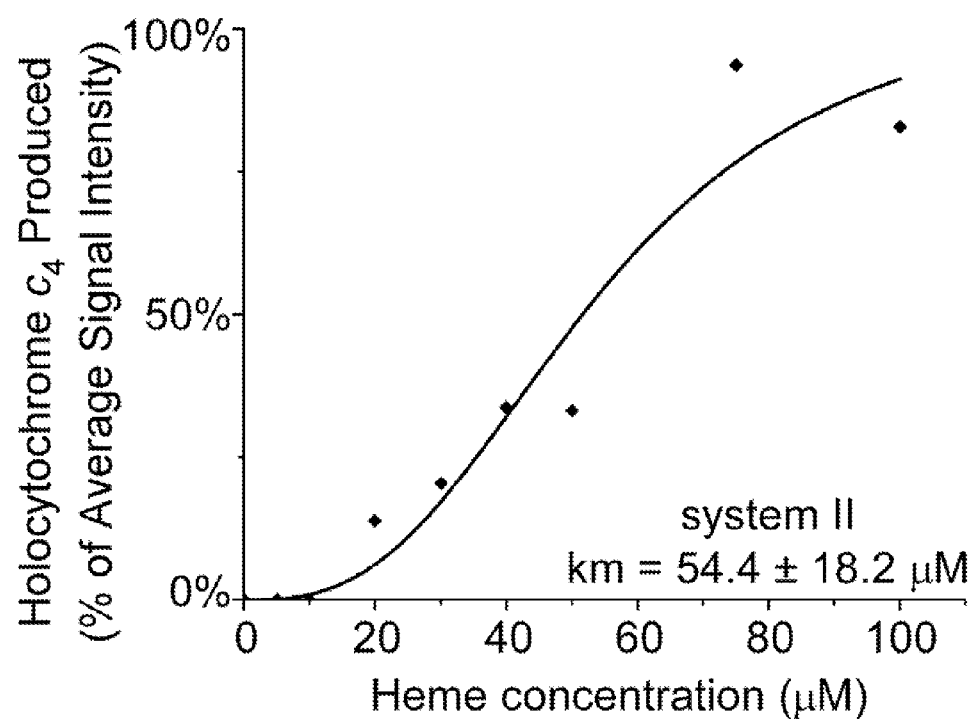

FIG. 14. Exogenous heme acquisition profiles for system I and system II. An *E. coli* heme auxotroph (RK105) containing pRGK333 or pRGK334, pRGK332, and pHPEX2 (outer membrane heme porin) were grown in the absence of ALA to exhaust intracellular ALA levels (therefore limiting heme to exogenously added heme). Exogenous heme was added to the culture media after 2.5 hours (0 to 10 mM for system 1 and 0 to 100 mM for system II) prior to induction of cytochrome $c_4$:6xHis (0.2% arabinose). Holocytochrome C4 was purified from B-PER extracted protein via nickel affinity chromatography, and separated via SDS-PAGE. Heme stains of holocytochrome $c_4$ from representative trials with system I (A) and system II (C). Curve fits to average heme stain intensity as a percentage of maximum signal intensity with respect to heme concentration is shown in (B) for system I (n=4) and (D) for system II (n=3).

Figure 15:
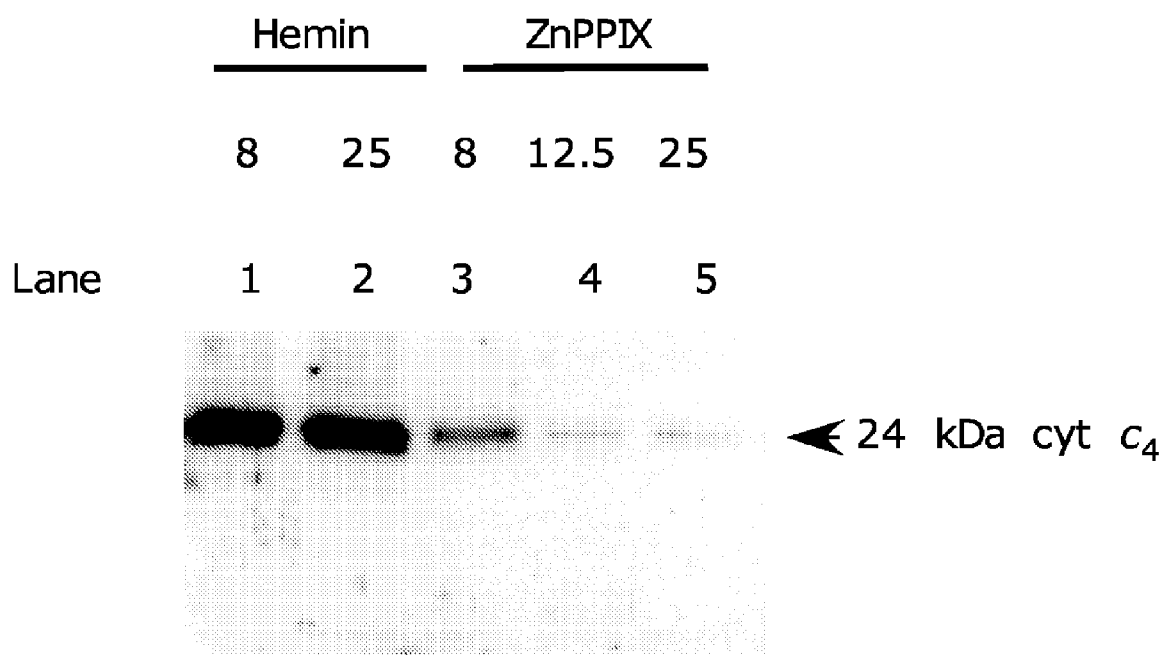

FIG. 15. Heme stain of holocytochrome $c_4$:6xHis with increasing concentrations of ZnPPIX. *E. coli* DccmDhemA (RK105) containing pRGK333, pRGK332, and pHPEX2 were grown in 8 mM heme (Lanes 1, 3-5) or 25 mM heme (Lane 2) to an OD600 of approximately 0.5. ZnPPIX was added (Lanes 3-5) and 1 mM IPTG to induce synthesis of the system I proteins. Incubation continued for one hour and 0.2% arabinose was added for three hours to induce the synthesis of the cytochrome c4. The concentrations (in mM) of heme and ZnPPIX are given above each lane. Above the panel pSysI is pRGK333 and pc4:6xHis is pRGK332.

Figure 16:
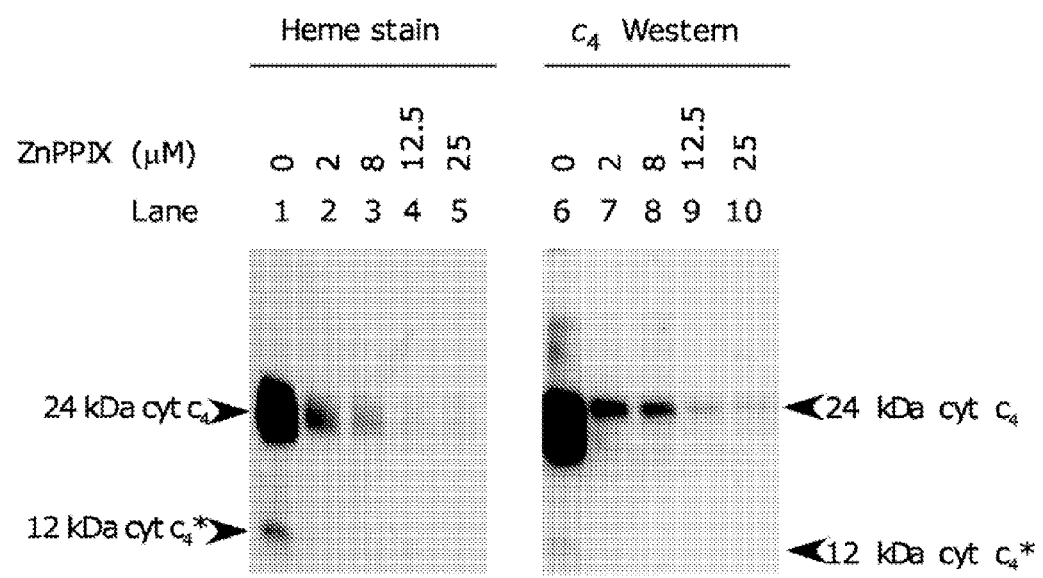
Figure 16:
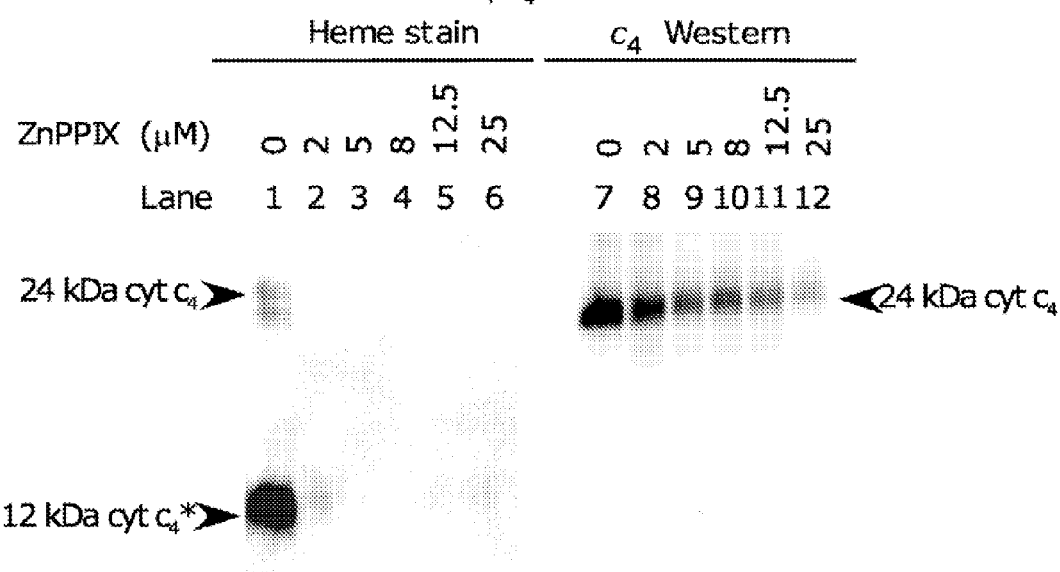

FIG. 16. Heme stains and western blots for detection of holocytochrome $c_4$ synthesis. *E. coli* Dccm, containing either (A) pRGK333, pRGK332, and pHPEX2 or (B) pRGK348 and pRGK332, were grown and 1 mM IPTG and ZnPPIX were added and growth continued for one hour. The cytochrome $c_4$:6xHis was induced with 0.2% arabinose for three hours and soluble B-PER protein extracts were prepared. The concentrations (in mM) of ZnPPIX are given above each lane. Above the panel pSysI is pRGK333, pSysII-chuA is pRGK348, pc4:6xHis is pRGK332 and Dccm is *E. coli* Dccm.

Figure 17:
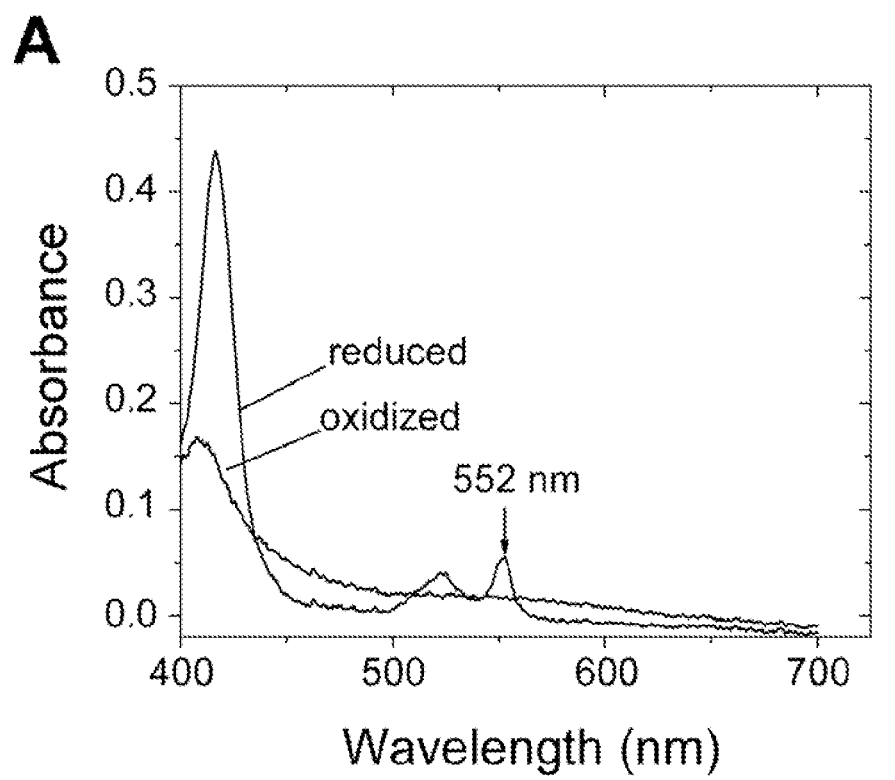
Figure 17:
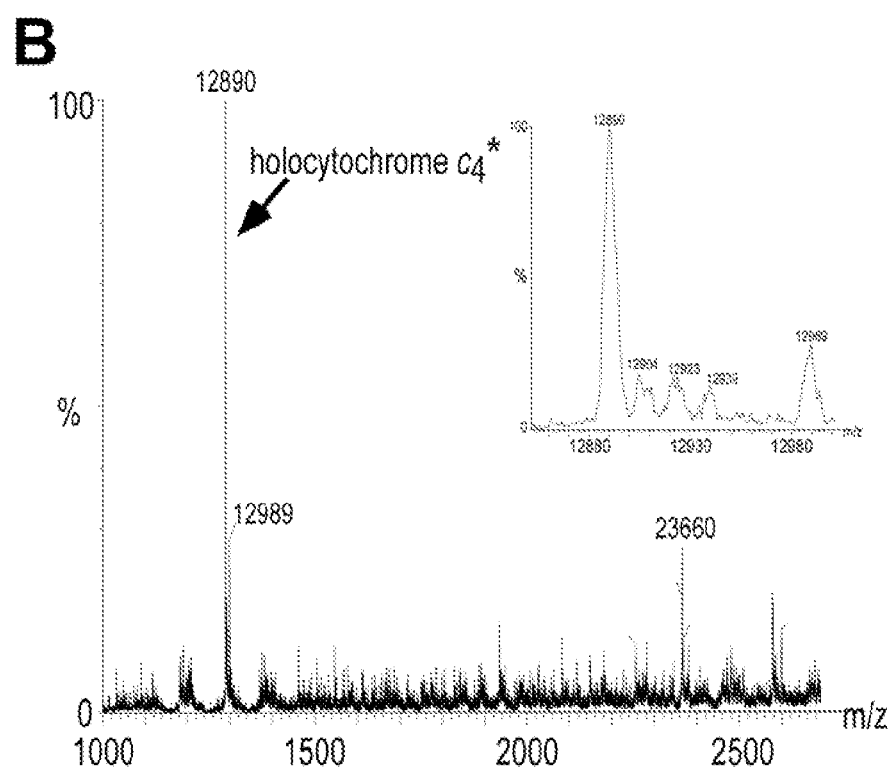

FIG. 17. Reduced-oxidized absorption spectra and ESI-MS analysis of cytochrome $c_4$. Overnight cultures of *E. coli* Dccm containing pRGK333, pRGK332, and pHPEX2 were diluted into fresh LB broth and grown to mid-log phase. ZnPPIX (8 mM) and IPTG (1 mM) were added and incubation continued for an additional hour. Arabinose (0.2%) was added for three hours to induce synthesis of cytochrome $c_4$:6×His and soluble B-PER extracts were prepared. (A) Reduced (sodium hydrosulphite) and oxidized (ammonium persulfate) absorption spectra and (B) ESI-MS analysis.

Figure 18:
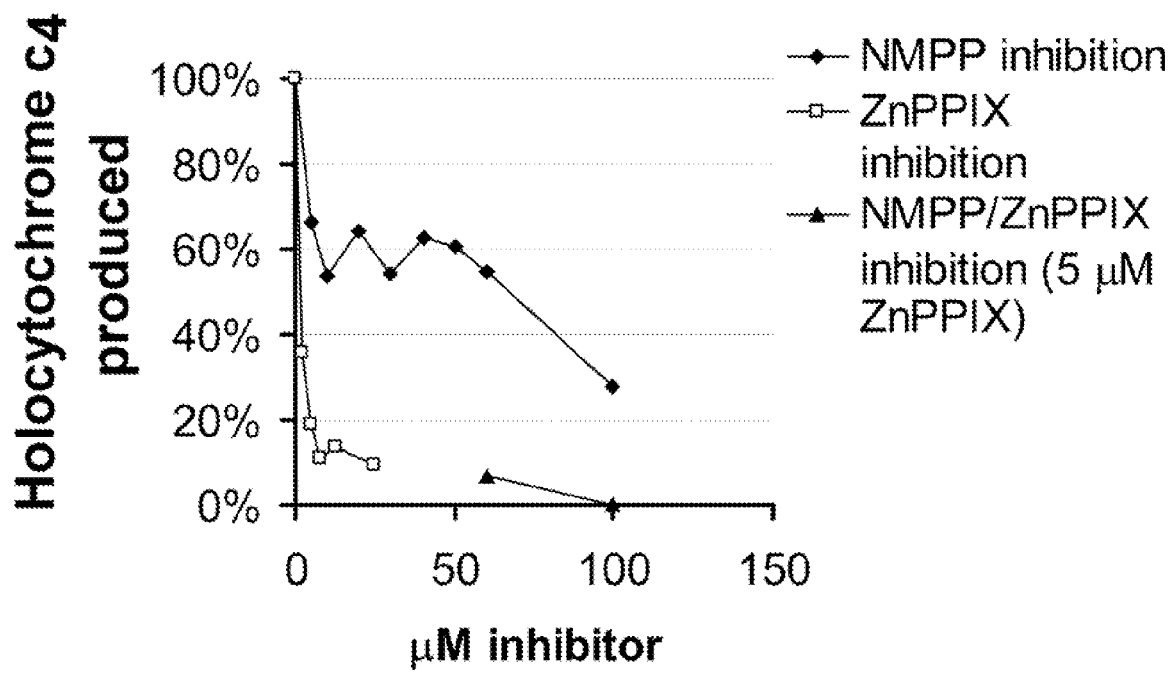

FIG. 18. Holocytochrome $c_4$ synthesis in the presence of ZnPPIX and NMPP. Overnight cultures of *E. coli* Dccm containing pRGK333, pRGK332, and pHPEX2 were diluted into fresh LB broth and grown to mid-log phase. NMPP (60 mM and 100 mM) and IPTG (1 mM) was added to separate cultures and incubation continued for 30 minutes. ZnPPIX (5 mM and 12.5 mM) was then added and incubation continued for an additional 30 minutes. Arabinose (0.2%) was added for three hours to induce synthesis of cytochrome $c_4$:6×His. Independent (NMPP and ZnPPIX) inhibition experiments were also performed. Holocytochrome c4 quantitation by heme stains intensity (in arbitrary units) from three independent trials.

Figure 19:
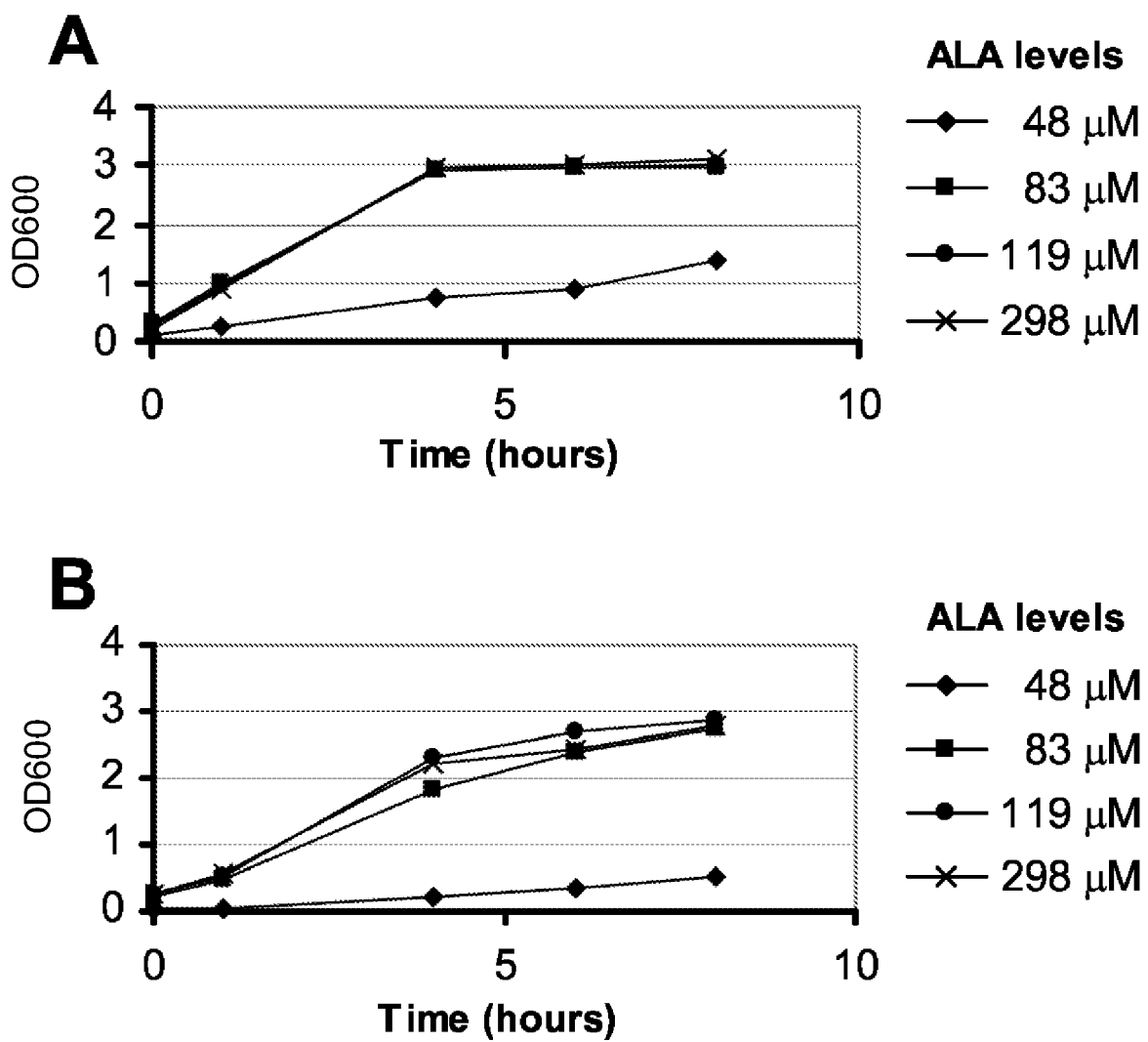

FIG. 19. Growth of *E. coli* DccmDhemA (RK 104) on ALA. Overnight cultures of *E. coli* DccmDhemA containing (A) pRGK333 (system I) or (B) pRGK334 (system II) were diluted into LB broth without ALA. The cultures were grown for two and one-half hours at 37° C. with aeration and ALA was added (time=0) at the indicated concentrations, with growth (A600) measured at OD600.

Figure 20:
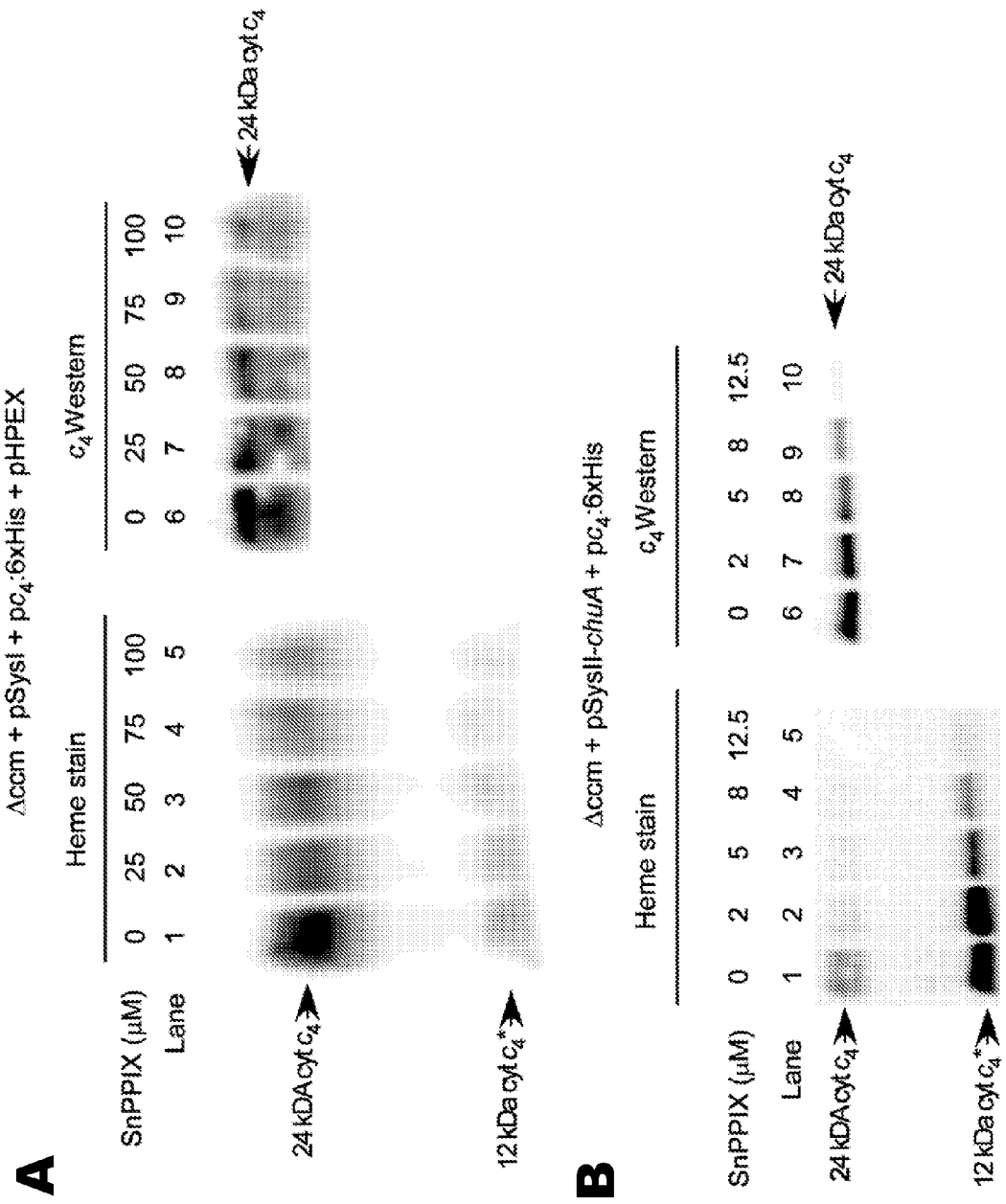

FIG. 20. Heme stain (lanes 1-6) and Western blot (lanes 7-12) indicating SnPPIX inhibits system II holocytochrome $c_4$:6×His synthesis and is not incorporated into cytochrome $c_4$ by system II. *E. Coli* Dccm, containing either (A) pRGK333, pRGK332, and pHPEX2 or (B) pRGK348 and pRGK332 were grown and 1 mM IPTG and SnPPIX were added and growth continued for one hour. The cytochrome $c_4$:6×His was induced with 0.2% arabinose for three hours and soluble B-PER protein extracts were prepared. The concentrations (in mM) of SnPPIX are given above each lane. Above the panel pSysII-chuA is pRGK248, pc4:His is pRGK332 and Dccm is *E. Coli* Dccm.

Figure 21:
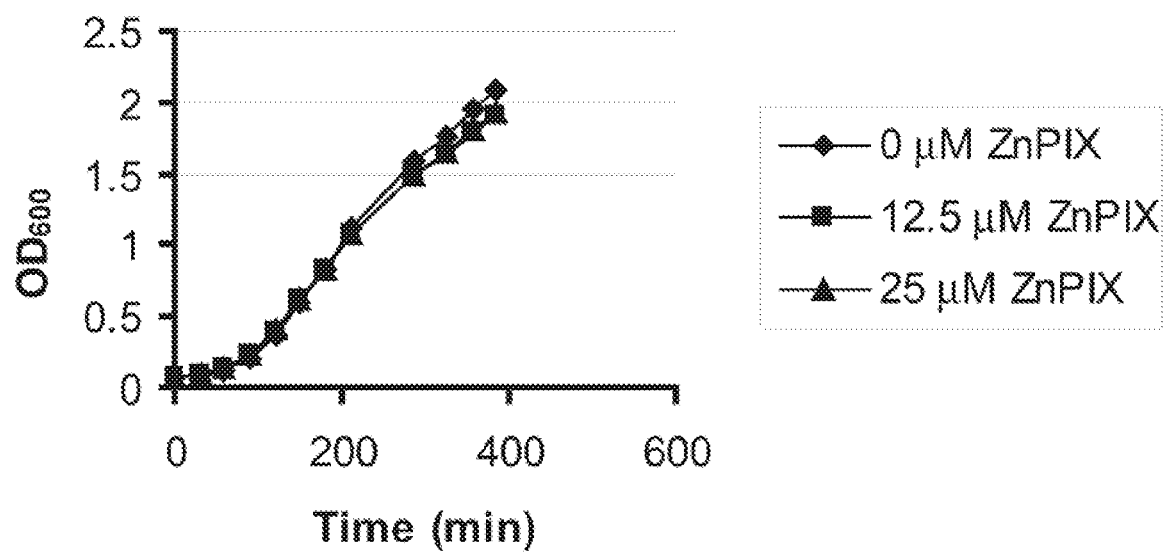

FIG. 21. Growth of *E. Coli* Dccm containing pRGK333, pRGK332, and HPEX2 in the presence of ZnPPIX. Overnight cultures of *E. Coli* Dccm containing pRGK333 (system I), pRGK332 (cytochrome $c_4$:6×His), and pHPEX2 were diluted into fresh LB broth containing the indicated ZnPPIX (in mM) concentrations for growth measurements.

FIG. 22. Western blot (A: lanes 1-7) and heme stain (B: lanes 1-5) indicating ZnPPIX competes with heme. Overnight cultures of *E. Coli* Dccm containing pRGK333, pRGK331, and pHPEX2 were diluted into fresh LB broth containing 12.5 mM ZnPPIX and grown to mid-log phase. IPTG (1 mM) was added and incubation continued for 30 minutes. Heme was added and incubation continued for 30 minutes. Arabinose (0.2%) was added for three hours to induce synthesis of cytochrome $c_4$:PhoA and soluble B-PER protein extracts were prepared. The concentrations (in mM) of ZnPPIX and heme are given above each lane. Above the panel psysI is pRGK333, pc4:PhoA is cytochrome $c_4$:PhoA, and Dccm is *E. Coli* Dcam.

FIG. 23 96 well screen using whole *E. Coli* cells induced with arabinose and pipetted into white microtiter plates (rows 1-9). ECL reagent (100 μl of Pierce ELISA femto) was injected, plate shaken for 1 minute, incubated for 4 minutes at room temperature, then relative luminescent units (RLU) were read for 10 sec/well in a Luminoscan (Thermo). (RLUs were stable for at least 20 minutes; a 2 sec/well read yielded similar results. No false positives or negatives were observed in this trial. Rows A-H in each of the columns 1-10 represent replicates of the experimental conditions for each respective column. Column 11, rows A-H contain decreasing amounts of pure cytochrome $c_4$ with row A, 2.1 ng; B, 1.1 ng; C, 0.6 ng; D, 0.2 ng, and E-H, <0.2 ng. Rows A-H in column 12 contain replicates of the experimental conditions for each respective column.

Figure 24:
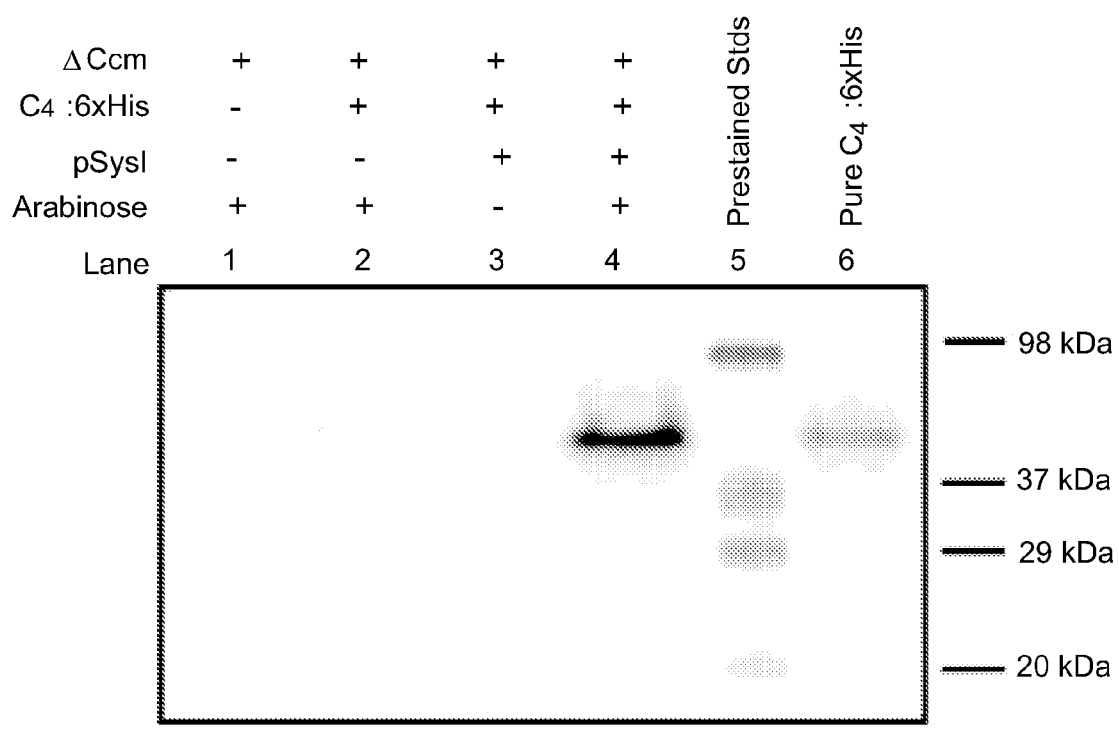

FIG. 24. Evidence that the ECL signal from whole cells was emanating from the cytochrome $C_4$. LB cultures of the indicated strains and conditions were sonicated and extracts (15 ml) were separated in a native polyacrylamide gel, and ECL-heme stained. The cytochrome $c_4$ runs at 50 KDalton in these gels, consistent with the fact that it has been crystallized as the dimer.

DETAILED DESCRIPTION

Figure 1:
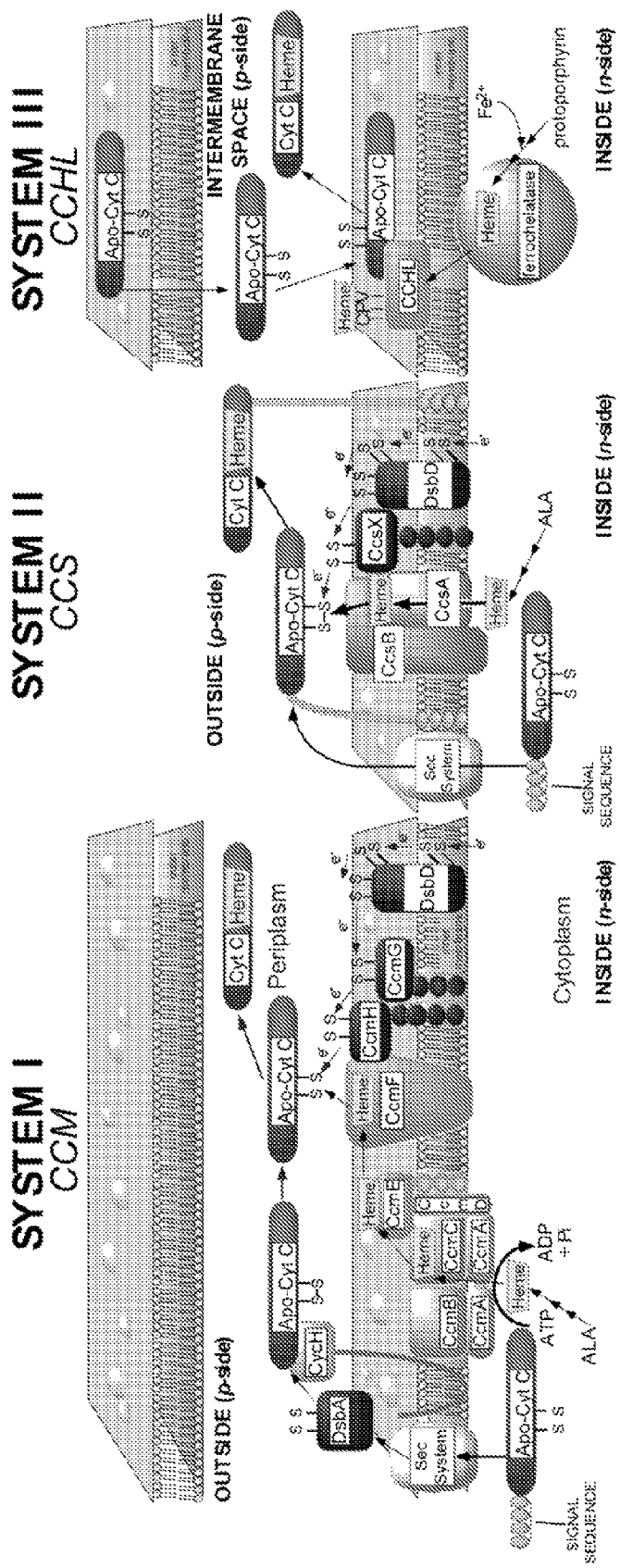
FIG. 1. Working models of the three pathways for cytochrome c biogenesis. Representative organisms that possess each system are listed below.

A method for identifying a compound that inhibits the synthesis of cytochrome c in bacteria is provided herein. In general, cytochrome c proteins are essential proteins that function as electron carriers in respiration in nearly all cells (and photosynthesis in some cells). Cytochrome c proteins function outside the cytoplasmic membrane in prokaryotes, in the intermembrane space of mitochondria, and in the lumen of chloroplasts. C-type cytochromes are generally characterized by a covalent attachment of heme (iron protoporphyrin IX) to the apoprotein via thioether bonds. Three distinct pathways exist for the synthesis of cytochrome c (FIG. 1). System I is found primarily in alpha proteobacteria and gamma proteobacteria; system II operates mainly in Gram-positive bacteria, beta proteobacteria, epsilon proteobacteria, and plant chloroplasts; and system III is limited to the mitochondria of certain eukaryotes. System I has eight or nine proteins, called the Ccm proteins; system II has four proteins, the Ccs proteins, and system III consists of a single protein. Generally, the function of most of the proteins of the system I and II pathways is to help shuttle heme through the cytoplasmic membrane or help link heme to the cytochrome c apoprotein. Compounds that inhibit the synthesis of cytochrome c may be effective antibiotic agents.

I. Compositions a) Bacterial Cells

One aspect of the invention provides an engineered bacterial cell in which the chromosomal region encoding the system I Ccm proteins is disrupted or deleted (i.e., Δccm). The nucleotide sequence encoding the Ccm proteins is sometimes a contiguous sequence (i.e., the ccm operon in *E. coli*). As will be appreciated by one skilled in the art, the chromosomal region encoding the Ccm proteins may be disrupted or deleted by a variety of methods. (For example, see Ausubel et al. (2003) Current Protocols in Molecular Biology, John Wiley & Sons, New York N.Y., ch. 1.) Suitable methods include transposon-mediated mutagenesis, retargeted group II introns, insertion of an antibiotic-resistance cassette, site-specific recombination, or a combination thereof. Examples of suitable transposons include Tn3, Tn5, Tn9, Tn10, Tn903, Tn1681, Mu, and miniMu. Suitable antibiotic-resistance cassettes include ampicillin-resistance, chloramphenicol-resistance, kanamycin-resistance, spectinomycin-resistance, and tetracycline-resistance cassettes. Suitable examples of site-specific recombination systems include the Flp/FRT system from *Schizosaccharomyces cerevisiae*, the Cre/loxP system from *E. Coli* bacteriophage P1, the R/RS system from *Zygosaccharomyces rouxii*, the φC31/attB,attP system from *Streptomyces* phage phiC31, and the mutant Gin/gix system from enteric bacteriophage Mu. In a preferred embodiment, the nucleotide sequence encoding the Ccm proteins may be deleted and replaced with an antibiotic-resistance cassette using PCR-based techniques well known in the art (and detailed in the examples).

The bacterial cell may further comprise a deletion of the chromosomal region encoding the HemA protein (i.e., ΔhemA). HemA is an amino levulinic acid (ALA) synthetase, which is the first enzyme in the heme biosynthesis pathway. The nucleotide sequence encoding HemA may be disrupted or deleted using any of the aforementioned methods. It should be noted that other enzymes in the heme biosynthesis pathway may be inactivated by nucleotide sequence deletion or disruption without departing from the scope of the invention.

The bacterial cell may be an alpha proteobacterial cell or a gamma proteobacterial cell (i.e., a cell containing a system I pathway). Alpha proteobacteria include Caulobacterales (e.g., *Caulobacter*), Parvularculales, Rhizobiales, Rhodobacterales, Rhodospirillales (e.g., *Acetobacter*), Rickettsiales, and Sphingomonadales. Gamma proteobacteria include Acidithiobacillales, Aeromonadales (e.g., *Aeromonas*), Alteromonadales, Cardiobacteriales, Chromatiales, Enterobacteriales (e.g., *Escherichia*), Legionellales, Methylococcales, Pasteurellales (e.g., *Haemophilus*), Pseudomonadales (e.g., *Pseudomonas*), Vibrionales (e.g., *Vibrio*), and Xanthomonadales. In one embodiment, the bacterial cell may be *Bradyrhizobium japonicum* in which the nucleotide sequence encoding the CcmA-H proteins is disrupted or deleted. In another embodiment, the bacterial cell may be *Paracoccus denitrificans* in which the nucleotide sequence encoding the CcmA-H proteins is disrupted or deleted. In yet another embodiment, the bacterial cell may be *Rhodobacter capsulatus* in which the nucleotide sequence encoding the CcmA-H proteins is disrupted or deleted. In still another embodiment, the bacterial cell may be *Escherichia Coli* in which the nucleotide sequence encoding the CcmA-H proteins is disrupted or deleted. In an alternate embodiment, the bacterial cell may be *R. capsulatus* in which the nucleotide sequence encoding the CcmA-H proteins and the nucleotide sequence encoding the HemA protein are deleted (ΔccmΔhemA). In a preferred embodiment, the bacterial cell may be a Δccm *E. Coli* cell. In another embodiment, the bacterial cell may be a ΔccmΔhemA *E. Coli* cell. One skilled in the art will appreciate that a Δccm bacterial cell cannot synthesize cytochrome c and a ΔhemA bacterial cell can grow only in the presence of exogenous ALA.

b) Cytochrome c Pathway Constructs

Another aspect of the invention provides constructs for the delivery and expression of the cytochrome c biosynthesis enzymes in a Δccm bacterial cell. The construct may comprise a nucleotide sequence encoding the Ccm proteins of system I, or the construct may comprise a nucleotide sequence encoding the Ccs proteins of system II.

The nucleotide sequence encoding Ccm proteins or Ccs proteins may be isolated by PCR amplification or other techniques well known in the art. (See the examples and also Ausubel et al. (2003) Current Protocols in Molecular Biology, John Wiley & Sons, New York N.Y., ch. 3 and 6.). As noted in section I (a), the nucleic acid encoding the system I Ccm proteins may be from an alpha proteobacterium or a gamma proteobacterium. In one embodiment, the nucleic acid sequence encoding the CcmA-H proteins of *R. capsulatus* may be isolated. In a preferred embodiment, the nucleic acid sequence encoding the CcmA-H proteins of *E. coli* may be isolated. Although the system II pathway includes four proteins, it appears that two proteins, CcsA and CcsB, may be may be sufficient to restore cytochrome c biosynthesis in a heterologous host cell. The nucleic acid sequence encoding the Ccs proteins may be from a beta proteobacterium, an epsilon proteobacterium, a Gram-positive bacterium, or a cyanobacterium. Suitable beta proteobacteria include Burkholderiales (e.g., *Bordetella*), Hydrogenophilales, Methylophilales, Neisseriales, Nitrosomonadales, Rhodocyclales, and Procabacteriales. Suitable epsilon proteobacteria include Campylobacterales (e.g., *Helicobacter*) and Nautiliales. Suitable gram-positive bacteria include *Bacillus, Listeria, Enterococcus, Mollicutes*, and *Mycobacterium tuberculosis*. Suitable cyanobacteria include *Synechocystis, Nostoc, Anabaena*, and *Gloeocapsa*. In one embodiment, the nucleic acid sequence encoding the CcsA and CcsB proteins of *Bacillus subtilis* may be isolated. In another embodiment, the nucleic acid sequence encoding the CcsA and CcsB proteins of *Bordetella pertussis* may be isolated. In yet another embodiment, the nucleic acid sequence encoding the fused CcsBA protein of *Helicobacter* species may be isolated. In a preferred embodiment, the nucleic acid sequence encoding the fused CcsBA protein of *H. pylori* may be isolated The isolated nucleic acid is typically cloned into an appropriate expression vector so that the proteins may be expressed in the bacterial cell from section I (a). An expression vector is typically a vector that contains the necessary elements for transcriptional and translational control of the inserted nucleic acid sequence in the host cell. The vector may be a plasmid vector, a Lambda bacteriophage vector, a Lambda-derived vector, or a filamentous phage-derived vector. In one embodiment, the vector may be a plasmid. In one embodiment, the vector may be a pGEX-derived plasmid. In another embodiment, the vector may be a pBAD-derived plasmid.

The nucleotide sequence encoding the Ccm or Ccs proteins is generally operably linked to an inducible promoter so that the timing of expression may be controlled. Suitable examples of inducible promoters include, but are not limited to, those induced by expression of an exogenous protein (e.g., T7 RNA polymerase, SP6 RNA polymerase), presence of a small molecule (e.g., IPTG, arabinose, galactose, tetracycline, steroid hormone, abscisic acid), metals (e.g., copper, zinc, cadmium), and environmental factors (e.g., heat, cold, stress). The type of promoter can and will vary depending upon other constructs that may be used. In one embodiment, the promoter may be induced by IPTG. Suitable examples of IPTG-inducible promoters include the TAC, lac, lacUV5, and trc promoters. In another embodiment, the promoter may be induced by arabinose. Suitable arabinose-inducible promoters include araB, araBAD, and araFG.

The vector typically also comprises a selectable marker, which is a sequence that codes for a protein that provides resistance to an antibiotic. Suitable selectable markers include those that provide resistance to ampicillin, carbenacillin, chloramphenicol, kanamycin, spectinomyin, and tetracycline. The choice of selectable marker can and will vary depending upon other features of the bacterial cell and other constructs that may be used. Methods well known to those skilled in the art may be used to construct the expression vectors. (See Ausubel et al. (2003) Current Protocols in Molecular Biology, John Wiley & Sons, New York N.Y., ch. 1, 3 and 16).

c) Cytochrome c Reporter Constructs

The invention also provides cytochrome c reporter constructs, which facilitate monitoring of the synthesis of cytochrome c in the recombinant cells (i.e., a ΔccmΔhemA or Δccm bacterial cell transfected with a Ccm or a Ccs expression vector). Typically, the cytochrome c reporter will produce a protein of a different size or different immunogenicity than the endogenous cytochrome c of the host bacterial cell.

In one embodiment, the cytochrome c protein may be the cytochrome $c_4$ protein of *Bordetella pertussis*. In another embodiment, the cytochrome c protein may be the cytochrome $c_2$ protein of *R. capsulatus*.

Additionally, the reporter protein may be a fusion of the cytochrome c protein and another protein. Typically the fusion partner protein has a variety of research tools available for its detection or purification. The fusion partner protein may be alkaline phosphatase (AP), glutathione-S-transferase (GST), maltose binding protein (MBP), luciferase, a 6×His tag, a myc tag, or a Flag tag. In one embodiment, the cytochrome c reporter may be a cytochrome $c_4$:alkaline phosphatase fusion protein. In another embodiment, the cytochrome c reporter may be a cytochrome $c_4$:6×His fusion protein. In yet another embodiment, the cytochrome c reporter may be a cytochrome $c_4$:Flag tag fusion protein In general, the cytochrome c reporter construct will be an expression vector with an inducible promoter and a selectable marker, as detailed in section I (b) and may be constructed using procedures well known in the art, as mentioned above.

II. Methods of Screening for a Compound that Inhibits the Synthesis of Cytochrome c in Bacteria Another aspect of the invention provides methods for identifying compounds that inhibit the synthesis of cytochrome c in a bacterial cell. Using the deletion mutant cells described in section I (a) and the expression constructs described in sections I (b) and (c), compounds have been and may be identified that inhibit the synthesis of cytochrome c. In general, these inhibitors block one of the steps of the system I or system II cytochrome c synthesis pathways, but will not affect the eukaryotic system III pathway. Furthermore, since cytochrome c synthesis occurs on the outer surface of the cytoplasmic membrane of bacteria, cytochrome c biosynthesis is a readily accessible target for an antibacterial agent.

The method comprises transfecting a Δccm bacterial cell with an inducible Ccm expression vector (provides system I proteins) or an inducible Ccs expression vector (provides system II proteins), as well as an inducible cytochrome c reporter vector. In some embodiments, the Δccm bacterial cell may further comprise ΔhemA. A variety of methods are suitable for introducing an expression vector into a bacterial cell. The bacterial cell may be transfected with the expression vector by a heat shock. The bacterial cell may be transfected with the expression vector by high-voltage electroporation. Methods to make bacterial cells competent to take up vectors are well known in the art.

The Δccm bacterial cell may further comprise a porphyrin porin expression vector. Expression of a porin protein may permit passage of a metalloporphyrin, such as heme (iron protoporphyrin IX) through the outer membrane of the bacterial cell. In one embodiment, the porphyrin porin may be ChuA, a heme receptor from *Escherichia coli*. In another embodiment, the porphyrin porin may be a porin from *Bartonella quintanta*. It should be noted that porphyrin porins from other bacteria may be used without departing from the scope of the invention. One skilled in the art will appreciate that a Δccm bacterial cell harboring a Ccm or a Ccs expression vector and a porphyrin porin expression vector will typically grow only in the presence of exogenous heme.

The method further comprises contacting the aforementioned transfected bacterial cell with a test compound. "Contacting" typically entails growing the cell in the presence of the compound upon induction of the various expression constructs. Methods are well known in the art for growing bacterial cells in appropriate culture media under optimal growth conditions in the presence of the appropriate antibiotics and other compounds (e.g., ALA, inducers). The timing of induction of the various expression constructs can and will vary depending upon the compound being screened.

The method further comprises determining the amount of cytochrome c reporter protein produced in the presence of the compound relative to the amount of reporter protein produced in the absence of the compound. A decrease in amount of cytochrome c reporter protein is an indication that the compound inhibits the synthesis of cytochrome c. The amount of cytochrome c reporter protein produced by the cell may be measured in an extract of the cell. Alternatively, the cytochrome c reporter protein may be partially purified from the cell extract before the amount is measured. Various methods are known in the art for purifying proteins from crude cell extracts. A preferred method includes affinity chromatography, in which the fusion partner of cytochrome c is utilized to capture the entire reporter fusion protein. Typically, a solid support medium containing a specific compound is used to bind the fusion partner of the reporter protein. Suitable examples include glutathione-linked beads that bind GST, maltose-linked beads that bind MBP, $Ni^{2+}$ beads that bind 6×His tags, anti-Flag antibody-linked beads that bind Flag tags, and anti-AP antibody-linked beads that bind AP.

A variety of methods may be used to detect the cytochrome c reporter protein. The detection method may include gel electrophoresis, immunodetection, heme staining, or a combination thereof. In one embodiment, the cytochrome c reporter protein may be resolved by SDS-polyacrylamide gel electrophoresis. The polyacrylamide gel may then be stained for heme groups using a colorimetric stain, such as o-dianisidine or dimethoxy benzidine. Alternatively, the polyacrylamide gel may be stained for heme groups using a chemiluminescent substrate. The polyacrylamide gel may be blotted and probed with an antibody against a part of the cytochrome c reporter protein. The antibody may recognize one or more epitopes of the cytochrome c protein or the fusion partner protein. As described in section I (c), the fusion partner may be alkaline phosphatase (AP), glutathione-S-transferase (GST), maltose binding protein (MBP), luciferase, a 6×His tag, a myc tag, or a Flag tag. In another embodiment, the heme of the cytochrome c reporter protein may be detected in solution using a chemiluminescent substrate. The emission of chemiluminescent product may be measured using a luminometer. In yet another embodiment, the cytochrome c reporter protein may be detected using mass spectrometry.

A variety of compounds may be screened using this method. Suitable test compounds include, but are not limited to, metalloporphyrins. Suitable metalloporphyrins include zinc protoporphyrin IX, tin protoporphyrin IX, manganese protoporphyrin IX, cobalt protoporphyrin IX, aluminum protoporphyrin IX, copper protoporphyrin IX, chromium protoporphyrin IX, palladium protoporphyrin IX, platinum protoporphyrin IX, and vanadium protoporphyrin IX. The test compound may be N-methylprotoporphyrin or a derivative or analog of N-methylprotoporphyrin. The test compound may be a modified heme that possesses only one of the two vinyl groups, i.e., the 2-vinyl group or the 4-vinyl group. The test compound may be a modified heme in which the 6-propionate group has been modified. As an example, the 6-propionate group may be converted to a carboxyamide. All of the modified heme analogs may possess iron or any of the aforementioned metals.

In a preferred embodiment, the screening method comprises a Δccm *E. Coli* cell transfected with a first expression plasmid encoding the CcmA-H proteins of *E. Coli* or the fused CcsBA protein of *H. pylori* and a second expression plasmid encoding cytochrome c reporter protein. The cytochrome c reporter second plasmid encodes a cytochrome $c_4$:alkaline phosphatase fusion protein or a cytochrome $c_4$:6× His fusion protein, wherein the cytochrome $c_4$ protein is from *B. pertussis*. The coding region of the first plasmid is operably linked to an IPTG-inducible promoter and the coding region of the second plasmid is operably linked to an arabinose-inducible promoter. The amount of cytochrome c reporter protein may be measured in cell extracts using a chemiluminescent substrate and a luminometer. In general, this system will identify compounds that inhibit cytochrome c synthesis, as well as compounds that inhibit heme synthesis. The Δccm *E. Coli* cell may further comprise a porphyrin porin expression plasmid. The porphyrin porin may be ChuA, a heme receptor from *E. Coli*. Since the cells of this later system require exogenous heme, the compounds identified in this system generally will be inhibitors of cytochrome c synthesis.

III. Kits for Screening for a Compound that Inhibits the Synthesis of Cytochrome c A further aspect of this invention is the provision of kits for identifying inhibitors of the synthesis of cytochrome c in bacterial cells. A kit comprises a strain of Δccm *E. Coli* cells transfected with a first expression plasmid vector encoding the CcmA-H proteins of *E. Coli* or the fused CcsBA protein of *H. pylori* and a second expression plasmid encoding a cytochrome c reporter protein. The cytochrome c reporter protein is either cytochrome $c_4$:alkaline phosphatase fusion protein or a cytochrome $c_4$:6×His fusion protein, wherein the cytochrome c4 protein is from *B. pertussis*. The coding region of each expression plasmid is operably linked to an inducible promoter, whereby expression of the first plasmid is controlled by IPTG and expression of the second plasmid is controlled by arabinose. The Δccm *E. Coli* cells of the kit may further comprise an exogenous porphyrin porin. Also provided in the kits are instructions for growing the cells and for contacting the cells with a compound to be screened. A kit may also comprise means for measuring the production of the cytochrome c reporter protein produced in the absence or the presence of a test compound, as described in section II.

IV. Methods of Treatment

The invention also provides a method for treating a subject having a bacterial infection. The method comprises administering to the subject an effective amount of a cytochrome c synthesis inhibitor. In general, the cytochrome c synthesis inhibitors identified using the methods of this invention will inhibit the synthesis of cytochrome c in bacterial cells, but will not affect the synthesis of cytochrome c in eukaryotic cells.

Bacterial cells in which the synthesis of cytochrome c may be inhibited include any organism with a system I pathway (e.g., alpha and gamma proteobacteria) or a system II pathway (e.g., beta and epsilon proteobacteria and most Gram-positive bacteria). In particular, bacteria that may be inhibited include *Bacteroides* species, *Bartonella* species, *Brucella* species, *Camphylobacter* species, *Haemophilus* species, *Helicobacter* species, *Mycobacterium tuberculosis*, *Neisseria* species, *Porphyromonas* species, *Pseudomonas aeruginosa*, *Rickettsiae* species, *Salmonella* species, *Vibrio* species, and *Yersinia* species. Diseases caused by these bacteria include tuberculosis, nosocomial diseases, rickettsiae diseases, ulcers, food poisonings, abcesses, sinusitis, and cystic fibrosis (via *Pseudomonas aeruginosa*).

Non-limiting examples of subjects that may be treated with a c synthesis inhibitor include humans, primates, cats, dogs, cattle, swine, poultry, sheep, horses, fish, research animals, and zoo animals.

The chemical nature of the cytochrome c synthesis inhibitor can and will vary. In one embodiment, the cytochrome c synthesis inhibitor may be N-methylprotoporphyrin.

In another embodiment, the cytochrome c synthesis inhibitor may be zinc protoporphyrin IX. In still another embodiment, the cytochrome c synthesis inhibitor may be tin protoporphyrin IX.

The cytochrome c synthesis inhibitor may be formulated into pharmaceutical compositions and administered by a number of different means that will deliver a therapeutically effective dose. Such compositions may be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols may be used. Mixtures of solvents and wetting agents such as those discussed above are also useful.

Solid dosage forms for oral administration may include capsules, tablets, pills, powders, and granules. In such solid dosage forms, the compound is ordinarily combined with one or more adjuvants appropriate to the indicated route of administration. If administered per os, the compound may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as can be provided in a dispersion of active compound in hydroxypropylmethyl cellulose. In the case of capsules, tablets, and pills, the dosage forms may also comprise buffering agents such as sodium citrate, or magnesium or calcium carbonate or bicarbonate. Tablets and pills can additionally be prepared with enteric coatings.

For therapeutic purposes, formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The amount of the cytochrome c synthesis inhibitor that is combined with the carrier materials to produce a single dosage of the composition can and will vary depending upon the patient and the particular mode of administration. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

DEFINITIONS

The term "heme" as used herein refers to a prosthetic group comprising an iron atom in the center of a large organic cyclic macromolecule called porphyrin. Specifically, the heme mentioned herein is a c-type heme, which is found in c-type cytochromes.

The term "metalloporphyrin" as used herein refers to a compound formed by the combination of a porphyrin with a suitable metal.

The term "porin" a used herein refers to a large transmembrane protein that forms a pore in a membrane through which small molecules may pass.

The term "protoporphyrin" or "protoporphyrin IX" as used herein refers to a mature porphyrin ring that has not complexed with a metal atom.

The terms "transfect" or "transfection" as used herein refers to the process during which a cell allows entry of nucleic acid molecules, which do not integrate in the host chromosome, but rather remain extrachromosomal.

As various changes could be made in the above constructs and methods without departing from the scope of the invention, it is intended that all matter contained in the above description and in the examples given below, shall be interpreted as illustrative and not in a limiting sense.

EXAMPLES

The following examples detail various iterations of the invention.

Cytochromes c proteins are electron transport proteins that are essential for aerobic and anaerobic respiration, as well as many other cellular processes, such as photosynthesis and apoptosis. Cytochromes c are distinguished from other cytochromes by a covalent ligation of the heme vinyl groups to the cysteine residues of apocytochrome c in a CXXCH motif, and are ubiquitous among all life.

Three distinct pathways for the synthesis of c-type cytochromes, called system I, II and III have been identified for various organisms. Systems I and II deliver heme to the site of assembly, maintain the apocytochrome c in a reduced state, and facilitate an energy independent, covalent ligation of the heme to the apocytochrome c. The system I pathway, which uses eight proteins encoded by the ccm genes, is found in α and γ proteobacteria, archaea, and plant mitochondria. The system II pathway, comprised of four proteins, is used by Gram-positive bacteria, β and ε proteobacteria, plant chloroplasts, and cyanobacteria. Four genes, called ccsB, ccsA, ccsX and dsbD (or its homologue ccdA) are involved in the system II pathway, but CcsB and CcsA proteins may be all that are necessary, other than a general thiol reductant, for the synthesis of c-type cytochromes via system II. Eukaryotes (yeast, invertebrates and vertebrates) utilize the system III pathway, comprised of a single soluble enzyme called cytochrome c heme lyase (CCHL), found in the mitochondria.

In the examples below, a heterologous recombinant approach in *Escherichia Coli* was employed. In Example 1, a cytochrome c reporter was engineered and inserted into *E. Coli*. All cytochrome c biogenesis genes were excised out of *E. Coli* and complemented by engineered system I or system II genes in Example 2. This recombinant *E. Coli* strain was used in Example 3 to compare the ability of system I and system II to deliver heme to the cytochrome c biosynthetic pathways. Example 4 further examined the heme delivery capability of system I by discovering the presence of a heme storage pool within the system I pathway proteins. The affinity for heme in systems I and II was compared in Example 5. Example 6 compared the ability of system I and II to utilize other non-ferrous metals such as copper, zinc, tin and manganese in the biogenesis of cytochromes c. Recombinant *E. Coli* was further used to discover and characterize the inhibitory properties of metalloporphyrin ZnPPIX on systems I and II cytochromes c biogenesis in Example 7. In Example 8, the techniques developed for the recombinant *E. Coli* strain may be optimized for microtiter plates to develop a method of high throughput screening for cytochrome c inhibitors.

Materials and Methods for Examples 1-8 a) Bacterial Growth Conditions

All *E. Coli* strains were grown aerobically at 37° C. in Luria-Bertani media (LB; Difco) with shaking at 300 rpm at 37° C. Antibiotics (Sigma-Aldrich; St. Louis, Mo.) were used at the following concentrations: carbenicillin 50 µg mL$^{-1}$, tetracycline 15 µg mL$^{-1}$, chloramphenicol 20 µg mL$^{-1}$, kanamycin 100 µg mL$^{-1}$, and ampicillin 100 µg mL$^{-1}$. Aminolevulinic acid (ALA; Sigma-Aldrich) was used at a concentration of 50 µg mL$^{-1}$ (300 µM), unless otherwise noted. Metalloporphyrins zinc (II) protoporphyrin IX (ZnPPIX), tin (IV) protoporphyrin IX (SnPPIX), manganese (III) protoporphyrin IX (MnPPIX), and cobalt (III) protoporphyrin IX (CoPPIX) were obtained from Frontier Scientific (Logan, Utah) and were dissolved in 0.1 N NaOH to 10 mg mL$^{-1}$ stock concentration. Hemin (heme; Frontier Scientific) was dissolved in 50% DMSO to 10 mg mL$^{-1}$ stock concentration.

b) Construction of RK103

A derivative of *E. coli* MG1655 with the eight ccm genes replaced by a kanamycin-resistance cassette (Δccm) was constructed by the procedure of Wanner and colleagues (Datsenko and Wanner, 2000). Polymerase chain reaction (PCR) products were generated by using a pair of primers, Δccm-left and Δccm-right, and a template plasmid, pKD4, bearing a kanamycin-resistance marker flanked by FLP recombinase target sites. All oligonucleotide primers used are shown in Table 1. The oligonucleotides include sequences identical to the C-terminal coding sequence of ccmH and the N-terminal coding sequence of ccmA, respectively, for targeting recombination events to the corresponding loci in the *E. coli* chromosome. The 3' end of the oligonucleotides incorporate the pKD4 priming sites P1 and P2 respectively. The PCR product was introduced into MG1655 cells expressing the phage λ Red recombinase encoded on pKD46. Transformants were selected on LB-kanamycin at 37° C. Several colonies that were resistant to kanamycin but sensitive to ampicillin (indicating a loss of pKD46) were screened by PCR with test primers flanking the recombination site to identify strains with a deletion at the locus.

c) Construction of E. coli Strain RK105

A derivative of the E. coli Δccm (RK103, see above) with the hemA gene replaced with a kanamycin resistance cassette was constructed by the procedure of Datsenko and Wanner (2000). PCR products were generated using a template plasmid, pKD4, containing a kanamycin resistance cassette that is flanked by FLP recombinase target sites, and a pair of oligonucleotide primers, ΔhemA-left and ΔhemA-right (see Table 1). The oligonucleotide primers included sequences identical to the N-terminal and C-terminal coding sequence, respectively, of hemA, for targeting recombination events to the corresponding loci in the E. coli chromosome. The 3' end of the oligonucleotides also incorporated the pKD4 priming sites P1 and P2, respectively. The PCR product was introduced into E. coli Δccm (RK 104), cured for kanamycin resistance, expressing the λ phage Red recombinase encoded on pKD46. Transformants were selected on LB with kanamycin and ALA at 37° C. Several colonies that were resistant to kanamycin but sensitive to ampicillin (indicating a loss of pKD46) were screened by PCR with oligonucleotide primers flanking the recombination site to identify strains with a deletion of the hemA gene.

d) Constructions of Plasmids

Escherichia coli strain TB1 was used as host for all clonings. pGex-4T-1 (Amersham Biosciences; Piscataway, N.J.) derived vectors have an N-terminal GST fusion to the insert under the control of the IPTG-inducible Tac promoter. All oligonucleotide primers used are shown in Table 1.

pRGK333 (system I plasmid, containing all eight ccmA-ccmH genes) was constructed by amplifying the entire 6.3 kb ccm locus by PCR with the oligonucleotides SysI-Nterm and SysI-Cterm. The amplified product was digested and ligated into the vector, pGEX-4T-1 digested with BamHI and EcoRI.

pRGK345 (ΔccmE), containing an in frame deletion of ccmE, was generated in a two step process that takes advantage of the overlapping stop and start codons between ccmD and ccmE, and between ccmE and ccmF. The coding region of ccmABCD was amplified by PCR with the oligonucleotides SysI-Nterm and CcmD-Cterm. The amplified product was digested and ligated into the vector, pGEX-4T-1 digested with BamHI and EcoRI. The resulting intermediate plasmid pRGK344 (pGexccmABCD) encodes CcmABCD with an N-terminal fusion to GST. Second, ccmFGH was amplified by PCR with the oligonucleotides CcmF-Nterm and SysI-Cterm. The amplified product was digested and ligated into the vector, pGexccmABCD digested with NdeI and EcoRI.

pRGK346 (ΔccmH), containing an in frame deletion of ccmH, was generated by amplifying the coding region of ccmABCDEFG by PCR with the oligonucleotides SysI-Nterm and CcmG-Cterm. The amplified product was digested and ligated into the vector, pGEX-4T-1 digested with BamHI and EcoRI.

For construction of an arabinose-inducible, chloramphenicol-resistant vector, pBAD24 (Khlebnikov et al., 2000) was used as a template with the oligonucleotides pBad24-left and pBad24-right. The amplified product was cut with HinDIII and ligated with the chloramphenicol-resistance cassette cut from pHP45 ΩCmr (Alexeyev et al., 1995) using HinDIII to generate pRGK330 (with Cmr). The cycC:phoA fusion gene was PCR amplified using pRGK323 (Beckett et al., 2000) as a template with the oligonucleotides $c_4$-pho-Nterm and $c_4$-pho-Cterm. The amplified reporter cassette was digested with NheI and Acc651 and ligated into the pRGK330 multiple cloning site to generate pRGK331 ($c_4$:Pho).

For construction of a cytochrome $c_4$:hexahistidine reporter, the B. pertussis cycC gene was PCR amplified from pRGK323 with the oligonucleotides $c_4$-pho-Nterm and $c_4$-6× His-Cterm to add a C-terminal 6×His tag to the reporter. The amplified product was digested with NheI and Acc651 and ligated into pRGK330 to generate pRGK332($c_4$:His).

For construction of a plasmid expressing system II, the H. pylori ccsBA coding region was PCR amplified from genomic DNA with the oligonucleotides SysII-Nterm and SysII-Cterm. The amplified product was digested with BamHI and EcoRI and ligated into pGEX-4T-1 to generate pRGK334 (system II plasmid).

For construction of a cytochrome $c_4$:hexahistidine reporter containing an arabinose-inducible ccmE gene with a C-terminal 6×His tag, the E. coli ccmE gene was amplified from pRGK333 with oligonucleotides CcmE*-Nterm and CcmE*-Cterm. The amplified product was cut with KpnI and PstI and ligated into pRGK332 to generate pRGK349.

For the construction of pRGK348, it was necessary to correct for the apparent instability of pRGK334 (system II) when both pRGK332 ($c_4$:6×His) and pHPEX2 (Varnado and Goodwin, 2004) are present, by inserting the chuA gene from pHPEX2 downstream of the ccsBA gene in pRGK334. The chuA gene along with the lacUV5 promoter, ribosome binding site, and the chuA stop codon were cut out of pHPEX2 using XbaI. Following agarose gel purification (Gene Clean, BIO 101 Systems, Irvine, Calif.) of an approximately 3.6 kb restriction fragment, the XbaI ends were filled in with Klenow fragment of E. coli DNA polymerase I and ligated to Tth111I digested pRGK334. The resulting plasmid (pRGK348) contains the chuA gene inserted 210 bp downstream of the ccsBA stop codon. The expression of chuA from pRGK348 was verified by growth of E. coli ΔccmΔhemA (RK105) in LB supplemented with heme.

e) Production of Antibodies to B. pertussis Cytochrome $c_4$

For overexpression of the soluble cytochrome $c_4$ protein, encoded by the B. pertussis cycC gene, pRGK332 was coexpressed with pRGK333 in the E. coli TB1 strain. Cells were grown to mid-exponential phase (A600=0.6) in LB containing ampicillin and chloramphenicol and induced with IPTG (1 mM) and arabinose (0.2%) for 3 h. The cytochrome $c_4$ protein was purified using $Ni^{2+}$-chelating resin (Novagen) as previously described (Feissner et al., 2005). Antiserum was generated in New Zealand white rabbits at a commercial facility (Cocalico Biologicals; Reamstown, Pa.). The antibodies were purified from the serum by ammonium sulphate precipitation and used at a 1:6000 dilution for Western blot.

f) Production of Antibodies to E. coli CcmE

For overexpression of the E. coli CcmE protein, the soluble, 134-amino-acid periplasmic region (called CcmE*) was amplified by PCR using MG1655 genomic DNA as a template and the oligonucleotides CcmE*-Nterm and CcmE*-Cterm. The resulting amplified product was digested with NcoI and XhoI and cloned into the plasmid pET2-Blue (Novagen; Madison, Wis.) to create the plasmid pRGK347. The CcmE* periplasmic protein containing a C-terminal 6×His tag was overexpressed from pRGK347 in the Tuner pLacI strain of E. coli (Novagen). Cells were grown to mid-exponential phase (A600=0.6) in LB containing carbenacillin and induced with IPTG (1 mM) for 3 h. Cells were harvested, washed in 20 mM Tris (pH 8) and resuspended in lysis buffer [20 mM Tris pH 8, lysozyme (1 mg ml-1), Triton X-100 (1%)]. After incubation on ice for 20 min, bacteria were lysed by sonication (twice for 3 min each, Branson Model 200)

using a microtip at a power setting of 40% and a duty cycle of 50%. Debris was removed by centrifugation (10 000 g, 15 min, 4° C.) and the 6×His-tagged CcmE* was purified by chromatography over Ni$^{2+}$-chelating affinity resin. Eluted protein was concentrated with Centricon 10 columns (Millipore; Billerica, Mass.) and dialysed against storage buffer (20 mM Tris pH 8, 200 mM NaCl) to remove the imidazole. Purity of the preparations, as assessed using SDS-PAGE and staining with Coomassie brilliant blue, was greater than 95%. Antiserum was generated in New Zealand white rabbits at a commercial facility (Cocalico Biologicals). The antibodies were purified from the serum by ammonium sulphate precipitation and used at a 1:5000 dilution for Western blot.

g) N-Methylprotoporphyrin Inhibition Experiments

Five milliliter cultures of *E. Coli* Δccm harboring either the pRGK333 or pRGK334 plasmid and pRGK332, or pRGK345 and pRGK349, were inoculated with 300 μl of overnight culture grown for 3 h to mid-exponential phase (A600=0.6). At this point, IPTG and NMPP (Frontier Scientific) were added to each culture; IPTG was added (1 mM) to induce the synthesis of system I (pRGK333), system II (pRGK334), or ΔccmE (pRGK345) while NMPP (10 mM stock in 50% DMSO) was added to a final concentration of 0-100 μM. After addition of IPTG and NMPP, cultures were grown an additional hour before induction of cytochrome $c_4$:His (and ccmE from pRGK349) with 0.2% arabinose. Cells were grown for an additional 3 h and then harvested by centrifugation. Soluble protein was extracted with B-PER Protein Extraction Reagent (Pierce Biotechnologies; Rockfrod, Ill.) as previously described (Feissner et al., 2005).

h) *Escherichia coli* Membrane Fractionation

*Escherichia Coli* cultures were grown at 37° C. in LB media containing the appropriate antibiotics. Soluble and membrane fractions were prepared as previously described (Feissner et al., 2005). To isolate periplasmic proteins from *E. Coli*, cells were harvested at 10 000 g for 10 min at 4° C. and washed twice with 10 mM Tris pH 8 at room temperature. The resulting cell pellet was then resuspended in ⅒ of the starting culture volume in 100 mM Tris pH 8 containing 20% sucrose (w/v). The resuspension was stirred until warmed to 37° C. and lysozyme was added to a final concentration of 100 μg/ml. After 12 min of stirring, 1 vol. of 100 mM EDTA was slowly added to 10 vols of cells over a period of 2.5 min and stirred for additional 10 min. Spheroplasts were separated via centrifugation at room temperature for 10 min at 12 000 g. The supernatant containing periplasmic proteins was saved. Crude B-PER protein extractions were carried out as previously described (Feissner et al., 2005).

i) Heme Addition Experiments

Cultures of RK105 (*E. coli* ΔccmΔhemA) harboring pRGK333 (system I), pRGK332 (cytochrome $c_4$:6×His), and pHPEX2 (Varnado and Goodwin, 2004) or pRGK348 (system II) and pRGK332 were grown in LB overnight in the presence of 300 μM aminolevulinic acid (ALA). 100 mL cultures were started from the overnight culture with a 1% inoculum in LB devoid of ALA for two and one-half hours. After two and one-half hours, the 100 mL cultures had exhausted their cellular supply of ALA and required exogenous heme (or ALA) for further growth. The ALA exhausted cultures were divided into 5 mL aliquots to which IPTG (1 mM, to induce the synthesis of the system I proteins) and heme (0 μM to 100 μM) (Sigma) were added. It was discovered that heme at greater than 60 μM would precipitate over time with no IPTG (1 mM) present and at greater than 100 μM in the presence of IPTG. After one hour, arabinose (0.2% to induce the synthesis of cytochrome $c_4$:6×His) was added and cultures were grown for an additional three hours. Cells were harvested and protein was extracted using B-PER as previously described (Feissner et al., 2006). Cytochrome $c_4$:6×His was purified from 200 μg of total protein over nickel affinity resin to eliminate free heme. 20 μL of each sample were subjected to SDS-PAGE, transferred to nitrocellulose, and heme stained as described above. Curve-fits and heme recovery calculations were performed with the Origin scientific and analysis software package (OriginLab; Northhampton, Mass.) using the Hill equation as the curve-fit model.

j) N-Methyl Protoporphyrin (NMPP) Inhibition Experiments 100 mL cultures of *E. coli* Δccm containing pRGK333 (system I), pRGK332 ($c_4$:6×His), and pHPEX2 (Varnado and Goodwin, 2004) were inoculated with 1% (v/v) from an overnight culture and grown with aeration at 37° C. to an OD$_{600}$ of approximately 0.5. The mid-log phase cultures were divided into 5 mL aliquots to which IPTG (1 mM, to induce the synthesis of the system I proteins and the chuA gene) and NMPP (0 μM to 100 μM) were added. After one hour 0.2% arabinose was added (to induce the synthesis of the *B. pertussis* $c_4$:6×His) and cultures were incubated an additional three hours. After harvesting cells by centrifugation, soluble protein was extracted with B-PER Protein Extraction Reagent (Pierce Biotechnology) as previously described (Feissner et al., 2006). Cytochrome $c_4$:6×His was purified from 300 μg of total protein by nickel affinity resin (Novagen) and 20 μL of each sample was subjected to SDS-PAGE, transferred to nitrocellulose and heme stained as described below.

k) Metalloprotoporphyrin IX Addition Experiments

Overnight cultures of an *E. Coli* Δccm strain (or *E. Coli* ΔccmΔhemA) harboring either pRGK333 (system I) or pRGK348 (system II-chuA), pRGK332 (cytochrome $c_4$:6×His), and pHPEX2 (Varnado and Goodwin, 2004) were diluted into fresh LB broth (containing the appropriate antibiotics and 8 μM hemin for the *E. Coli* ΔccmΔhemA strain) and incubated with aeration at 37° C. until the OD$_{600}$ was approximately 0.5. The mid-log phase cultures were divided into 5 mL aliquots to which IPTG (1 mM) and a metalloprotoporphyrin IX (Zn (II), Sn (IV), Co (III), or Mn (III); 0 μM to 25 μM) were added. Arabinose (0.2%) was added after one hour and incubation continued for an additional three hours. Cells were harvested and soluble protein was extracted using B-PER (Feissner et al., 2006). Cytochrome $c_4$:6×His was purified from 300 μg of total protein and 20 μL was subjected to SDS-PAGE and transferred to nitrocellulose. Prior to heme stain and c4 immunoblot, the nitrocellulose blots were screened for fluorescence on an LAS-1000 plus Luminescent Image Analyzer CCD camera system (Fujifilm; Tokyo, Japan).

l) NMPP-ZnPPIX Combined Inhibition Experiments

Overnight cultures of an *E. Coli* Δccm strain harboring pRGK333 (system I), pRGK332 (cytochrome $c_4$:6×His), and pHPEX2 were diluted into 100 mL of fresh LB broth containing the appropriate antibiotics and incubated at 37° C. with aeration until an OD$_{600}$ of approximately 0.5 was obtained. The cultures were divided into 5 mL aliquots and IPTG (1 mM) and ZnPPIX (5 μM and 12.5 μM) was added. Also at this time NMPP, at 60 μM and 100 μM respectively, was added to each of these cultures and incubation continued for one hour. Arabinose (0.2%) was added and incubation continued for an additional three hours. Cells were harvested by centrifugation and the soluble protein was extracted with B-PER, as previously described (Feissner et al., 2006). The soluble protein was processed as for "metalloprotoporphyrin addition experiments".

m) Other Methods

Heme stains were performed as described (Feissner et al., 2003) using SuperSignal Femto chemiluminescent substrate (Pierce). Heme stain quantitation used LOLITA II (Low Light Test Array; raytestUSA; Wilmington, N.C.) for standardization of light intensity detection on an LAS1000 plus Luminescent Image Analyzer CCD camera system. For Western blotting, extracts were first separated by 12% or 15% SDS-PAGE and electroblotted onto Hybond-C nitrocellulose membranes (Amersham). Protein A peroxidase (Sigma-Aldrich) was used as the secondary label. Detection used the SuperSignal West Femto ECL detection system (Pierce). Chemiluminescence from heme stains and Western blots were detected using an LAS-1000 plus Luminescent Image Analyzer CCD camera system (Fujifilm). Protein concentrations were determined using the BCA assay (Pierce) using BSA as a standard. The reduced (10 mM sodium dithionite) and oxidized (10 mM ammonia persulphate) absorption spectra were obtained as previously described (Goldman et al., 1996) using $Ni^{2+}$ affinity-purified holocytochrome $c_4$:His. Protein concentrations were determined with the BCA assay kit (Pierce) using BSA as a standard.

TABLE 1

Nucleotide sequences of primers.

| Strain or Plasmid | Primer | Nucleotides | Nucleotide Sequence 5'-3' | SEQ ID NO: |
|---|---|---|---|---|
| E. coli Δccm (RK103) | Δccm-left | 60 | CGCCTGCGCG ATACTACGTTC AATCACCGCAC GGCGAGTAGT GTAGGCTGGA GCTGCTTC | SEQ ID NO: 1 |
| E. coli Δccm (RK103) | Δccm-right | 60 | ACGCTGAACG CAGGAGAGTG GGTACAAATCA CCGGTAGCAC ATATGAATATC CTCCTTAG | SEQ ID NO: 2 |
| pRGK333 (pSystemI) | SysI-Nterm | 32 | TTGCAGATCTA TGCTTGAAGCC AGAGAGTTAC | SEQ ID NO: 3 |
| pRGK333 (pSystemI) | SysI-Cterm | 33 | CGGAATTCTTT TTATTTACTCT CCTGCGGCGA C | SEQ ID NO: 4 |
| pRGK345 (ΔccmE) | CcmD-Cterm | 30 | GGCGAATTCTC ATATGGCCTCC TGCTGTTG | SEQ ID NO: 5 |
| pRGK345 (ΔccmE) | CcmF-Nterm | 33 | GACCCAGCCA TATGATGCCAG AAATTGGTAAC G | SEQ ID NO: 6 |
| pRGK346 (ΔccmH) | CcmG-Cterm | 32 | CCAATGAATTC CTTATTGTGCG GCCTCCTTAC | SEQ ID NO: 7 |
| pRGK330 (pBad24-cm$^r$) | pBad24-left | 32 | TATAAGCTTTT TTGCCGATTTC GGCCTATTGG | SEQ ID NO: 8 |
| pRGK330 (pBad24-cm$^r$) | pBad24-right | 27 | ATCAGGCTGAA AATCTTCTCTC ATCCG | SEQ ID NO: 9 |
| pRGK331 (pcytc$_4$: Pho) | c$_4$-pho-Nterm | 27 | AGTCGCTAGC AGGAGGATTTC ATGAAG | SEQ ID NO: 10 |
| pRGK331 (pcytc$_4$: Pho) | c$_4$-pho-Cterm | 23 | GTGCTGCAAG GCGATTAAGTT GG | SEQ ID NO: 11 |
| pRGK332 (pcytc$_4$: 6xHis) | c$_4$-6xHis-Cterm | 48 | ACGGGTACCT CAGTGGTGGT GGTGGTGGTG CCGCAAGCCC GCGGCGTA | SEQ ID NO: 12 |
| pRGK334 (pSystem II) | SysII-Nterm | 32 | GGAAAGATCTA TGAAGAATCTC AAAAGCCTGC | SEQ ID NO: 13 |
| pRGK334 (pSystem II) | SysII-Cterm | 28 | TTCGAATTCCG CGTCTAATAGG GGTTGG | SEQ ID NO: 14 |
| pRGK347 (pCcmE*) | CcmE*-Nterm | 33 | GGTCCCATGG TATATGCGCTG CGCTCGAATAT C | SEQ ID NO: 15 |
| pRGK347 (pCcmE*) | CcmE*-Cterm | 35 | CTGCTCGAGT GATGCTGGGT CCTTATAAACA CTCG | SEQ ID NO: 16 |
| pRGK349 (pcytc$_4$: Pho-CcmE) | CcmE-Nterm | 33 | CAGGTACCGG AGGCTGCATG AATATTCGCCG TA | SEQ ID NO: 17 |
| pRGK349 (pcytc$_4$: Pho-CcmE) | CcmE-Cterm | 48 | ACGCTGCAGT CAGTGGTGGT GGTGGTGTG TGATGCTGGG TCCTTATA | SEQ ID NO: 18 |
| E. coli ΔccmΔhemA (RK105) | ΔhemA-left | 60 | CTATCAACGTT GGTATTATTTC CCGCAGACAT GACCCTTTGTG TAGGCTGGAG CTGCTTC | SEQ ID NO: 19 |
| E. coli ΔccmΔhemA (RK105) | ΔhemA-right | 60 | TGATGTACTGC TACTCCAGCCC GAGGCTGTCG CGCAGAATCAT ATGAATATCCT CCTTAG | SEQ ID NO: 20 |

Example 1

Figure 2:
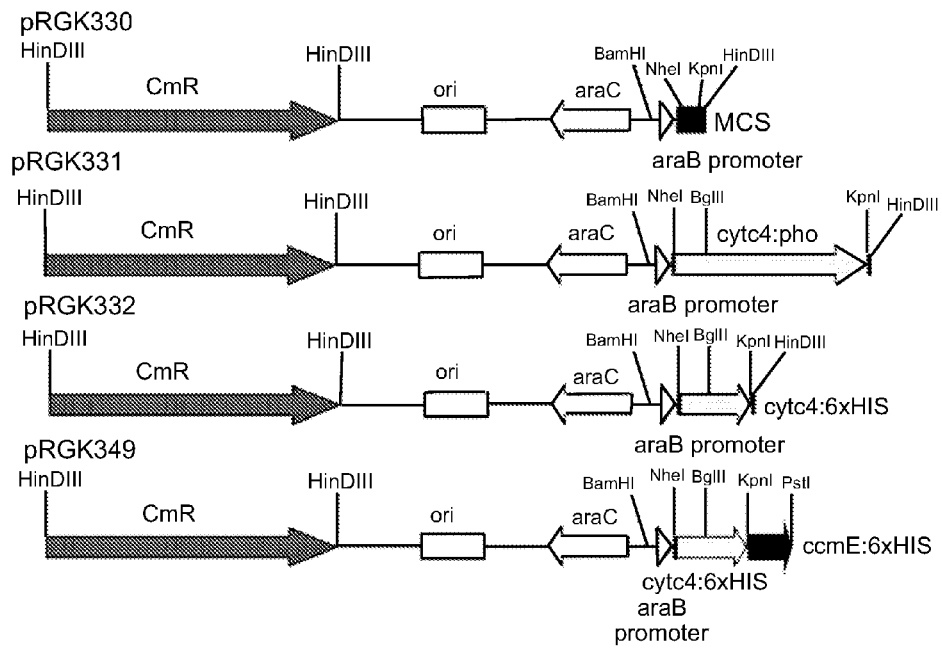
FIG. 2. Plasmids with A) cytochrome c reporters and B) cytochrome c biogenesis genes.
Figure 2:
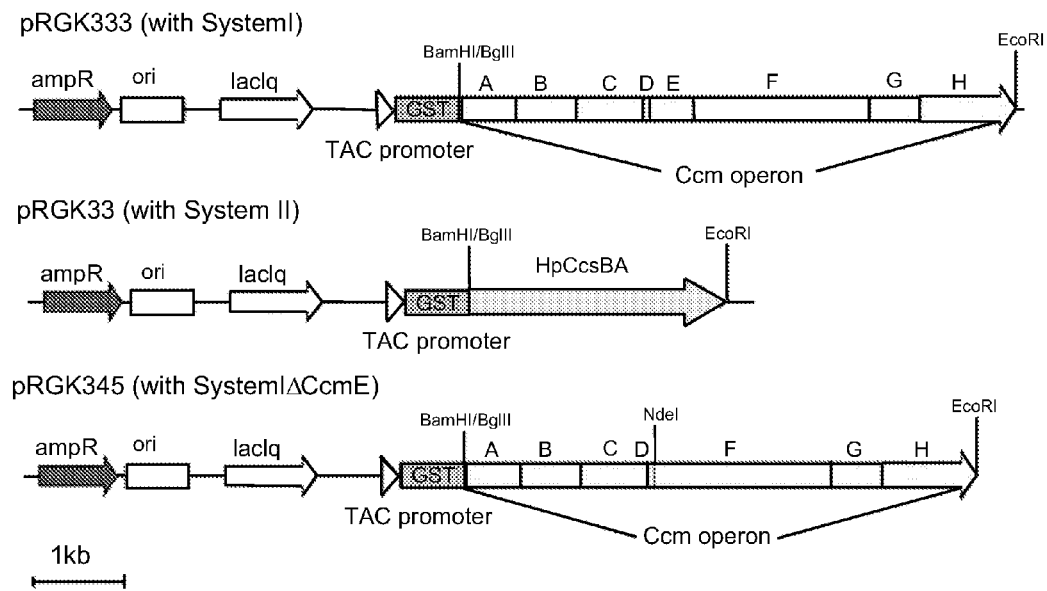
Figure 3:
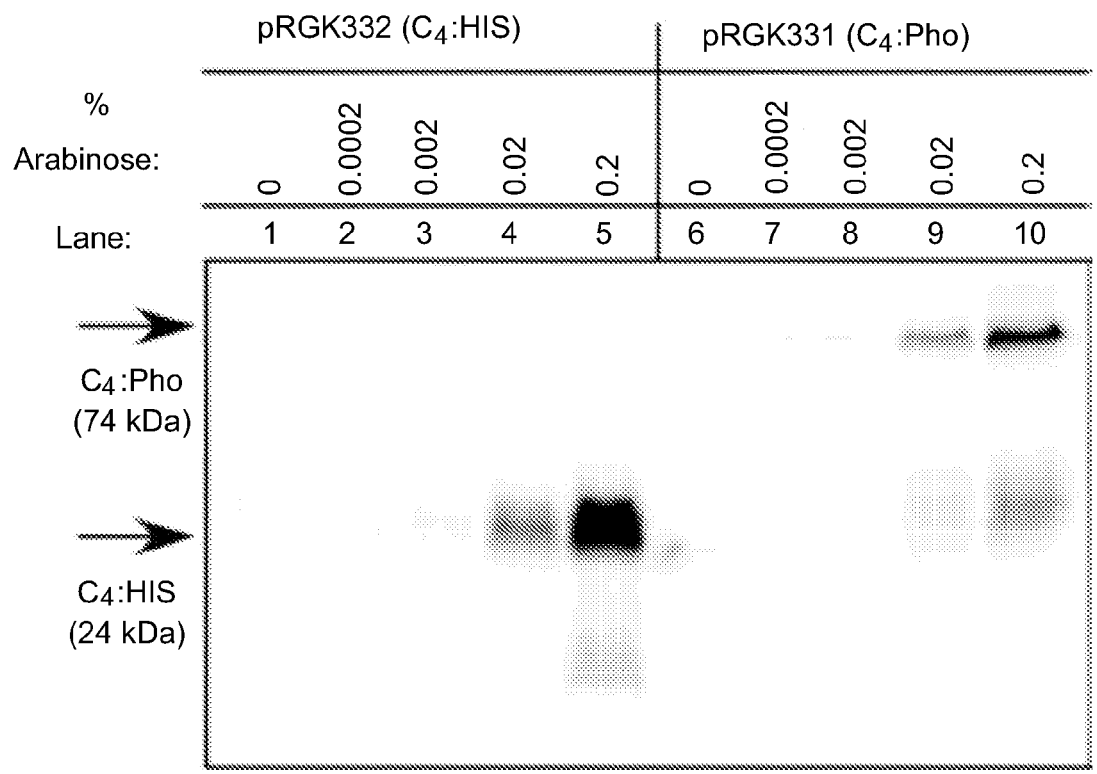
FIG. 3. Heme stain of arabinose inducible cytochrome $c_4$ reporters. *E. coli* strain MG1655 containing pRGK332 (lanes 1-5) or pRGK331 (lanes 6-10) were grown in LB and induced for 3 hours with increasing concentrations of arabinose, as indicated. Periplasmic shock proteins (50 mg) were separated by SDS-PAGE and stained for heme. The arrow labeled c4:Pho indicates the cytochrome $c_4$:alkaline phosphatase fusion protein. The arrow labeled with c4:His indicates the cytochrome $c_4$ hexahistidine tagged di-heme protein.

Arabinose-Inducible *B. Pertussis* Cytochrome c Reporters in *E. coli* were Developed Using the arabinose-inducible araB promoter from pBAD24 (Guzman et al., 1995), the ampicillin-resistance gene was replaced with a chloramphenicol-resistance cassette from pHP45-Cm (Fellay et al., 1987) to make pRGK330 (FIG. 2A). Chloramphenicol rather than ampicillin resistance is necessary so these plasmids can be co-selected with the system I and II constructs (Amp$^r$) in the *E. coli* strain deleted for system I genes (Kan$^r$; see below). A *B. pertussis* cytochrome c:alkaline phosphatase (cycC-phoA) fusion was engineered downstream of the araB promoter and initially tested for alkaline phosphatase activity on plates with and without arabinose. This plasmid, pRGK331, when present in the *E. coli* strain TB1, results in the production of an arabinose-inducible alkaline phosphatase activity. Heme staining, which only stains the covalently bound heme in c-type cytochromes separated by SDS-PAGE, indicated that a c-type cytochrome with the molecular mass of approximately 75 kDa was expressed after induction with 0.02% and 0.2% arabinose (FIG. 3, lanes 9 and 10). A lower molecular mass form (approximately 24 kDa) was observed that is similar in size to the natural holocytochrome $c_4$.

A second cytochrome $c_4$ reporter was developed with a C-terminal hexahistidine tag. This reporter plasmid, pRGK332, in *E. Coli* results in the arabinose-inducible production of a 24 kDa protein that possesses c-type heme (FIG. 3, lanes 4, 5). Thus, wild-type *E. Coli* can synthesize the *B. pertussis* cytochrome $c_4$, presumably using its chromosomally encoded system I pathway (see below).

Example 2

Figure 4A:
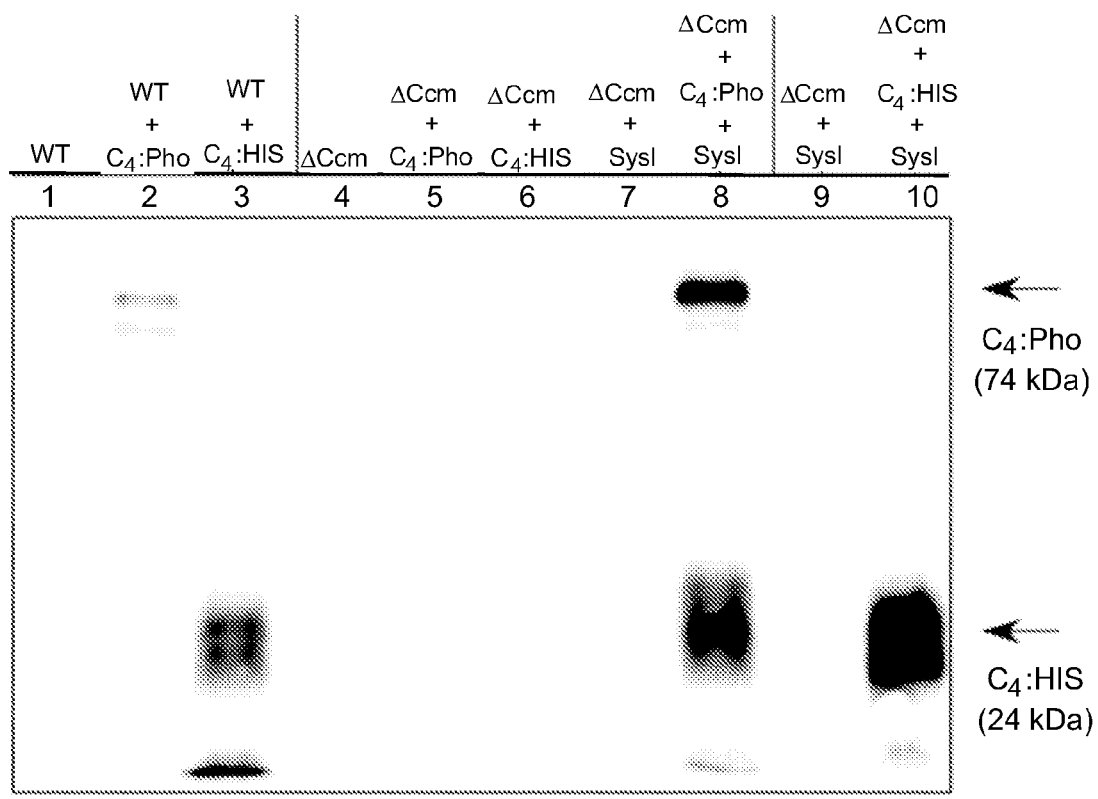
FIG. 4. Heme stains of periplasmic shock proteins from the indicated *E. coli* strains with and without recombinant system I or system II. A) Wild-type MG1655 (lanes 1-3) or RKIO3 (lanes 4-10) strains of *E. coli* were grown aerobically and induced with 1 mM IPTG and 0.2% arabinose. Above each lane number, c4:Pho indicates the presence of pRGK331; c4:His of pRGK332; SysI, pRGK333. B) RKIO3 with the indicated plasmids with symbols same as in "A" and where SysII refers to pRGK334.

An *E. coli* Strain Deleted for all ccm (System I) Genes and Complementation by Plasmids Expressing Either System I or System II Genes was Engineered and Validated Using the procedure developed by Datsenko and Wanner (2000) on the *E. Coli* strain (RK103) with arabinose-inducible cytochrome c reporters, the eight genes comprising system I, ccmA through ccmH, were deleted and replaced with a kanamycin-resistance cassette (see FIG. 2B for ccm genes at this locus) FIG. 4A shows that this ccm deletion strain, RK103, is unable to synthesize the holocytochrome $c_4$:alkaline phosphatase (lane 5) or holocytochrome $c_4$:His (lane 6), unlike the wild type (lanes 2, 3), indicating that the system I ccm genes are required for the synthesis of these cytochrome $c_4$ reporters. The ccmA through ccmH genes were engineered into the pGEX vector (amp$^r$) such that CcmA is synthesized as a fusion protein to glutathione S-transferase (GST) (FIG. 2B). This construct, pRGK333, when transformed into RK103 containing the reporters, was able to complement the cytochrome c synthesis defect. Both holocytochrome $c_4$:alkaline phosphatase and holocytochrome $c_4$:His are produced to levels approximately 10 times higher than wild type (FIG. 4A, lanes 8 and 10), partially due to the increased expression of the system I proteins (data not shown).

Figure 4B:
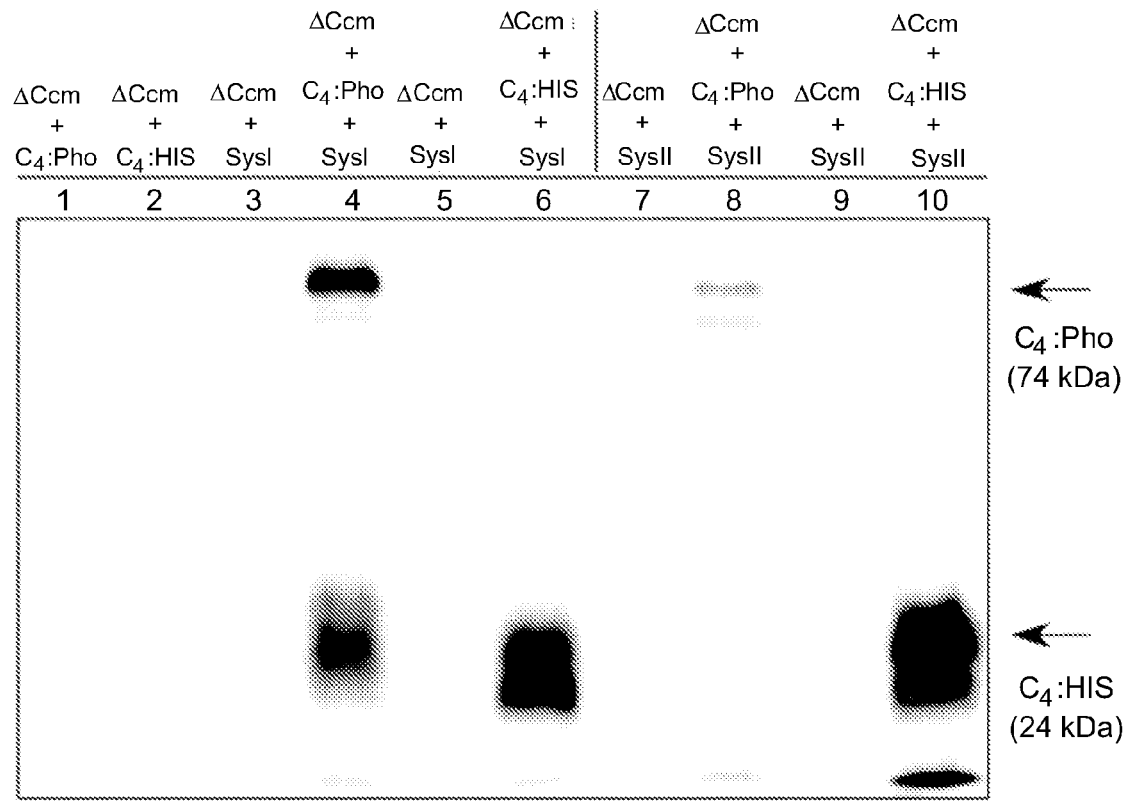
Figure 5:
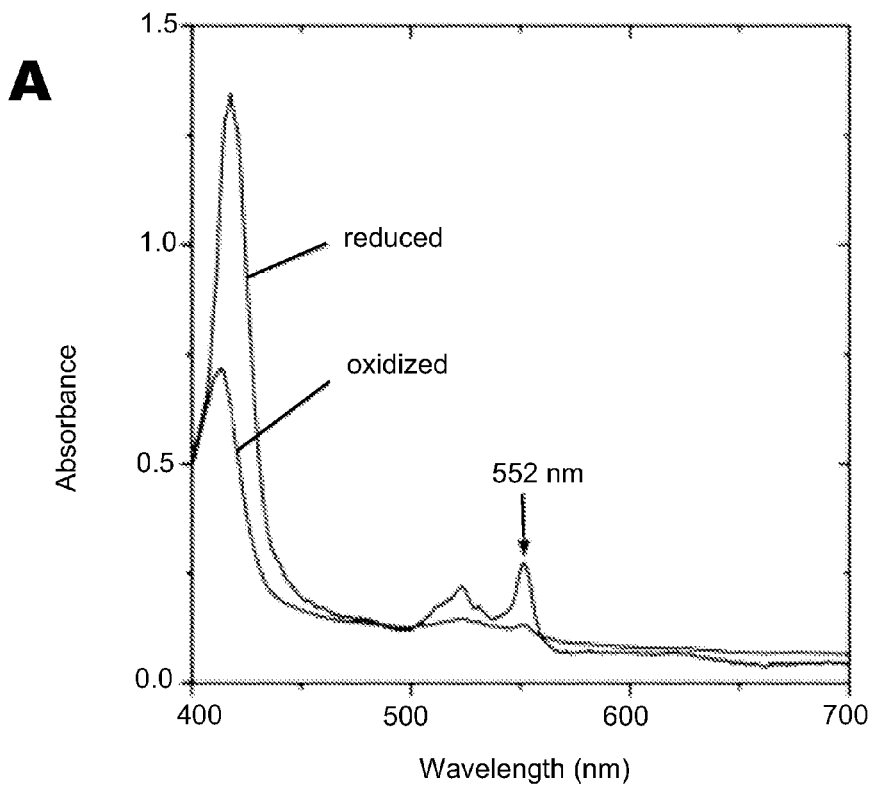
FIG. 5. Reduced and oxidized absorption spectra and mass spectrometry analysis of holocytochrome $c_4$:His produced by recombinant biogenesis systems. A) Reduced and oxidized absorption spectra of holocytochrome $c_4$:His from RKIO3 with pRGK332 and pRGK333 (system I). B) Reduced and oxidized absorption spectra of holocytochrome $c_4$:His from RKIO3 with pRGK332 and pRGK334 (system II). C) ESI-MS analysis of holocytochrome $c_4$:His from RKIO3 with pRGK332 and pRGK333. D) Amino acid sequence of the *B. pertussis* cytochrome $c_4$:His (SEQ ID NO:21). The signal sequence is underlined and the CXXCH heme binding sites are in bold. Minor, proteolytic cleavage sites are denoted with linked arrows (see text).
Figure 5:
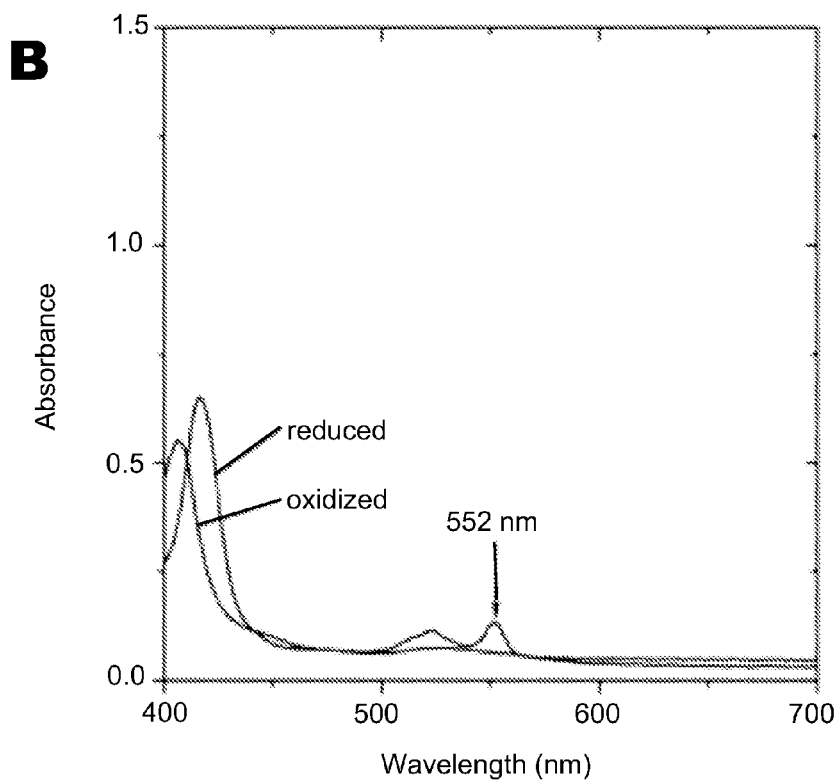
Figure 5:
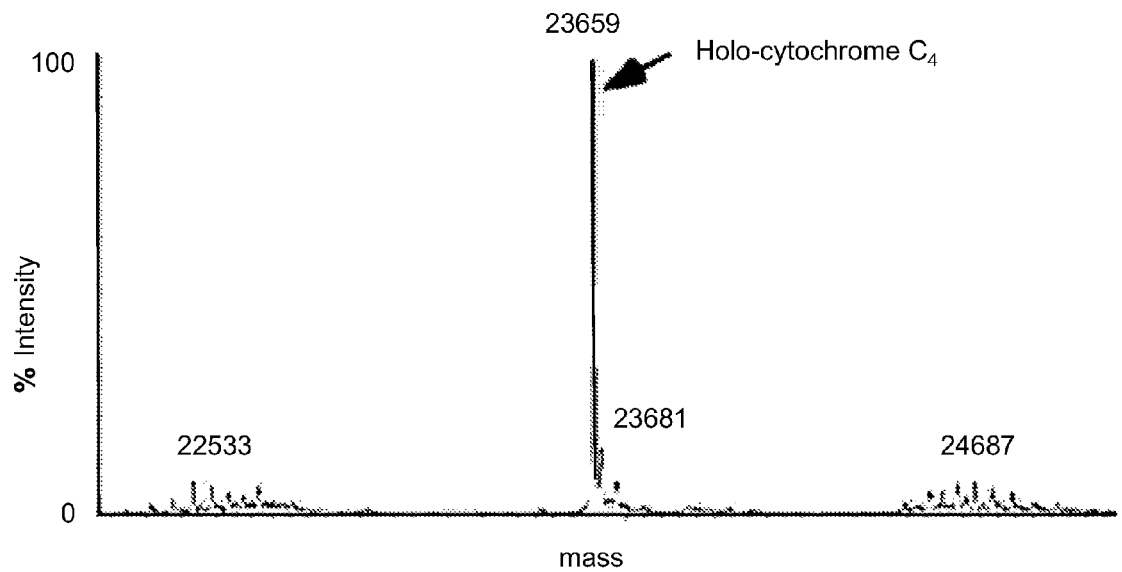

The minimal genes from system II that would carry out the biogenesis of *B. pertussis* holocytochrome c reporters in RK103 were also engineered. A natural ccsB-ccsA fused gene that is present in another proteobacterium, *Helicobacter pylori* (Tomb et al., 1997), was placed in frame to GST in pGEX-4T-1 and transformed into the *E. coli* with reporter strains described above. When present with pRGK331 in RK103, holocytochrome $c_4$:alkaline phosphatase was produced (FIG. 4B, lane 8) at the same molecular mass as when pRGK333, with system I, was present (FIG. 4B, lane 4). Likewise, when pRGK334 was present with pRGK332, a 24 kDa holocytochrome $c_4$ was produced (FIG. 4B, lane 10) at the same molecular mass as when pRGK333 was present (FIG. 4B, lane 6). To confirm that the recombinant cytochrome $c_4$ proteins had properties identical to the natural molecules, the hexahistidine-tagged proteins were purified over $Ni^{2+}$. The absorption spectra of $Ni^{2+}$-purified holocytochrome $c_4$:His showed the characteristic spectra in the α/β and Soret region whether assembled using system I (pRGK333, FIG. 5A) or system II (pRGK334, FIG. 5B). Mass spectrometry analysis of $Ni^{2+}$-purified holocytochrome $c_4$:His, when pRGK333 or pRGK334 is present, revealed a protein with a molecular mass of 23,659 Da (FIG. 5C), identical to the molecular mass of the holocytochrome $c_4$:His containing two heme molecules and a signal sequence cleaved after Ala27 (FIG. 5D). These results indicate that a single polypeptide composed of the ccsB and ccsA ORFs can replace the function of all eight genes required for system I in *E. coli*.

Besides the covalent attachment of heme to the protein, as detected by the heme stain and spectrometry, a characteristic of c-type cytochromes is that they typically fold into their native state after the heme is attached. This characteristic results in the susceptibility of apocytochromes c to degradation by endogenous proteolysis when the heme is not attached. To provide an additional line of evidence that CcsBA-mediated assembly occurs in *E. coli* similar to the natural system I in *E. coli* and system II in *B. pertussis*, antisera towards alkaline phosphatase and *B. pertussis* cytochrome $c_4$ were used to detect various forms present in periplasmic shock fractions.

FIG. 6A, an immunoblot using alkaline phosphatase antibodies shows that alkaline phosphatase was immunodetected only in extracts of strains that had the cytochrome $c_4$:alkaline phosphatase reporter (lanes 2, 6, 10). Without a biogenesis system (FIG. 6A, lane 2), a single polypeptide approximating the molecular mass of alkaline phosphatase (45 kDa) is detected, suggesting that the majority of the apocytochrome $c_4$ portion is degraded when heme is not attached. When either system I (lane 6) or system II (lane 10) is present, two additional polypeptides are observed that possess covalent heme (see heme stains in FIG. 4B, lanes 4 and 8). These polypeptides represent the full fusion protein and one that is degraded down to the size of the mono-heme cytochrome $c_4$:alkaline phosphatase fusion protein (approximately 74 kDa and 62 kDa respectively, see below). In *E. coli*, either system I or heterologous system II attach heme and holocytochrome $C_4$ subsequently folds into a stable protease-resistant form.

Figure 6C:
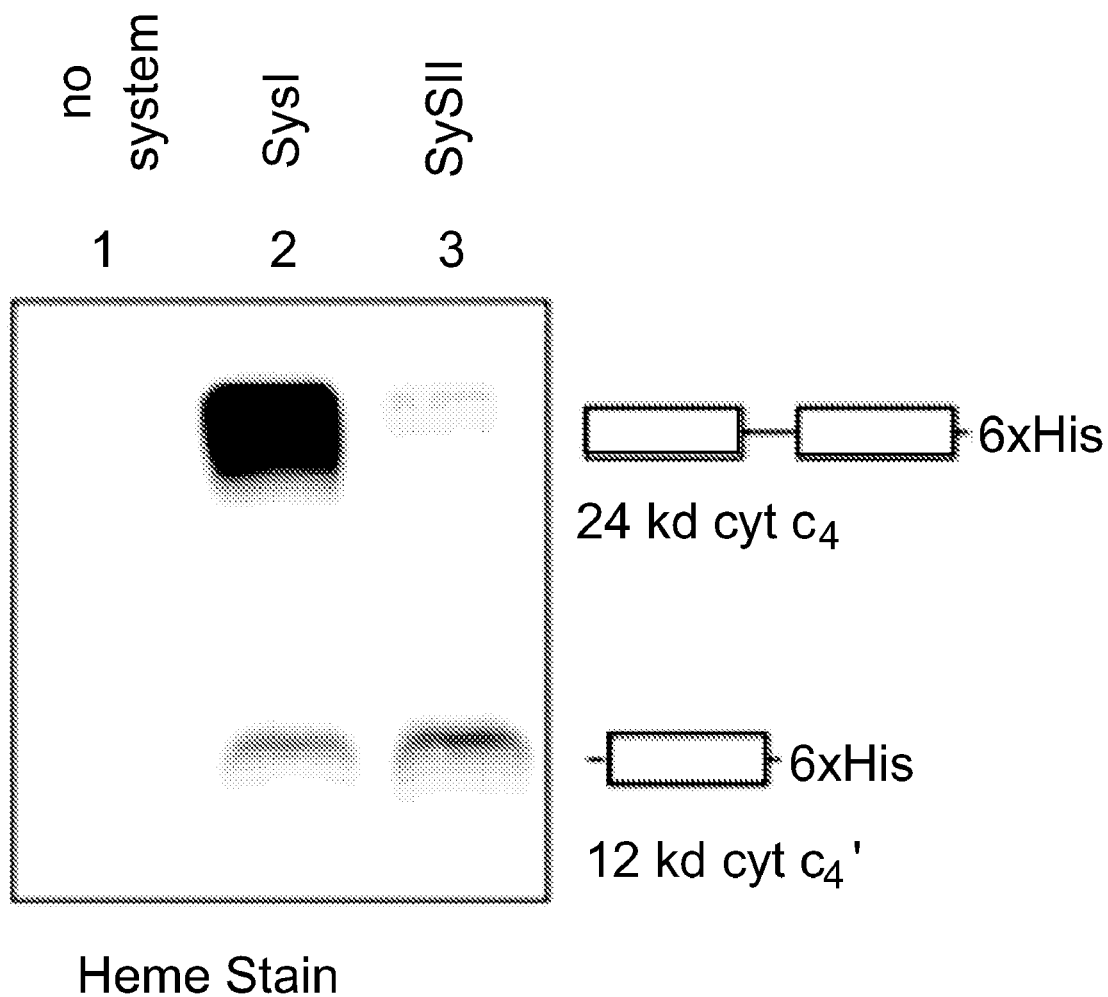
Figure 6D:
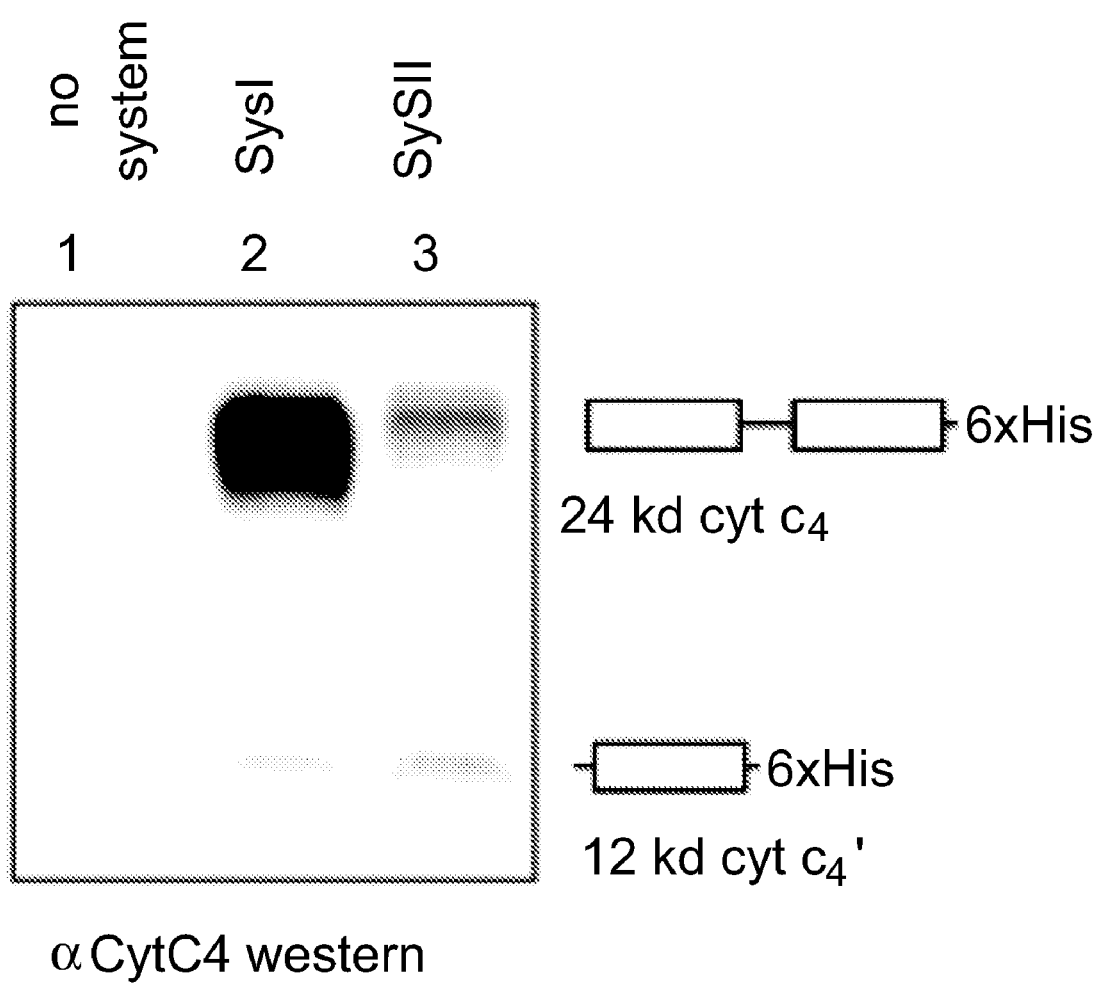

When antisera to cytochrome $c_4$ was used, each of the three alkaline phosphatase forms described above were detected (FIG. 6B, lanes 2, 6, 10), although the lower molecular mass protein was less pronounced, suggesting that the product similar in size to the alkaline phosphatase polypeptide still retains minor antigenic determinant(s) from the cytochrome $c_4$ C-terminus. (With the cytochrome $c_4$ antisera, a contaminating immunoreactive polypeptide slightly higher than 24 kDa is seen in all lanes, which can be used as an internal standard for protein loaded.) When the cytochrome $c_4$:His-tagged protein is produced in a strain without a biogenesis system, no apocytochrome $c_4$ is detected (FIG. 6B, lane 1), whereas extracts from strains with either system I (lane 4) or system II (lane 8) produce significant amounts of detectable cytochrome $c_4$ polypeptide at 24 kDa. These extracts were further purified over Ni2+ affinity columns and holocytochrome $c_4$ was detectable by heme stain (FIG. 6C) or immunoblot (FIG. 6D) only when either system I or II is present. These results also confirm that the di-heme 24 kDa cytochrome $c_4$ is partially proteolysed in *E. coli* to the mono-heme 12 kDa forms. Mass spectrometry of $Ni^{2+}$ affinity-purified holocytochrome $c_4$, with pRGK333 present, revealed the 23,659 Da form (FIG. 5C) and two proteins of mass 12,891 Da and 12,991 Da (not shown), consistent with a single heme moiety and proteolysis after N125 and V126 (see FIG. 5D).

The complete susceptibility of hexa-histidine-tagged apocytochrome $c_4$ to proteolysis but resistance of the holo forms in these recombinant cells substantiates that the ccsBA-encoded system II in *E. coli* is functional.

In *E. coli*, the CcsB and CcsA protein complex carries out the heme delivery function and periplasmic cytochrome $c_4$-heme ligation functions with no additional requirements, other than the reduction of the cysteinyl residues of the CXXCH motifs.

Example 3

Heme Limitation Highlighted Differences in Heme Acquisition Dynamics Between System I and System II Using the reconstitution of system I and system II in a single genetic background (see Example 2) the ability of these two systems to deliver heme for holocytochrome $c_4$ synthesis was directly compared by measuring the ability of each system to synthesize holocytochrome $c_4$:His under conditions of reduced cellular heme availability. To reduce available heme levels, selected concentrations of the specific ferrochelatase inhibitor NMPP were used in the growth cultures (Moody and Dailey, 1985; Ferreira, 1994).

Cultures of RK103 harboring both pRGK333 (system I) and pRGK332 (cytochrome $c_4$:His) were grown to early log phase, then IPTG (1 mM) was added to induce the synthesis of the system I proteins. At the same time, NMPP was added to the growing cultures at final concentrations of 0-100 μM in order to inhibit ferrochelatase, and subsequently reduce cellular heme levels. One hour later, arabinose (0.2%) was added to the cultures to induce production of apocytochrome $c_4$:His. Cells were grown for additional 3 h and harvested.

NMPP did not reduce the production levels of system proteins or of apocytochrome $c_4$:alkaline phosphatase (data not shown). Cytochrome $c_4$:His was extracted using B-PER bacterial protein extraction reagent (Pierce). As visualized via a heme stain, holocytochrome $c_4$:His signal decreased gradually as NMPP concentration increased (FIG. 7A, lanes 1-9 and 7B), but holocytochrome $c_4$:His production never went below approximately 38% of untreated wild-type levels (see FIG. 7A, lane 9).

When NMPP inhibition was carried out in RK103 harboring pRGK334 (system II) and pRGK332 (cytochrome $c_4$:His) using the same protocol, holocytochrome $c_4$:His production dropped significantly at much lower NMPP concentrations than was shown for system I (FIG. 8A lanes 1-9). Holocytochrome $c_4$:His production was completely abolished at less than 20 μM NMPP in all trials. The dramatic difference between system I and system II suggests that system I is capable of acquiring heme at significantly lower heme levels than system II. It is proposed that this capability is due to the presence of an ABC transporter that is used in system I (see FIG. 1). System II uses a single protein (CcsA) for heme delivery, and our data suggest a significantly lower affinity for heme for the CcsA protein.

Example 4

Holo-CcmE of System I can Function as a Heme Reservoir

A higher affinity for heme acquisition in system I is not sufficient to explain the differences heme acquisition dynamics between systems I and II (see Example 3). One possibile explanation is that there is a 'heme reservoir' for system I, not present in system II. CcmE, a periplasmic heme chaperone, covalently binds heme in the periplasm and may potentially function as a periplasmic heme storage protein. Antisera to CcmE was used to observe levels of CcmE in the membranes of IPTG-induced and uninduced cells expressing pRGK333, or single gene deletions [pRGK345 (ΔccmE) and pRGK346 (ΔccmH)]. As shown in FIG. 9A, CcmE was only detected in extracts of strains with the ccmE gene (lanes 3, 4, 7, 8). Additionally, CcmE is produced in the absence of IPTG in cells expressing pRGK333 and pRGK346, indicating a low level of constitutive expression (FIG. 9A, lane 3). This production is due to transcription from several minor promoters in ccmB through ccmC, upstream of ccmE and not due to 'leakiness' of the Tac promoter that drives GST:CcmA-Heme staining of membrane proteins from uninduced cells harboring pRGK333 showed that significant holo-CcmE (FIG. 9B) was present in the membrane. The presence of CcmE bound heme in both a functional (pRGK333) system I pathway and a system I pathway with a ccmH deletion (pRGK346) provided evidence of the ability of system I to store heme on CcmE.

To confirm the above results, pRGK332, the arabinose-inducible cytochrome $c_4$:His reporter, was modified to have a hexahistidine-tagged *E. coli* ccmE gene downstream of the gene for cytochrome $c_4$:His (FIG. 2A). This plasmid, pRGK349, in *E. coli* RK103 also harboring pRGK345 (a complete system I with a ccmE deletion), resulted in the arabinose-inducible production of the 24 kDa cytochrome $c_4$ (FIG. 10A) as well as the arabinose-inducible production of CcmE (FIG. 10B). NMPP inhibition was carried out by the same method as in Example 3 with RK103 expressing pRGK345 and pRGK349. A dramatic reduction in the amount of holocytochrome $c_4$:His was detected at 100 μM NMPP (see FIGS. 10C and D) when compared with the results of Example 3 (pRGK333 and constitutively produced CcmE, see FIG. 7B). These results suggest that holo-CcmE represents up to 80% of the heme reservoir in system I cytochromes c biogenesis. System II, with no storage mechanism, is unable to maintain a supply of heme for cytochromes c biogenesis.

Example 5

The Exogenous Porphyrin Approach: Characterization of an *E. coli* ΔccmΔhemA with a Porphyrin Porin Using a strain of *E coli* with all eight ccmA-H genes deleted using a kanamycin resistance cassette (see Example 2), a heme-dependent strain was constructed. After screening for the excision of this kanamycin resistance cassette to obtain the Δccm kanamycin-sensitive strain (RK104), the hemA gene was replaced with a kanamycin resistance cassette, yielding the ΔccmΔhemA strain (RK105). Because the hemA gene codes for amino levulinic acid (ALA) synthase, the first committed enzyme in heme biosynthesis (see FIG. 11), the ΔccmΔhemA strain (RK105) required ALA in the growth media to form colonies. RK105 with recombinant system I (pRGK333), or system II (pRGK334), also required exogenous ALA for growth (see FIG. 19). To determine if exogenous ALA facilitates cytochromes c synthesis we transformed these strains with pRGK332, which expresses a C-terminally hexahistidine (6×) tagged *Bordetella pertussis* cytochrome $c_4$ under the control of an arabinose inducible promoter (see Example 1). *E. coli* ΔccmΔhemA with either pRGK333 (recombinant system I) or pRGK334 (recombinant system II) as well as pRGK332 (arabinose inducible reporter) were unable to synthesize holocytochrome $c_4$:6×His at the 60 μM ALA concentration (see FIG. 12 lanes 1, 2, 6 and 7) but were able to synthesize holocytochrome $c_4$:6×His at higher ALA concentrations (see FIG. 12 lanes 3, 4, 5, 8, 9, and 10), indicating that exogenous ALA is required for growth and holocytochrome c production in RK105.

To determine if exogenous heme rather than ALA could support growth, an overnight culture of E. coli ΔccmΔhemA, supplemented with 300 μM ALA, was used to inoculate [1% (v/v)] fresh LB medium containing different concentrations of heme (0 μM to 100 μM). Growth was not detected until four to five days after the original inoculation, even at high heme concentrations, and no holocytochrome $c_4$:6×His production was detected in cultures that contained either the system I or system II plasmid and the $c_4$:6×His reporter under these conditions.

Since the outer membranes of some strains of E. coli are poorly permeable to heme, the heme porin from pHPEX2 (Varnado and Goodwin, 2004) was expressed. The tetracycline-resistant pHPEX2 expresses the gene for the heme receptor (chuA) from E. coli O157:H7 using the IPTG-inducible lacUV5 promoter. ChuA is a member of a class of relatively nonspecific enterobacterial heme receptors that are TonB-dependent and facilitate heme acquisition from the environment and recognize free heme and heme bound to a variety of proteins (see FIG. 11). Growth of E. coli ΔccmΔhemA containing either pRGK333 or pRGK334 and pHPEX2 was dependant on exogenous heme (see FIG. 13). Expression of chuA (pHPEX2) allows growth to near wild-type levels, suggesting an efficient uptake of exogenous heme, whereas when the culture is depleted for ALA and heme is not added, no growth is detectable (see FIG. 13 open squares). The pHPEX2 also facilitates the heme-dependent production of the B. pertussis $c_4$:6×His when the plasmids with system I or system II are present (see below).

To directly examine the difference in heme acquisition between systems I and II, varying concentrations of exogenous heme were supplied to E. coli ΔccmΔhemA, expressing ChuA with pRGK332 and either system plasmid. Overnight starter cultures supplemented with 300 μM ALA were used to inoculate [1% (v/v)] LB devoid of ALA and incubated for two and one-half hours to exhaust cellular ALA (and heme). The ALA-exhausted cultures were then grown in the presence of IPTG (1 mM), arabinose (0.2%), and heme (0 μM to 100 μM). The cytochrome c4 acts as a trap, allowing quantitation of the levels of heme that have fluxed through each system. Cytochrome $c_4$:6×His was purified over nickel chelating resin to eliminate free heme and quantitated by heme stain (FIG. 14A for system 1 and 14C for system II). For system I, it was determined that maximum synthesis of holocytochrome $c_4$:6×His occurs at less than 10 μM heme, therefore, all subsequent experiments using system I were carried out at heme levels between 0 μM and 10 μM. Averaged over 4 trials for system I, holocytochrome $c_4$:6×His levels were restored to 50% (of maximum levels achieved with exogenous heme) at 1.9 μM+/−0.4 μM heme (FIG. 14B). For experiments with system II (CcsBA), an increase in holocytochrome $c_4$:6×His signal was also observed as heme concentration increased, with heme levels of 80 μM to 100 μM reaching maximum synthesis (FIG. 14C). Averaged over 3 trials, holocytochrome $c_4$:6×His levels reached 50% of maximum synthesis at 54.4 μM+/−18.2 μM heme for system II (FIG. 14D). The apparent affinity for heme is at least twenty fold higher for system I than system II.

Example 6

Zinc Protoporphyrin IX (ZnPPIX) is not Incorporated into the B. Pertussis Cytochrome $c_4$:6×His Biogenesis Reporter The chemical properties of iron may not be uniquely critical for its attachment to apocytochrome c during cytochromes c biogenesis. To test whether any of the cytochromes c biogenesis systems can incorporate other metal porphyrins, four metalloporphyrins were chosen to screen for incorporation into the into the CXXCH motif of a c-type cytochrome: ZnPPIX, SnPPIX, MnPPIX, and CoPPIX. These four metalloporphyrins were tested to determine whether heme can be replaced by other metalloporphyrins in the c-type cytochrome ($c_4$:6×His) reporter. Cultures of E. coliΔccmΔhemA containing pRGK333 (system I), pRGK332 ($c_4$:6×His), and pHPEX2 were grown overnight in 300 μM ALA and subcultured into fresh LB medium containing 8 μM heme and grown to an $OD_{600}$ of 0.5. IPTG and metalloporphyrin (8 μM, 12.5 μM, or 25 μM) were then added and growth continued for one hour. Arabinose was added to 0.2% to induce the synthesis of the $c_4$:6×His and growth continued for three more hours before cells were harvested. The cytochrome $c_4$:6×His proteins were affinity purified over nickel columns, subjected to SDS-PAGE and transferred to nitrocellulose and subsequently heme stained. As expected, heme was detected on $c_4$:6×His when either 8 μM or 25 μM heme alone was added (FIG. 15 lanes 1 and 2, respectively). When ZnPPIX was present with 8 μM heme, decreasing amounts of holocytochrome $c_4$ were detected as the ZnPPIX concentration increased (FIG. 15 lanes 3-5). At 25 μM ZnPPIX (see FIG. 15 lane 5) the level of heme on $c_4$:6×His was nearly undetectable. Concentrations of ZnPPIX above 25 μM did not further reduce the level of detectable heme (not shown). SnPPIX also reduced the level of detectable heme on $c_4$:6×His (see below). However, neither CoPPIX nor MnPPIX had any affect on the levels of cytochromes c (not shown).

ZnPPIX (and SnPPIX), when present with 8 μM heme, may compete with heme for ChuA-dependent transport into the cell. Using an E. coli Δccm strain (RK103) that has endogenous heme production, it was tested whether ZnPPIX (and SnPPIX) caused a reduction in holocytochrome c4 levels detectable by heme stain. When E. coliΔccm with pRGK333 (system I), pRGK332, and pHPEX2 were treated with ZnPPIX, a decrease in holocytochrome $c_4$:6×His was detected as the concentration of ZnPPIX was increased (FIG. 16A left panel, lanes 1-5). E. coli Δccm with system II expressing chuA also showed a decrease in holocytochrome $c_4$:6×His with ZnPPIX (FIG. 16B left panel, lanes 1-6).

The three other metal protoporphyrins, SnPPIX, MnPPIX, and CoPPIX, were also tested in the E. coli Δccm background with system I or II. E. coli Δccm with pRGK332 (cytochrome $c_4$:6×His), expressing chuA and either system I or II, showed a decrease in holocytochrome $c_4$:6×His as the concentration of SnPPIX was increased (FIG. 20A lanes 1-5 and 20B lanes 1-5). Addition of MnPPIX or CoPPIX (up to 100 μM) showed no decrease in the level of heme on $c_4$:6×His, suggesting that these are not incorporated and are not inhibitors (see below). The reduction of holocytochrome $c_4$:6×His with system I required significantly higher concentrations of SnPPIX than system II, in these experiments. The concentration of SnPPIX compared to ZnPPIX required for holocytochrome $c_4$:6×His reduction was also higher for both systems. The concentration of ZnPPIX required for 50% inhibition of system I was approximately 2 µM and for system II was approximately 25 nM, whereas the concentration of SnPPIX required for 50% inhibition of system I was approximately 65 µM and for system II was approximately 18 µM.

It was determined that ZnPPIX does not react with the chemiluminescent substrate used to stain for heme on holo-cytochrome c4 (unpublished). The absence of a heme stain could indicate that ZnPPIX is either 1) competing with heme and is being incorporated into $c_4$:6×His, or 2) is specifically inhibiting c-type cytochrome biogenesis (i.e. attachment of heme).

Cytochrome $c_4$ covalently bound to ZnPPIX would be highly fluorescent, a property of ZnPPIX proteins. We were unable to detect fluorescence of ZnPPIX in purified $c_4$:6×His preparations from these experiments, suggesting that ZnPPIX is not incorporated. To confirm this, cytochrome $c_4$ immunoblots were performed on nickel affinity purified $c_4$:6× His. If ZnPPIX is incorporated into the apocytochrome c it was expected that the holocytochrome would be stable and not subject to natural proteolysis. Cultures of E. coli Δccm harboring pRGK332 ($c_4$:6×His) and either system I or II that express chuA were grown and treated as described above. When antisera to the B. pertussis cytochrome $c_4$ was used (FIGS. 16A and B right panels) a decrease in the levels of $c_4$:6×His was detected for both system I (FIG. 16A right panel lanes 6-10) and system II (FIG. 16B right panel lanes 7-12). These results suggest that ZnPPIX is not incorporated into the cytochrome $c_4$:6×His by either system but rather is inhibiting biogenesis. Similar results were observed when SnPPIX was used (FIG. 20A lanes 6-10 and 20B lanes 6-10), which also suggest that SnPPIX is not being incorporated into cytochrome $c_4$:6×His by system I or II.

To confirm that ZnPPIX is not incorporated into the cytochrome $c_4$, visible absorption spectra were obtained of nickel purified cytochrome $c_4$:6×His isolated from Δccm harboring pRGK333 (system I), pRGK332 ($c_4$:6×His), and pHPEX2 grown with 8 µM ZnPPIX (see FIG. 17A). Note that at this concentration, approximately 20% of wild type levels of holocytochrome $c_4$:6×His is produced (see FIG. 16A, lane 3). The sodium hydrosulfite reduced α peak at 552 is characteristic of cytochrome $C_4$ with a c-type linkage to heme. If ZnPPIX were incorporated we would have expected β/α peaks at 549 and 585, respectively. In addition, ESI-MS analysis of this same protein preparation showed that the holocytochrome $c_4$*(12 kDa proteolytic fragment) contained only heme, as ZnPPIX incorporation would have yielded a protein that was 10 mass units larger (FIG. 17B and inset). These results confirm that ZnPPIX is not incorporated into cytochrome $c_4$:6×His but rather inhibits biogenesis.

To rule out that ZnPPIX is not affecting some basic cellular processes, growth studies were performed with E. coli Δccm harboring pRGK333 (system I), pRGK332 ($c_4$:6×His), and pHPEX2. Cultures with either 12.5 µM or 25 µM ZnPPIX showed no decrease in the rate or yield of growth when compared to the same strain without ZnPPIX (FIG. 21). In addition, using a plasmid with $c_4$:Pho [B. pertussis cytochrome $c_4$ alkaline phosphatase fusion that is induced with arabinose (see Example 1), alkaline phosphatase was detectable at equivalent levels in the presence or absence of ZnPPIX (FIG. 22A lanes 6 and 7). These results indicate that ZnPPIX is not inhibiting transcription, translation, or secretion of cytochrome $C_4$, further suggesting that ZnPPIX is specifically inhibiting some step(s) in c-type cytochrome biogenesis.

Example 7

ZnPPIX Specifically Inhibits System I c-Type Cytochrome Biogenesis after HoloCcmE Synthesis Previously, it was determined that ZnPPIX is specifically inhibiting some step(s) in c-type cytochrome biogenesis (see Example 6). To examine where ZnPPIX is inhibiting system I c-type cytochrome biogenesis, the presence of heme on cytochrome $c_4$:6×His was assayed when both N-methyl protoporphyrin (NMPP) and ZnPPIX were included in the culture of E. coli Δccm containing pRGK333 (system I), pRGK332 ($c_4$:6×His), and pHPEX2. When NMPP, a potent inhibitor of ferrocheletase that can completely abolish heme synthesis, was added to the culture of E. coliΔccm containing pRGK333 (system I) and pRGK332 ($c_4$:6×His), holocytochrome c synthesis was reduced to a basal level of approximately 38% (see Example 3). This result was shown to be due to the ability of the CcmE protein to act as a reservoir for heme, thus permitting residual (38%) synthesis of holocytochrome $c_4$:6×His when 100 µM NMPP was added to the culture (see Example 4). Thus, in these experiments holoCcmE is present at levels that allow 38% of holocytochrome $c_4$ production when ferrocheletase is inhibited. If ZnPPIX inhibits synthesis significantly more than NMPP, it must be acting after the formation of this heme reservoir since some holoCcmE is present at the time of ZnPPIX addition (see FIG. 11).

Cultures of E. coliΔccm containing pRGK333 (system I), pRGK332 ($c_4$:6×His), and pHPEX2 were grown to mid-log phase and NMPP (60 µM and 100 µM) and IPTG (1 mM) were added. Following incubation for 30 minutes, ZnPPIX (5 µM and 12.5 µM) was added, independently, to these cultures and incubation continued for 30 additional minutes. Arabinose (0.2%) was added to induce the expression of cytochrome $c_4$:6×His and growth continued for three more hours. In addition, inhibition experiments were performed that contained either 0 µM to 100 µM NMPP or 0 µM to 25 µM ZnPPIX alone. Cells were harvested and protein was extracted using B-PER. Cytochrome $c_4$:6×His was nickel affinity purified and quantitated by heme stain (FIG. 18). When both NMPP and ZnPPIX were present the holocytochrome $c_4$:6×His levels dropped from approximately 54% with NMPP alone (FIG. 18, 60 µM NMPP) to approximately 7% at 60 µM NMPP/5 µM ZnPPIX and from approximately 30% (FIG. 18, 100 µM NMPP) to 0% at 100 µM NMPP/5 µM ZnPPIX. This result is consistent with previous data showing that ZnPPIX inhibits holocytochrome $c_4$:6×His production to nearly undetectable levels (see Example 6).

ZnPPIX is inhibiting downstream of holoCcmE since this "heme reservoir" is no longer available for cytochrome $c_4$ biogenesis. The WWD containing protein CcmF may the target for ZnPPIX (see FIG. 11). If the target for ZnPPIX is a heme binding protein (site), then exogenous heme should compete with this inhibition (i.e. ZnPPIX binding). To test this, we cultured E. Coli Δccm with system I, ChuA, and cytochrome $c_4$:Pho grown with 12.5 µM ZnPPIX and increasing concentrations of additional heme and observed a corresponding increase in holocytochrome $c_4$:Pho (FIG. 22B lanes 1-5). The same heme stained polypeptides were confirmed to be full length cytochrome $c_4$:Pho fusion proteins by Western blot (FIG. 22A, lane 1-5). ZnPPIX is a specific inhibitor of c-type cytochrome biogenesis by either system I or system II, but heme is able to compete with ZnPPIX inhibition.

Example 8

Previously Developed Recombinant Cytochrome c (His6 Tagged) Reporters May be used to Develop High Throughput Screening Technology for Cytochrome c Many strains, plasmids, and growth conditions have already been investigated to detect cytochrome c reporters at the subpicomole level. These assays are from less than one milliliter cultures. These reagents may be used to optimize ECL-(chemiluminescent-) based detection of the cytochrome c product in 96 & 384 well microtiter plate format, as a primary screen. The primary screen may involve induction with arabinose of the cytochrome c:His reporter (see Example 1) after inhibitors are added; this screen may capture inhibitors of cytochrome c and heme synthesis, secretion, translation, and transcription.

Preliminary data on a subset of conditions using 96-well plates and a luminometer indicates that the ECL-(chemiluminescent-) based detection of cytochrome c in whole *E. coli* cells may serve as HTS format. Recently, 96 well assays were piloted using a Luminoscan plate luminometer and Pierce ECL reagents. It was determined with the Luminoscan that whole cells expressing the cytochrome c reporter could be used. Pure cytochrome $c_4$ and whole *E. coli* cells synthesizing cytochrome c4 were detected in 96 well opaque (white) plates (FIG. 10). The detection sensitivity of pure cytochrome $c_4$ surpassed the Fuji CCD detection limits (see FIG. 23), well #11D, where 0.2 ng is detected at 2076 RLU=relative light units). As shown in FIG. 23, *E. coli* that did not contain a pathway (columns 4-6) or did not have the cytochrome $c_4$ plasmid (columns 1-3) exhibited significantly less luminescence than cells synthesizing holocytochrome c (columns 7-9). Although it was determined that some factor in the LB culture was quenching the signal when more than 15 µl of LB culture was used, assays with 10 µl culture or less (in LB media) showed significant signal.

To provide confidence that the ECL signal from this microtiter plate assay is emanating from the cytochrome $c_4$, rather than some unknown source, one ml of culture in LB, using the same strains as used in the 96 well plate assays, were sonicated, unbroken cells centrifuged, and supernatant (15 µl) in LB was run on a native PAG and ECL-stained (FIG. 24). FIG. 24 shows that the major ECL signal was from the cytochrome $c_4$ and that extracts of *E. coli* cells not synthesizing cytochrome $c_4$ showed no signals.

A secondary screening method for detection of holocytochrome c4 may use high-titer antisera to cytochrome c4. It is common that c-type cytochromes are degraded naturally if the heme is not attached. Cytochrome c4 antisera have been used to show that no cytochrome c4 is immunodetected when a functional system is not present, or is inhibited by a non-iron metal porphyrin (see Examples 2 and 6). Purified anti-sera to cytochrome c4 may offer another capability for detection of holocytochrome c (and thus small molecule inhibitors of the pathways). Western detection in combination with heme stains may be used as a secondary screening for cytochromes c, with the capacity to complete 1000 assays in a 2-3 week period A cytochrome c: alkaline phosphatase (PhoA) fusion reporter may also be used as an additional secondary screening to confirm specific inhibition of cytochrome c synthesis. Cytochrome c: PhoA fusion is synthesized as a holocytochrome c and active alkaline phosphatase fusion protein (see Example 1). When inhibited (or no system is present) the fusion protein does not possess heme. Moreover, the cytochrome $c_4$ domain is degraded but the alkaline phosphatase component has wild-type activity and it is detected by western blot at the same size as alkaline phosphatase. These properties will be used to confirm inhibition by small molecules and to demonstrate specificity towards the cytochrome c assembly system(s). The PhoA fusion analysis may confirm inhibition of cytochrome c (or heme) synthesis by detecting the natural degradation of the cytochrome c component (because heme is not attached), and the alkaline phosphatase (PhoA) component is used to show that transcription, translation, or secretion is not the target for the putative small molecule inhibitor. These assays have shown that the Zn and Sn PPIXs are specific large molecule inhibitors of systems I and II pathways (see example 7).

REFERENCES

All references cited in the preceding text of the patent application or in the following reference list, to the extent that they provide exemplary, procedural, or other details supplementary to those set forth herein, are specifically incorporated by reference to the same extent as if each individual publication or patent application was specifically and individually indicated to be incorporated by reference.

Alexeyev, M. F., Shokolenko, I. N., and Croughan, T. P. (1995) New mini-Tn5 derivatives for insertion mutagenesis and genetic engineering in gram-negative bacteria. *Can J Microbiol* 41: 1053-1055.

Beckett, C. S., Loughman, J. A., Karberg, K. A., Donato, G. M., Goldman, W. E., and Kranz, R. G. (2000) Four genes are required for the system II cytochrome c biogenesis pathway in *Bordetella pertussis*, a unique bacterial model. *Mol Microbiol* 38: 465-481.

Datsenko, K. A., and Wanner, B. L. (2000) One-step inactivation of chromosomal genes in *Escherichia Coli* K-12 using PCR products. *Proc Natl Acad Sci USA* 97: 6640-6645.

Feissner, R., Xiang, Y., and Kranz, R. G. (2003) Chemiluminescent-based methods to detect subpicomole levels of c type cytochromes. *Anal Biochem* 315: 90-94.

Feissner, R. E., Beckett, C. S., Loughman, J. A., and Kranz, R. G. (2005) Mutations in cytochrome assembly and periplasmic redox pathways in *Bordetella pertussis. J Bacteriol* 187: 3941-3949.

Feissner, R. E., Richard-Fogal, C. L., Frawley, E. R., Loughman, J. A., Earley, E. W., and Robert G. Kranz (2006) Recombinant cytochromes c biogenesis systems I and II and analysis of heme delivery pathways in *Escherichia Coli*. Mol Microbiol 60: 537-541.

Fellay, R., Frey, J., and Krisch, H. (1987) Interposon mutagenesis of soil and water bacteria: a family of DNA fragments designed for in vitro insertional mutagenesis of gram-negative bacteria. *Gene* 52: 147-154.

Ferreira, G. C. (1994) Mammalian ferrochelatase. Overexpression in *Escherichia Coli* as a soluble protein, purification and characterization. *Biol Chem* 269: 4396-4400.

Goldman, B. S., Gabbert, K. K., and Kranz, R. G. (1996) Use of heme reporters for studies of cytochrome biosynthesis and heme transport. *J Bacteriol* 178: 6338-6347.

Guzman, L. M., Belin, D., Carson, M. J., and Beckwith, J. (1995) Tight regulation, modulation, and high-level expression by vectors containing the arabinose PBAD promoter. *J Bacteriol* 177: 4121-4130.

Khlebnikov, A., Risa, O., Skaug, T., Carrier, T. A., and Keasling, J. D. (2000) Regulatable arabinose-inducible gene expression system with consistent control in all cells of a culture. *J Bacteriol* 182: 7029-7034.

Moody, M. D., and Dailey, H. A. (1985) Ferric iron reductase of *Rhodopseudomonas sphaeroides*. *J Bacteriol* 163:1120-1125.

Tomb, J. F., White, O., Kerlavage, A. R., Clayton, R. A., Sutton, G. G., Fleischmann, R. D., et al. (1997) The complete genome sequence of the gastric pathogen *Helicobacter pylori*. *Nature* 388: 539-547.

Varnado, C. L., and Goodwin, D.C. (2004) System for the expression of recombinant hemoproteins in *Escherichia coli*. *Protein Expr Purif* 35: 76-83.

What is claimed is:

1. A method for identifying a compound that inhibits cytochrome c synthesis in a bacterial cell, the method comprising: a. contacting a transfected bacterial cell with a compound, the bacterial cell being transfected with a first expression vector encoding Ccm proteins and a second expression vector encoding a cytochrome c reporter protein, wherein the bacterial cell has a chromosomal disruption in the region encoding the Ccm proteins; and b. determining the amount of cytochrome c reporter protein produced in the presence of the compound relative to the amount produced in the absence of the compound, wherein a decrease in amount is an indication that the compound inhibits the synthesis of cytochrome c.

2. The method of claim 1, wherein the transfected bacterial is a gamma proteobacterium cell.

3. The method of claim 2, wherein the transfected bacterial cell is an *Escherichia coli* cell.

4. The method of claim 1, wherein the Ccm proteins coded by the first expression vector are from a gamma proteobacterium.

5. The method of claim 4, wherein the Ccm protiens are the CcmA-H proteins of *Escherichia coli*.

6. The method of claim 1, wherein the second expression vector encodes a cytochrome c:alkaline phosphate fusion protien or a cytochrome c:6xHis fusion protien.

7. The method of claim 6, wherein the cytochrome c protien is cytochrome $c_4$ from *Brodetella pertussis*.

8. The method of claim 1, wherein the coding region of the first expression vector is operably linked to a first inducible promoter and the coding region of the second expression vector is operably linked to a second inducible promoter.

9. The method of claim 8, wherein the first promoter is induced by IPTG and the second promoter is induced by arabinose.

10. The method of claim 1, wherein the transfected bacterial cell grows in the presence of exogenous amino levulinic acid (ALA).

11. The method of claim 1, wherein the transfected bacterial cell further comprises a chromosomal disruption in the region encoding the HemA protein.

* * * * *

UNITED STATES PATENT AND TRADEMARK OFFICE
CERTIFICATE OF CORRECTION

| | |
|---|---|
| PATENT NO. | : 7,790,184 B2 |
| APPLICATION NO. | : 11/831273 |
| DATED | : September 7, 2010 |
| INVENTOR(S) | : Robert Kranz |

It is certified that error appears in the above-identified patent and that said Letters Patent is hereby corrected as shown below:

Col. 38, line 31: "protien" should read --protein--

Col. 38, line 33: "Brodetella" should read --Bordetella--

Signed and Sealed this
Twenty-third Day of August, 2011

David J. Kappos
*Director of the United States Patent and Trademark Office*